(12) United States Patent
Barry et al.

(10) Patent No.: US 11,510,596 B2
(45) Date of Patent: Nov. 29, 2022

(54) PRECONNECTED ANALYTE SENSORS

(71) Applicant: DexCom, Inc., San Diego, CA (US)

(72) Inventors: John Charles Barry, San Diego, CA (US); Patrick John Castagna, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 16/854,664

(22) Filed: Apr. 21, 2020

(65) Prior Publication Data

US 2020/0330036 A1 Oct. 22, 2020

Related U.S. Application Data

(63) Continuation of application No. 16/854,337, filed on Apr. 21, 2020.
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0024* (2013.01); *A61B 5/1468* (2013.01);
(Continued)

(58) Field of Classification Search
CPC ............ A61B 5/14503; A61B 5/14532; A61B 5/1451; A61B 5/14546;
(Continued)

(56) References Cited

U.S. PATENT DOCUMENTS 3,649,743 A * 3/1972 O'Loughlin ............. H01R 4/14
174/84 C
4,865,038 A 9/1989 Rich et al.
(Continued)

FOREIGN PATENT DOCUMENTS

EP 2327984 A2 6/2011
WO WO-9956613 A1 11/1999
(Continued)

OTHER PUBLICATIONS

International Search Report and Written Opinion for Application No. PCT/US2020/029141, dated Jul. 27, 2020, 20 pages.
(Continued)

*Primary Examiner* — Eric F Winakur
*Assistant Examiner* — Alice Ling Zou
(74) *Attorney, Agent, or Firm* — Snell & Wilmer LLP

(57) ABSTRACT

Various analyte sensing apparatuses and associated housings are provided. Some apparatuses comprise one or more caps. Some apparatuses comprise a two-part adhesive patch. Some apparatuses comprise one or more sensor bends configured to locate and/or hold a sensor in place during mounting. Some apparatuses utilize one or more dams and/or wells to retain epoxy for securing a sensor. Some apparatuses utilize a pocket and one or more adjacent areas and various transitions for preventing epoxy from wicking to undesired areas of the apparatus. Some apparatuses include heat-sealable thermoplastic elastomers for welding a cap to the apparatus. Related methods of fabricating such apparatuses and/or housings are also provided.

27 Claims, 38 Drawing Sheets

Related U.S. Application Data

(60) Provisional application No. 62/837,091, filed on Apr. 22, 2019.

(51) Int. Cl.
    *A61B 5/1486*    (2006.01)
    *A61B 5/1468*    (2006.01)

(52) U.S. Cl.
    CPC .......... *A61B 5/6833* (2013.01); *A61B 5/1486* (2013.01); *A61B 5/14546* (2013.01); *A61B 2560/0406* (2013.01); *A61B 2562/12* (2013.01); *A61B 2562/14* (2013.01); *A61B 2562/164* (2013.01); *A61B 2562/18* (2013.01); *A61B 2562/227* (2013.01)

(58) Field of Classification Search
    CPC ... A61B 5/1468–14735; A61B 5/1486–14865; A61B 5/685; A61B 5/6848; A61B 2562/166; A61B 2560/063; A61B 5/6833; A61B 2560/0406–0412; A61B 2562/02; A61B 2562/12; A61B 2562/16; A61B 2562/225–227; A61B 5/6832–6833; A61B 5/6849; A61B 2560/0443–045; A61B 2560/0462–0468; A61B 2562/164–166; A61B 2562/227
    See application file for complete search history.

(56) References Cited

U.S. PATENT DOCUMENTS

| | | | |
|---|---|---|---|
| 6,001,067 A | 12/1999 | Shults et al. | |
| 6,153,070 A | 11/2000 | Maurer et al. | |
| 6,493,212 B1 | 12/2002 | Clarke et al. | |
| 2006/0142651 A1 | 6/2006 | Brister et al. | |
| 2012/0078071 A1 | 3/2012 | Bohm et al. | |
| 2012/0253145 A1* | 10/2012 | Stafford | A61B 5/6849 600/309 |
| 2012/0323098 A1* | 12/2012 | Moein | A61B 5/1486 600/345 |
| 2013/0150691 A1 | 6/2013 | Pace et al. | |
| 2013/0267813 A1* | 10/2013 | Pryor | A61B 5/6849 600/365 |
| 2013/0325352 A1 | 12/2013 | Greene et al. | |
| 2014/0142405 A1 | 5/2014 | Brister et al. | |
| 2015/0164389 A1* | 6/2015 | Varsavsky | A61B 5/1468 600/316 |
| 2016/0058474 A1* | 3/2016 | Peterson | A61B 5/1473 600/347 |
| 2017/0112533 A1 | 4/2017 | Schoonmaker et al. | |
| 2017/0281092 A1 | 10/2017 | Burnette et al. | |
| 2017/0290534 A1 | 10/2017 | Antonio et al. | |
| 2018/0146895 A1* | 5/2018 | Biederman | A61B 5/1473 |
| 2018/0368771 A1 | 12/2018 | Gray et al. | |
| 2019/0092536 A1 | 3/2019 | Freedman et al. | |
| 2019/0117133 A1 | 4/2019 | Halac et al. | |
| 2019/0120785 A1 | 4/2019 | Halac et al. | |
| 2019/0298232 A1 | 10/2019 | Ko et al. | |

FOREIGN PATENT DOCUMENTS

| | | | | |
|---|---|---|---|---|
| WO | WO-2011025549 A1 | 3/2011 | | |
| WO | WO-2018172349 A1 | 9/2018 | | |
| WO | WO-2019081734 A1 * | 5/2019 | ............ | A61B 5/742 |

OTHER PUBLICATIONS

International Preliminary Report on Patentability for Application No. PCT/US2020/029141, dated Nov. 4, 2021, 16 pages.

* cited by examiner

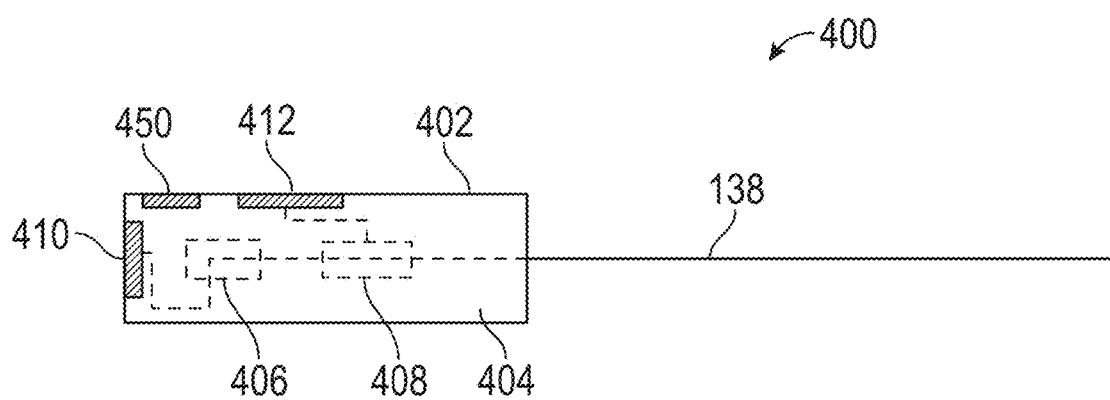
FIG. 4A
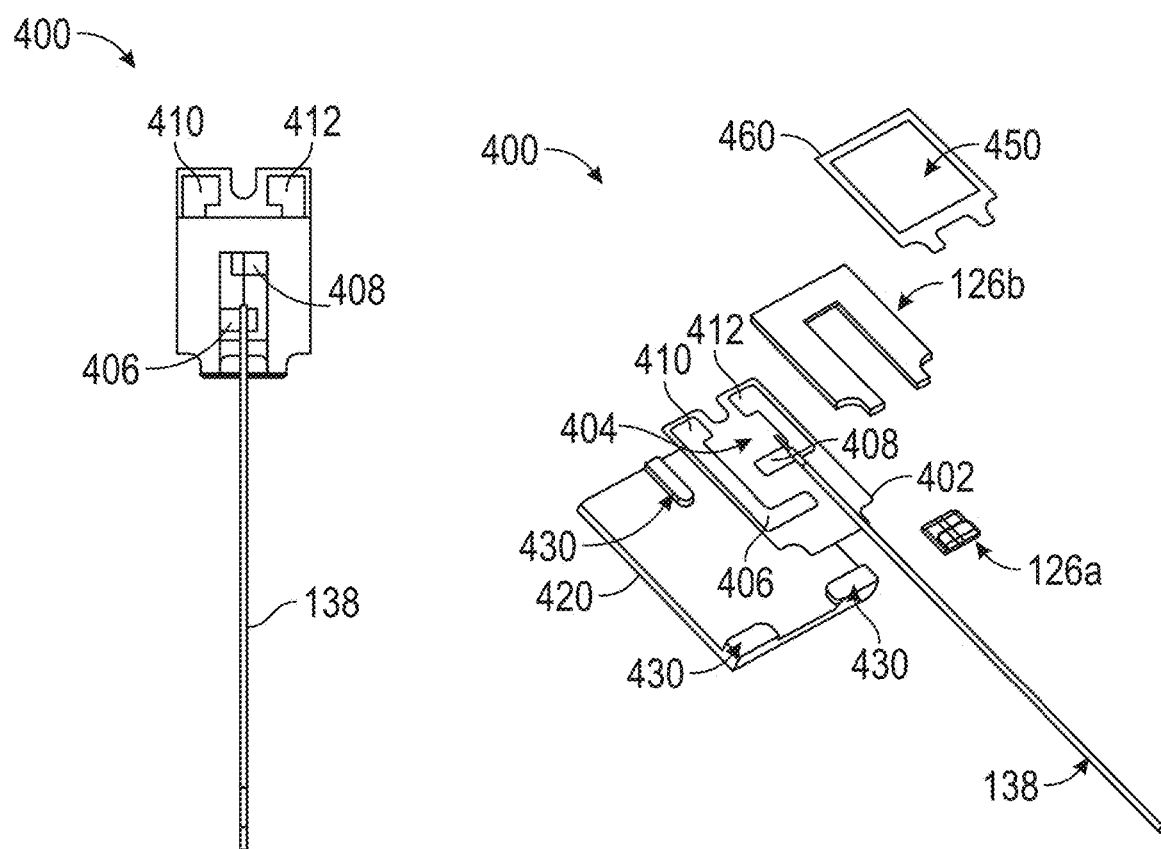
FIG. 4B
FIG. 4C

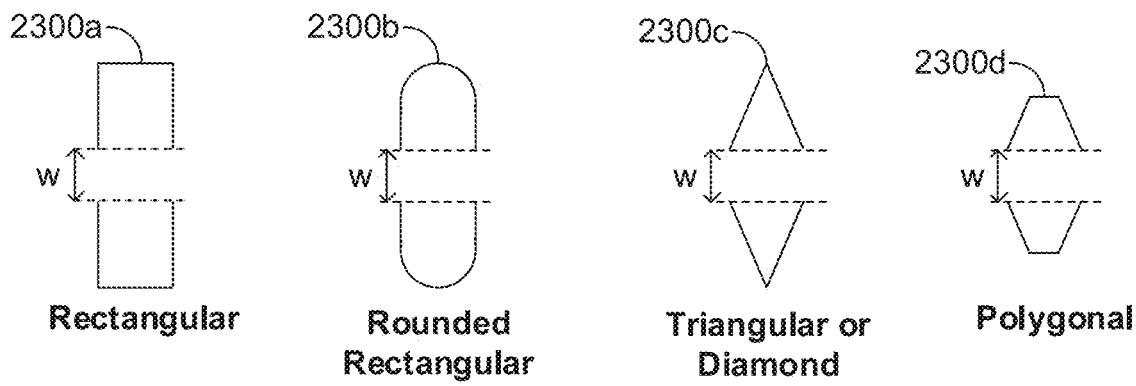
FIG. 23
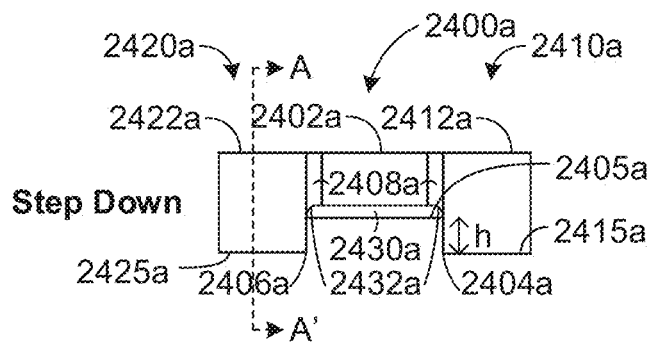
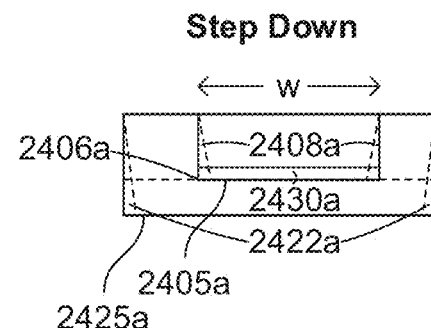
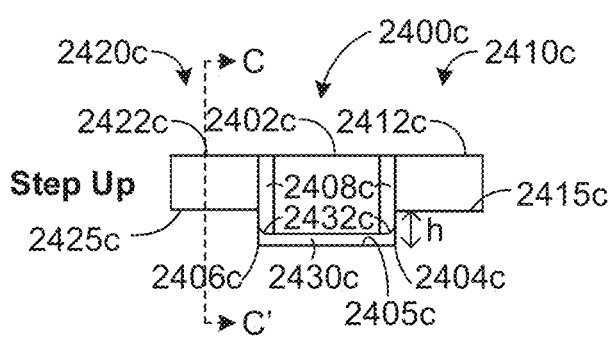
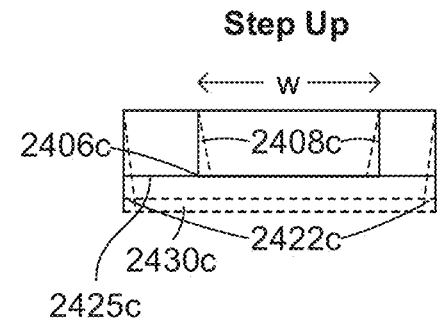
FIG. 24  FIG. 25

PRECONNECTED ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/854,337, filed Apr. 21, 2020, which claims the benefit of U.S. Provisional Application No. 62/837,091, filed Apr. 22, 2019. Each of the aforementioned applications is incorporated by reference herein in its entirety, and each is hereby expressly made a part of this specification.

TECHNICAL FIELD

The present disclosure generally relates to sensors and, more particularly, to analyte sensors such as continuous analyte sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

This Background is provided to introduce a brief context for the Summary and Detailed Description that follow. This Background is not intended to be an aid in determining the scope of the claimed subject matter nor be viewed as limiting the claimed subject matter to implementations or embodiments that solve any or all of the disadvantages or problems presented above.

SUMMARY

According to some embodiments, an analyte sensing apparatus is provided. The apparatus includes a housing comprising a cavity in the housing, the cavity having a first portion and a second portion. The apparatus includes a first conductive contact and a second conductive contact disposed within the first portion of the cavity. The apparatus includes an analyte sensor including an elongated body, a first electrode in electrical communication with the first conductive contact, and a second electrode in electrical communication with the second conductive contact. The apparatus includes a cap configured to fit on or within the cavity. The cap includes a first portion configured to be disposed over the first portion of the cavity, a second portion, a dam disposed on a side of the cap configured to face the cavity, the dam dividing the first portion of the cavity from the second portion of the cavity, a shelf disposed adjacent to the dam, and a compliant component configured to seal the first portion of the cavity from the second portion of the cavity.

In some embodiments, the apparatus includes an electronics assembly substrate disposed within the housing, wherein the first conductive contact and the second conductive contact extend from the electronics assembly substrate into the first portion of the cavity. In some embodiments, the compliant component is disposed on the shelf and configured to press against a portion of the analyte sensor and against a surface of the housing within the cavity, thereby sealing the first portion of the cavity from the second portion of the cavity. In some embodiments, the first portion of the cap includes a first hole configured to receive an encapsulating sealant into the first portion of the cavity that seals at least a portion of the analyte sensor from moisture ingress. In some embodiments, the first portion of the cap includes a second hole configured to allow excess encapsulating sealant to flow out of the first portion of the cavity. In some embodiments, the compliant component prevents the encapsulating sealant from flowing into the second portion of the cavity. In some embodiments, the second portion of the cap is configured to be disposed over the second portion of the cavity. In some embodiments, the second portion of the cap includes a slot configured to allow at least a portion of the analyte sensor to pass through the cap. In some embodiments, an outside-facing surface of the cap is configured to fit flush with an outside-facing surface of the housing. In some embodiments, an outside-facing surface of the cap is configured to fit in a recessed position compared to an outside-facing surface of the housing. In some embodiments, the cap is disposed on an outside-facing surface of the housing. In some embodiments, the cap is secured to the cavity utilizing at least one of a toe feature, a snap feature, a friction-fit feature, and a pressure-sensitive adhesive. In some embodiments, the first portion of the cap and the second portion of the cap are coplanar and are formed of a single piece. In some embodiments, the encapsulating sealant is a curable sealant configured to cure based on exposure to ultra-violet radiation and wherein the cap includes a material substantially transparent to the ultra-violet radiation. In some embodiments, the dam is configured to contact a portion of the housing within the cavity. In some embodiments, the compliant material includes a foam or a rubber material.

In some embodiments, the apparatus includes an adhesive patch, including a first adhesive portion configured to secure the cap to the housing and to simultaneously adhere to the housing and a second adhesive portion configured to adhere the first adhesive portion and the wearable assembly to a skin of a host. In some embodiments, the cap is secured to the first adhesive portion of the adhesive patch before the cap is fit on or within the cavity of the housing. In some embodiments, the first adhesive portion includes at least one hole configured to substantially coincide with at least one hole within the cap when the cap is secured to the first adhesive portion of the adhesive patch. In some embodiments, the second adhesive portion of the adhesive patch is initially disposed on a separate liner from the first adhesive portion of the adhesive patch. In some embodiments, the second adhesive portion includes at least one hole configured to substantially coincide with at least one hole within the cap when the cap is secured to the second adhesive portion of the adhesive patch.

In some embodiments, the second portion of the cap is configured to be disposed adjacent to the second portion of the cavity. In some embodiments, the first portion of the cap extends along a first plane, the second portion of the cap extends along a second plane different from the first plane, the dam includes at least a portion of the cap that extends between the first plane and the second plane and connects the first portion of the cap with the second portion of the cap, and at least some of the second portion of the cap includes the shelf.

In some embodiments, the apparatus includes at least one passivation layer deposited over at least a portion of the first portion of the cavity and over at least a portion of the sensor, the at least one passivation layer preventing moisture ingress to the portion of the sensor. In some embodiments, the apparatus includes one or more conductive traces deposited on the at least one passivation layer and electrically coupled to one of the first conductive contact and the second conductive contact.

According to some embodiments, an analyte sensing apparatus includes a housing, an electronics assembly substrate disposed within the housing, and an analyte sensor including an elongated body having at least a first bend.

In some embodiments, the first bend is oriented such that a portion of the elongated body distal of the first bend extends substantially parallel to a plane of the electronics assembly substrate and a portion of the elongated body proximal to the first bend extends substantially perpendicular to the plane of the electronics assembly substrate and at least partially into the electronics assembly substrate. In some embodiments, the housing includes a recess and at least some of the portion of the elongated body proximal to the first bend extends through the electronics assembly substrate and into the recess. In some embodiments, the portion of the elongated body proximal to the first bend exerts a biasing force against a portion of the electronics assembly substrate, thereby securing the analyte sensor in a desired orientation with respect to the electronics assembly substrate.

In some embodiments, the first bend is oriented such that a portion of the elongated body distal of the first bend extends substantially parallel to a plane of the electronics assembly substrate and a portion of the elongated body proximal to the first bend extends substantially perpendicular to the plane of the electronics assembly substrate and away from the electronics assembly substrate. In some embodiments, the housing further includes a recess in a sidewall of the housing, at least some of the portion of the elongated body proximal to the first bend extending within the recess and thereby restraining the analyte sensor in a desired orientation with respect to the electronics assembly substrate. In some embodiments, the portion of the elongated body proximal to the first bend exerts a biasing force against a portion of the housing, thereby securing the analyte sensor in a desired orientation with respect to the electronics assembly substrate. In some embodiments, the elongated body of the analyte sensor includes at least one additional bend proximal to the first bend. The at least one additional bend causes at least a first part of the portion of the elongated body proximal to the first bend and distal to the at least one additional bend to extend in a first direction within the recess and exert a first biasing force at a first location along the recess, and at least a second part of the portion of the elongated body proximal to the first bend and proximal to the at least one additional bend to extend in a second direction within the recess and exert a second biasing force at a second location along the recess, thereby securing the analyte sensor in a desired orientation with respect to the electronics assembly substrate.

In some embodiments, the first bend is oriented such that a portion of the elongated body distal of the first bend extends in a first direction substantially parallel to a plane of the electronics assembly substrate and a portion of the elongated body proximal to the first bend extends in a second direction that is different from the first direction but also substantially parallel to the plane of the electronics assembly substrate. In some embodiments, the elongated body of the analyte sensor includes at least one additional bend proximal to the first bend. The at least one additional bend causes at least a first part of the portion of the elongated body proximal to the first bend and distal to the at least one additional bend to extend in the second direction and exert a first biasing force at a first location along one of the housing and the electronics assembly substrate, and at least a second part of the portion of the elongated body proximal to the first bend and proximal to the at least one additional bend to extend in a third direction substantially parallel to the plane of the electronics assembly substrate and exert a second biasing force at a second location along one of the housing and the electronics assembly substrate, thereby securing the analyte sensor in a desired orientation with respect to the electronics assembly substrate. In some embodiments, the electronic assembly substrate includes a post and the first bend is oriented such that a portion of the elongated body distal of the first bend extends in a first direction substantially parallel to a plane of the electronics assembly substrate and a portion of the elongated body proximal to the first bend extends substantially along a perimeter of the post, thereby securing the analyte sensor in a desired orientation with respect to the electronics assembly substrate. In some embodiments, the portion of the elongated body distal of the first bend exerts a first biasing force at a first location along one of the housing and the electronics assembly substrate, thereby securing the analyte sensor in a desired orientation with respect to the electronics assembly substrate. In some embodiments, the first bend exerts a second biasing force at a second location along one of the housing and the electronics assembly substrate, thereby further securing the analyte sensor in the desired orientation. In some embodiments, the portion of the elongated body proximal of the first bend exerts a third biasing force at a third location along one of the housing and the electronics assembly substrate, thereby further securing the analyte sensor in the desired orientation. In some embodiments, the second biasing force is exerted in a substantially opposite direction from the third biasing force. In some embodiments, the first biasing force is exerted in a substantially perpendicular direction to each of the second biasing force and the third biasing force. In some embodiments, the first bend provides a first torque about the first bend that pushes the portion of the elongated body distal of the first bend against the first location. In some embodiments, the first bend provides a second torque about the first bend that pushes the portion of the elongated body proximal of the first bend against the third location.

According to some embodiments, an analyte sensing apparatus includes a housing having a cavity having a first portion and a second portion, a first conductive contact disposed in the first portion of the cavity, a second conductive contact disposed in the first portion of the cavity, and a first well encompassing the first conductive contact. The first well is defined by a first dam disposed adjacent to a first side of the first conductive contact, and a second dam disposed adjacent to a second side of the first conductive contact opposite the first side. The apparatus includes an analyte sensor having an elongated body, a first electrode in electrical communication with the first conductive contact, and a second electrode in electrical communication with the second conductive contact, wherein the analyte sensor rests on the first dam and on the second dam.

In some embodiments, the apparatus includes an electronics assembly substrate disposed within the housing, wherein the first conductive contact and the second conductive contact extend from the electronics assembly substrate into the first portion of the cavity. In some embodiments, the first dam and the second dam each include a sloped cross-section, the analyte sensor resting on a lowest point of the sloped cross-section of the first dam and on a lowest point of the sloped cross-section of the second dam. In some embodiments, the sloped cross-sections of the first and second dams are one of triangularly-recessed, parabolically-recessed, semi-circularly-recessed or hyperbolically-recessed cross-sections. In some embodiments, the apparatus includes conductive epoxy disposed over at least a portion of the first conductive contact within the first well. In some embodiments, the conductive epoxy is disposed at least to a height of the lowest point of the sloped cross-section of the first dam or of the lowest point of the sloped cross-section of the second dam such that the first electrode of the analyte sensor is in direct physical and electrical contact with the conductive epoxy.

According to some embodiments, an analyte sensing apparatus housing includes a first pocket having a first pocket base, a first adjacent area abutting a first side of the first pocket, the first adjacent area having a first adjacent area base and a first transition between the first pocket base and the first adjacent area base, and a second adjacent area abutting a second side of the first pocket, the second adjacent area having a second adjacent area base and a second transition between the first pocket base and the second adjacent area base. The first and second adjacent areas are continuous with the first pocket.

In some embodiments, the housing includes an electronics assembly substrate disposed within the housing. In some embodiments, the first pocket has a substantially rectangular-shaped geometry such that sidewalls of the first pocket are substantially planar and meet one another to form angled corners. In some embodiments, the first pocket has a substantially rounded rectangular-shaped geometry such that portions of sidewalls of the first pocket are substantially planar while other portions of the sidewalls that connect the substantially planar portions are curved. In some embodiments, the first pocket has a substantially diamond-shaped geometry such that sidewalls of the first pocket are substantially planar and meet one another to form angled corners. In some embodiments, the first pocket has a substantially rounded diamond-shaped geometry such that portions of sidewalls of the first pocket are substantially planar while other portions of the sidewalls that connect the substantially planar portions are curved. In some embodiments, the first pocket has a substantially polygonal-shaped geometry such that sidewalls of the first pocket are substantially planar and meet one another to form angled corners. In some embodiments, the first pocket has a substantially rounded polygonal-shaped geometry such that portions of sidewalls of the first pocket are substantially planar while other portions of the sidewalls that connect the substantially planar portions are curved. In some embodiments, at least one of the first adjacent area base and the second adjacent area base are disposed at an elevated height compared to the first pocket base. In some embodiments, the at least one of the first transition and the second transition step up from the first pocket base. In some embodiments, the elevated height is approximately 0.5 millimeters. In some embodiments, the housing includes epoxy disposed on the pocket base, wherein the epoxy forms an upward-inflecting meniscus at the at least one of the first and second transitions and the elevated height exceeds a height of the upward-inflecting meniscus. In some embodiments, the elevated height is a function of the first predetermined amount and at least one of a viscosity, a surface energy and a surface tension characteristic of the epoxy. In some embodiments, at least one of the first adjacent area base and the second adjacent area base are disposed at a same height as the first pocket base. In some embodiments, at least one of the first transition and the second transition are flush with the first pocket base. In some embodiments, at least one of the first adjacent area base and the second adjacent area base are disposed at a lower height compared to the first pocket base. In some embodiments, at least one of the first transition and the second transition step down from the first pocket base. In some embodiments, the lower height is approximately 0.5 millimeters. In some embodiments, the housing includes epoxy disposed on the pocket base, wherein the epoxy forms a downward-inflecting meniscus at the at least one of the first and second transitions. In some embodiments, the epoxy adheres to the at least one of the first and second transitions and inhibits the epoxy from creeping into the at least one of the first and second transitions. In some embodiments, one of the first adjacent area base and the second adjacent area base is disposed at a lower height compared to the first pocket base and the other of the first adjacent area base and the second adjacent area base is disposed at an elevated height compared to the first pocket base. In some embodiments, both of the first adjacent area base and the second adjacent area base is disposed at a lower height compared to the first pocket base. In some embodiments, the first adjacent area has any of a substantially rectangular-shaped geometry, a substantially rounded rectangular-shaped geometry, a substantially diamond-shaped geometry, a substantially rounded diamond-shaped geometry, a substantially polygonal-shaped geometry, a substantially rounded polygonal-shaped geometry, and a substantially irregular-shaped geometry. In some embodiments, the second adjacent area has any of a substantially rectangular-shaped geometry, a substantially rounded rectangular-shaped geometry, a substantially diamond-shaped geometry, a substantially rounded diamond-shaped geometry, a substantially polygonal-shaped geometry, a substantially rounded polygonal-shaped geometry, and a substantially irregular-shaped geometry. In some embodiments, sidewalls of the first pocket are disposed substantially perpendicular to the first pocket base. In some embodiments, sidewalls of the first pocket are disposed at an angle from substantially perpendicular to the first pocket base. In some embodiments, sidewalls of at least one of the first and second adjacent areas are disposed substantially perpendicular to the respective first and second adjacent area bases. In some embodiments, sidewalls of at least one of the first and second adjacent areas are disposed at an angle from substantially perpendicular to the respective first and second adjacent area bases. In some embodiments, sidewalls of at least one of the first and second transitions are disposed substantially perpendicular to the first pocket base. In some embodiments, sidewalls of at least one of the first and second transitions are disposed at an angle from substantially perpendicular to the first pocket base. In some embodiments, sidewalls of at least one of the first and second transitions are rounded such that angled corners are not formed at the at least one of the first and second transitions. In some embodiments, a first width of the first transition and a second width of the second transition are substantially within the range of 0.5 mm and 2.0 mm. In some embodiments, a first width of the first transition is greater than a second width of the second transition. In some embodiments, a first width of the first transition is less than a second width of the second transition. In some embodiments, the housing includes a conductive contact disposed in the first adjacent area or in the second adjacent area. In some embodiments, the housing includes an analyte sensor having an elongated body, a first electrode, and a second electrode. One of the first electrode and the second electrode is in electrical communication with the conductive contact.

In some embodiments, the housing includes a post disposed in the first adjacent area or in the second adjacent area, and epoxy disposed on the post. A portion of the analyte sensor is disposed in the epoxy disposed on the post. In some embodiments, the epoxy disposed on the post exerts a centering force on the portion of the analyte sensor disposed therein such that the analyte sensor is aligned substantially along a centerline of the post. In some embodiments, the post has a substantially symmetrical geometry about a centerline of the post.

In some embodiments, the first pocket base has a first surface energy and the first adjacent area base has a second surface energy different from the first surface energy. In some embodiments, the second adjacent area base has one of the second surface energy and a third surface energy different from the first and second surface energies.

In some embodiments, the housing includes a third adjacent area abutting the first pocket, the third adjacent area having a third adjacent area base disposed at a lower elevation than a top surface of a sidewall of the first pocket and a third transition between the top surface of the sidewall of the first pocket and the third adjacent area base. In some embodiments, epoxy disposed within the first pocket adheres to the third transition and inhibits the epoxy from creeping into the third adjacent area. In some embodiments, the third adjacent area is configured to accept at least an excess portion of epoxy disposed within the first pocket, thereby preventing the epoxy from creeping into at least one of the first and second adjacent areas.

According to some embodiments, analyte sensing apparatus includes a housing. The housing includes a first pocket having a first pocket base, a first adjacent area abutting a first side of the first pocket, the first adjacent area having a first adjacent area base and a first transition between the first pocket base and the first adjacent area base, a second adjacent area abutting a second side of the first pocket, the second adjacent area having a second adjacent area base and a second transition between the first pocket base and the second adjacent area base, and a conductive contact disposed in the first adjacent area or in the second adjacent area. The apparatus includes an electronics assembly substrate disposed within the housing and electrically coupled to the conductive contact. The apparatus includes an analyte sensor including at least one electrode in electrical communication with the conductive contact and epoxy disposed on the first pocket base, the epoxy securing at least a portion of the analyte sensor to the first pocket base.

In some embodiments, at least one of the first adjacent area base and the second adjacent area base are disposed at an elevated height compared to the first pocket base. In some embodiments, the epoxy forms an upward-inflecting meniscus at the at least one of the first and second transitions and the elevated height exceeds a height of the upward-inflecting meniscus. In some embodiments, at least one of the first adjacent area base and the second adjacent area base are disposed at a same height as the first pocket base. In some embodiments, at least one of the first adjacent area base and the second adjacent area base are disposed at a reduced height compared to the first pocket base. In some embodiments, the epoxy forms a downward-inflecting meniscus at the at least one of the first and second transitions. In some embodiments, the epoxy adheres to the at least one of the first and second transitions and inhibits the epoxy from creeping into the at least one of the first and second transitions.

According to some embodiments, an analyte sensing apparatus includes a housing including an aperture that defines a cavity in the housing, the cavity having a first portion and a second portion. The apparatus includes a first heat-sealable thermoplastic elastomer disposed along a perimeter of the first portion of the cavity. The apparatus includes an analyte sensor having at least a portion disposed within the first portion of the cavity. The apparatus includes a cap configured to fit on or within the aperture and over the first portion of the cavity. The cap includes a second heat-sealable thermoplastic elastomer along at least a portion of the cap disposed over a border between the first and second portions of the cavity. The first and second heat-sealable thermoplastic elastomers are configured to seal the first portion of the cavity from moisture ingress upon being melted. In some embodiments, the border between the first and second portions of the cavity includes a portion of the first heat-sealable thermoplastic elastomer.

According to some embodiments, an analyte sensing apparatus includes a housing including a cavity in the housing, a first conductive contact, a second conductive contact, and a cap configured to fit on or within the aperture. The analyte sensor includes an elongated body, a first electrode in physical contact with the first conductive contact, and a second electrode in physical contact with the second conductive contact. The cap includes a base, and a sealing material configured to at least partially fill the cavity. The sealing member includes a first cavity configured to align over the first electrode and the first conductive contact and a second cavity configured to align over the second electrode and the second conductive contact.

In some embodiments, the first cavity contains a first conductive elastomeric puck and the second cavity contains a second conductive elastomeric puck. In some embodiments, the first conductive elastomeric puck is configured to press against the first electrode and the first conductive contact, and the second conductive elastomeric puck is configured to press against the second electrode and the second conductive contact. In some embodiments, the first conductive elastomeric puck secures the first electrode to the first conductive contact and the second conductive elastomeric puck secures the second electrode to the second conductive contact. In some embodiments, the first conductive elastomeric puck is configured to press against the first electrode and the cap, and the second conductive elastomeric puck is configured to press against the second electrode and the second conductive contact. In some embodiments, the first and second conductive elastomeric pucks have a substantially cylindrical shape. In some embodiments, the first conductive contact has a gap formed within. In some embodiments, the first conductive elastomeric puck is disposed within the gap of the first conductive contact. In some embodiments, the first conductive elastomeric puck is disposed within the gap of the first conductive contact by press fit. In some embodiments, the first cavity is configured to retain a first injection of conductive epoxy configured to electrically couple the first electrode and the first conductive contact. In some embodiments, the second cavity is configured to retain a second injection of conductive epoxy configured to electrically couple the second electrode and the second conductive contact. In some embodiments, the first and second cavities have a substantially conical shape. In some embodiments, the base of the cap further includes at least a first hole that aligns laterally with the first cavity and a second hole that aligns laterally with the second cavity, at least a portion of the sealing material physically isolating the first hole from the first cavity and the second hole from the second cavity.

According to some embodiments, a method for fabricating an analyte sensing apparatus includes forming a housing including an aperture that defines a cavity having a first portion and a second portion in the housing. The method includes disposing a first conductive contact and a second conductive contact in the first portion of the cavity. The method includes electrically coupling a first electrode of an analyte sensor to the first conductive contact. The method includes electrically coupling a second electrode of the analyte sensor to the second conductive contact. The method includes forming a cap having a first portion and a second portion, a dam disposed on a side of the cap configured to face the aperture, a shelf adjacent to the dam, and a compliant component disposed on the shelf. The method includes fitting the cap on or within the aperture such that the first portion of the cap is disposed over the first portion of the cavity, the dam physically divides the first portion of the cavity from the second portion of the cavity, and the compliant component presses against a portion of the analyte sensor and against a surface of the housing within the cavity, thereby sealing the first portion of the cavity from the second portion of the cavity.

In some embodiments, the method includes disposing an electronics assembly substrate within the housing, wherein the first conductive contact and the second conductive contact extend from the electronics assembly substrate into the first portion of the cavity. In some embodiments, the first portion of the cap includes a first hole, the method further including depositing an encapsulating sealant into the first portion of the cavity through the first hole, thereby sealing at least a portion of the analyte sensor from moisture ingress. In some embodiments, the first portion of the cap includes a second hole, the method further including allowing excess encapsulating sealant to flow out of the first portion of the cavity through the second hole. In some embodiments, the compliant component prevents the encapsulating sealant from flowing into the second portion of the cavity. In some embodiments, the cap includes a second portion disposed over the second portion of the cavity. In some embodiments, the second portion of the cap includes a slot, the method further including causing at least a portion of the analyte sensor to pass through the slot. In some embodiments, an outside-facing surface of the cap fits flush with an outside-facing surface of the housing. In some embodiments, an outside-facing surface of the cap fits in a recessed position compared to an outside-facing surface of the housing. In some embodiments, the cap is disposed on an outside-facing surface of the housing. In some embodiments, the method includes securing the cap to the housing utilizing at least one of a toe feature, a snap feature, a friction-fit feature, and a pressure-sensitive adhesive. In some embodiments, the first portion of the cap and the second portion of the cap are coplanar and formed of a single piece. In some embodiments, the cap includes a material substantially transparent to ultra-violet radiation, the method further including curing the encapsulating sealant by exposing the encapsulating sealant to the ultra-violet radiation through the cap. In some embodiments, the dam contacts a portion of the housing within the cavity. In some embodiments, the compliant material includes a foam or a rubber material.

In some embodiments, the method includes securing the cap to the housing utilizing a first adhesive portion of an adhesive patch, the adhesive patch further including a second adhesive portion configured to adhere the first adhesive portion and the wearable assembly to a skin of a host. In some embodiments, the method includes securing the first adhesive portion of the adhesive patch to the cap before the cap is fit on or within the aperture of the housing. In some embodiments, the first adhesive portion includes at least one hole configured to substantially coincide with at least one hole within the cap when the cap is secured to the first adhesive portion of the adhesive patch. In some embodiments, the second adhesive portion includes at least one hole configured to substantially coincide with at least one hole within the cap when the cap is secured to the second adhesive portion of the adhesive patch.

In some embodiments, a second portion of the cap is disposed adjacent to the second portion of the cavity. In some embodiments, the first portion of the cap extends along a first plane, the second portion of the cap extends along a second plane different from the first plane, the dam includes at least a portion of the cap that extends between the first plane and the second plane and connects the first portion of the cap with the second portion of the cap, and at least some of the second portion of the cap includes the shelf.

In some embodiments, the method includes depositing at least one passivation layer over at least a portion of the first portion of the cavity and over at least a portion of the analyte sensor, thereby preventing moisture ingress to the portion of the sensor. In some embodiments, the method includes depositing one or more conductive traces on the at least one passivation layer and electrically coupling the one or more conductive traces to one or more of the first conductive contact and the second conductive contact.

According to some embodiments, a method of fabricating an analyte sensing apparatus includes fabricating a housing, disposing an electronics assembly substrate within the housing, and coupling an analyte sensor including an elongated body having at least a first bend to at least one of the housing and the electronics assembly substrate.

In some embodiments, the method includes forming the first bend in the analyte sensor such that a portion of the elongated body distal of the first bend extends substantially parallel to a plane of the electronics assembly substrate and a portion of the elongated body proximal to the first bend extends substantially perpendicular to the plane of the electronics assembly substrate and at least partially into the electronics assembly substrate. In some embodiments, the housing includes a recess, the method further including extending at least some of the portion of the elongated body proximal to the first bend through the electronics assembly substrate and into the recess. In some embodiments, the portion of the elongated body proximal to the first bend exerts a biasing force against a portion of the electronics assembly substrate, thereby securing the analyte sensor in a desired orientation with respect to the electronics assembly substrate.

In some embodiments, the method includes forming the first bend in the analyte sensor such that a portion of the elongated body distal of the first bend extends substantially parallel to a plane of the electronics assembly substrate and a portion of the elongated body proximal to the first bend extends substantially perpendicular to the plane of the electronics assembly substrate and away from the electronics assembly substrate. In some embodiments, the housing further includes a recess in a sidewall of the housing, the method further including extending at least some of the portion of the elongated body proximal to the first bend within the recess, thereby restraining the analyte sensor in a desired orientation with respect to the electronics assembly substrate. In some embodiments, the portion of the elongated body proximal to the first bend exerts a biasing force against a portion of the housing, thereby securing the analyte sensor in a desired orientation with respect to the electronics assembly substrate. In some embodiments, the method includes forming at least one additional bend in the analyte sensor proximal to the first bend such that the at least one additional bend causes at least a first part of the elongated body proximal to the first bend and distal to the at least one additional bend to extend in a first direction within the recess and exert a first biasing force at a first location along the recess, and at least a second part of the elongated body proximal to the first bend and proximal to the at least one additional bend to extend in a second direction within the recess and exert a second biasing force at a second location along the recess, thereby securing the analyte sensor in a desired orientation with respect to the electronics assembly substrate.

In some embodiments, the method includes forming the first bend in the analyte sensor such that a portion of the elongated body distal of the first bend extends in a first direction substantially parallel to a plane of the electronics assembly substrate and a portion of the elongated body proximal to the first bend extends in a second direction that is different from the first direction but also substantially parallel to the plane of the electronics assembly substrate. In some embodiments, the method includes forming at least one additional bend in the analyte sensor proximal to the first bend such that the at least one additional bend causes at least a first part of the elongated body proximal to the first bend and distal to the at least one additional bend to extend in the second direction and exert a first biasing force at a first location along one of the housing and the electronics assembly substrate, and at least a second part of the elongated body proximal to the first bend and proximal to the at least one additional bend to extend in a third direction substantially parallel to the plane of the electronics assembly substrate and exert a second biasing force at a second location along one of the housing and the electronics assembly substrate, thereby securing the analyte sensor in a desired orientation with respect to the electronics assembly substrate.

In some embodiments, the electronic assembly substrate includes a post and the method includes forming the first bend in the analyte sensor such that a portion of the elongated body distal of the first bend extends in a first direction substantially parallel to a plane of the electronics assembly substrate and a portion of the elongated body proximal to the first bend extends substantially along a perimeter of the post, thereby securing the analyte sensor in a desired orientation with respect to the electronics assembly substrate. In some embodiments, the portion of the elongated body distal of the first bend exerts a first biasing force at a first location along one of the housing and the electronics assembly substrate, thereby securing the analyte sensor in a desired orientation with respect to the electronics assembly substrate. In some embodiments, the first bend exerts a second biasing force at a second location along one of the housing and the electronics assembly substrate, thereby further securing the analyte sensor in the desired orientation. In some embodiments, wherein the portion of the elongated body proximal of the first bend exerts a third biasing force at a third location along one of the housing and the electronics assembly substrate, thereby further securing the analyte sensor in the desired orientation. In some embodiments, the second biasing force is exerted in a substantially opposite direction from the third biasing force. In some embodiments, the first biasing force is exerted in a substantially perpendicular direction to each of the second biasing force and the third biasing force. In some embodiments, the first bend provides a first torque about the first bend that pushes the portion of the elongated body distal of the first bend against the first location. In some embodiments, the first bend provides a second torque about the first bend that pushes the portion of the elongated body proximal of the first bend against the third location.

According to some embodiments a method of fabricating an analyte sensing apparatus is provided. The method includes forming a housing including a cavity having a first portion and a second portion. The method includes forming a first dam in the first portion of the cavity adjacent to a first side of the first conductive contact. The method includes forming a second dam in the first portion of the cavity adjacent to a second side of the first conductive contact opposite the first side, the first dam and the second dam defining a first well encompassing the first conductive contact. The method includes disposing an analyte sensor on the first dam and on the second dam. The method includes coupling a first electrode of the analyte sensor to the first conductive contact. The method includes coupling a second electrode of the analyte sensor to the second conductive contact.

In some embodiments, the method includes disposing an electronics assembly substrate within the housing, wherein the first and second conductive contacts extend from the electronics assembly substrate into the first portion of the cavity. In some embodiments, the first dam and the second dam each include a sloped cross-section, the analyte sensor resting on a lowest point of the sloped cross-section of the first dam and on a lowest point of the sloped cross-section of the second dam. In some embodiments, the sloped cross-sections of the first and second dams are one of triangularly-recessed, parabolically-recessed, semi-circularly-recessed or hyperbolically-recessed cross-sections. In some embodiments, the method includes disposing conductive epoxy over at least a portion of the first conductive contact within the first well. In some embodiments, the conductive epoxy is disposed at least to a height of the lowest point of the sloped cross-section of the first dam or of the lowest point of the sloped cross-section of the second dam such that the first electrode of the analyte sensor is in direct physical and electrical contact with the conductive epoxy when disposed on the first dam and on the second dam.

According to some embodiments, a method of fabricating an analyte sensing apparatus housing is provided. The method includes forming a first pocket having a first pocket base in the housing. The method includes forming a first adjacent area in the housing abutting a first side of the first pocket, the first adjacent area having a first adjacent area base and a first transition between the first pocket base and the first adjacent area base. The method includes forming a second adjacent area in the housing abutting a second side of the first pocket, the second adjacent area having a second adjacent area base and a second transition between the first pocket base and the second adjacent area base.

In some embodiments, the method includes disposing an electronics assembly substrate within the housing. In some embodiments, the first pocket has a substantially rectangular-shaped geometry such that sidewalls of the first pocket are substantially planar and meet one another to form angled corners. In some embodiments, the first pocket has a substantially rounded rectangular-shaped geometry such that portions of sidewalls of the first pocket are substantially planar while other portions of the sidewalls that connect the substantially planar portions are curved. In some embodiments, the first pocket has a substantially diamond-shaped geometry such that sidewalls of the first pocket are substantially planar and meet one another to form angled corners. In some embodiments, the first pocket has a substantially rounded diamond-shaped geometry such that portions of sidewalls of the first pocket are substantially planar while other portions of the sidewalls that connect the substantially planar portions are curved. In some embodiments, the first pocket has a substantially polygonal-shaped geometry such that sidewalls of the first pocket are substantially planar and meet one another to form angled corners. In some embodiments, the first pocket has a substantially rounded polygonal-shaped geometry such that portions of sidewalls of the first pocket are substantially planar while other portions of the sidewalls that connect the substantially planar portions are curved. In some embodiments, at least one of the first adjacent area base and the second adjacent area base are disposed at an elevated height compared to the first pocket base such that at least one of the first transition and the second transition step up from the first pocket base. In some embodiments, the elevated height is approximately 0.5 millimeters. In some embodiments, the method includes depositing epoxy on the pocket base, wherein the epoxy forms an upward-inflecting meniscus at the at least one of the first and second transitions and the elevated height exceeds a height of the upward-inflecting meniscus. In some embodiments, the elevated height is a function of the first predetermined amount and at least one of a viscosity, a surface energy and a surface tension characteristic of the epoxy. In some embodiments, at least one of the first adjacent area base and the second adjacent area base are disposed at a same height as the first pocket base. In some embodiments, at least one of the first transition and the second transition are flush with the first pocket base. In some embodiments, the method includes depositing epoxy on the pocket base, wherein at least one of the first adjacent area base and the second adjacent area base are disposed at a lower height compared to the first pocket base. In some embodiments, the elevated height is a function of the first predetermined amount and at least one of a viscosity, a surface energy and a surface tension characteristic of the epoxy. In some embodiments, at least one of the first adjacent area base and the second adjacent area base are disposed at a same height as the first pocket base. In some embodiments, at least one of the first transition and the second transition are flush with the first pocket base. In some embodiments, the method includes depositing epoxy on the pocket base, wherein at least one of the first adjacent area base and the second adjacent area base are disposed at a lower height compared to the first pocket base. In some embodiments, at least one of the first transition and the second transition step down from the first pocket base. In some embodiments, the lower height is approximately 0.5 millimeters. In some embodiments, the epoxy forms a downward-inflecting meniscus at the at least one of the first and second transitions. In some embodiments, the epoxy adheres to the at least one of the first and second transitions and inhibits the epoxy from creeping into the at least one of the first and second transitions. In some embodiments, one of the first adjacent area base and the second adjacent area base is disposed at a lower height compared to the first pocket base and the other of the first adjacent area base and the second adjacent area base is disposed at an elevated height compared to the first pocket base. In some embodiments, both of the first adjacent area base and the second adjacent area base is disposed at a lower height compared to the first pocket base. In some embodiments, the first adjacent area has any of a substantially rectangular-shaped geometry, a substantially rounded rectangular-shaped geometry, a substantially diamond-shaped geometry, a substantially rounded diamond-shaped geometry, a substantially polygonal-shaped geometry, a substantially rounded polygonal-shaped geometry, and a substantially irregular-shaped geometry. In some embodiments, the second adjacent area has any of a substantially rectangular-shaped geometry, a substantially rounded rectangular-shaped geometry, a substantially diamond-shaped geometry, a substantially rounded diamond-shaped geometry, a substantially polygonal-shaped geometry, a substantially rounded polygonal-shaped geometry, and a substantially irregular-shaped geometry. In some embodiments, sidewalls of the first pocket are disposed substantially perpendicular to the first pocket base. In some embodiments, sidewalls of the first pocket are disposed at an angle from substantially perpendicular to the first pocket base. In some embodiments, sidewalls of at least one of the first and second adjacent areas are disposed substantially perpendicular to the respective first and second adjacent area bases. In some embodiments, sidewalls of at least one of the first and second adjacent areas are disposed at an angle from substantially perpendicular to the respective first and second adjacent area bases. In some embodiments, sidewalls of at least one of the first and second transitions are disposed substantially perpendicular to the first pocket base. In some embodiments, sidewalls of at least one of the first and second transitions are disposed at an angle from substantially perpendicular to the first pocket base. In some embodiments, sidewalls of at least one of the first and second transitions are rounded such that angled corners are not formed at the at least one of the first and second transitions. In some embodiments, a first width of the first transition and a second width of the second transition are substantially within the range of 0.5 mm and 2.0 mm. In some embodiments, a first width of the first transition is greater than a second width of the second transition. In some embodiments, a first width of the first transition is less than a second width of the second transition. In some embodiments, the method includes disposing a conductive contact in the first adjacent area or in the second adjacent area. In some embodiments, the method includes disposing an analyte sensor having a first electrode and a second electrode on the housing and electrically connecting one of the first electrode and the second electrode with the conductive contact.

In some embodiments, the method includes disposing a post in the first adjacent area or in the second adjacent area, disposing epoxy on the post, and disposing a portion of the analyte sensor in the epoxy disposed on the post. In some embodiments, the epoxy exerts a centering force on the portion of the analyte sensor disposed therein such that the analyte sensor is aligned substantially along a centerline of the post. In some embodiments, the post has a substantially symmetrical geometry about a centerline of the post.

In some embodiments, the method includes forming the pocket base with a first surface energy and forming the first adjacent area base with a second surface energy different from the first surface energy. In some embodiments, the method includes forming the second adjacent area base with one of the second surface energy and a third surface energy different from the first and second surface energies.

In some embodiments, the method includes forming a third adjacent area abutting the first pocket, the third adjacent area having a third adjacent area base disposed at a lower elevation than a top surface of a sidewall of the first pocket and a third transition between the top surface of the sidewall of the first pocket and the third adjacent area base. In some embodiments, epoxy disposed within the first pocket adheres to the third transition and inhibits the epoxy from creeping into the third adjacent area. In some embodiments, the third adjacent area is configured to accept at least an excess portion of epoxy disposed within the first pocket, thereby preventing the epoxy from creeping into at least one of the first and second adjacent areas.

According to some embodiments, a method of fabricating an analyte sensing apparatus is provided. The method includes forming a housing. The housing includes a first pocket having a first pocket base, a first adjacent area abutting a first side of the first pocket, the first adjacent area having a first adjacent area base and a first transition between the first pocket base and the first adjacent area base, a second adjacent area abutting a second side of the first pocket, the second adjacent area having a second adjacent area base and a second transition between the first pocket base and the second adjacent area base, and a conductive contact disposed in the first adjacent area or in the second adjacent area. The method includes disposing an electronics assembly substrate within the housing and electrically coupling the electronics assembly substrate to the conductive contact. The method includes disposing an analyte sensor including at least one electrode in electrical communication with the conductive contact. The method includes disposing epoxy on the first pocket base, the epoxy securing at least a portion of the analyte sensor to the first pocket base.

In some embodiments, at least one of the first adjacent area base and the second adjacent area base are disposed at an elevated height compared to the first pocket base. In some embodiments, the epoxy forms an upward-inflecting meniscus at the at least one of the first and second transitions and the elevated height exceeds a height of the upward-inflecting meniscus. In some embodiments, at least one of the first adjacent area base and the second adjacent area base are disposed at a same height as the first pocket base. In some embodiments, at least one of the first adjacent area base and the second adjacent area base are disposed at a reduced height compared to the first pocket base. In some embodiments, the epoxy forms a downward-inflecting meniscus at the at least one of the first and second transitions. In some embodiments, the epoxy adheres to the at least one of the first and second transitions and inhibits the epoxy from creeping into the at least one of the first and second transitions.

According to some embodiments, a method of fabricating an analyte sensing apparatus is provided. The method includes forming a housing including an aperture that defines a cavity having a first portion and a second portion in the housing. The method includes disposing a first heat-sealable thermoplastic elastomer along a perimeter of the first portion of the cavity. The method includes disposing at least a portion of an analyte sensor within the first portion of the cavity. The method includes fitting a cap on or within the aperture and over the first portion of the cavity, the cap including a second heat-sealable thermoplastic elastomer along at least a portion of the cap disposed over a border between the first and second portions of the cavity. The method includes melting the first and second heat-sealable thermoplastic elastomers, thereby sealing the first portion of the cavity from moisture ingress.

In some embodiments, the border between the first and second portions of the cavity includes a portion of the first heat-sealable thermoplastic elastomer.

According to some embodiments, a method of fabricating an analyte sensing apparatus is provided. The method includes forming a housing including an aperture that defines a housing cavity in the housing. The method includes disposing a first conductive contact and a second conductive contact in the housing cavity. The method includes placing a first electrode of an analyte sensor on the first conductive contact. The method includes placing a second electrode of the analyte sensor on the second conductive contact. The method includes providing a cap. The cap includes a base and a sealing material including a first cavity and a second cavity. The method includes fitting the cap on or within the aperture such that the sealing material at least partially fill a void within the housing cavity and presses against the housing, the first cavity aligns over the first electrode and the first conductive contact, and the second cavity aligns over the second electrode and the second conductive contact.

In some embodiments, the method includes, before fitting the cap on or within the aperture, disposing a first conductive elastomeric puck in the first cavity, and disposing a second conductive elastomeric puck in the second cavity. The first conductive elastomeric puck is configured to press against the first electrode and the first conductive contact when the cap is fitted on or within the aperture, thereby securing the first electrode to the first conductive contact. The second conductive elastomeric puck is configured to press against the second electrode and the second conductive contact when the cap is fitted on or within the aperture, thereby securing the second electrode to the second conductive contact.

In some embodiments, the first and second conductive elastomeric pucks have a substantially cylindrical shape. In some embodiments, the base of the cap further includes at least a first hole that aligns laterally with the first cavity and a second hole that aligns laterally with the second cavity, at least a portion of the sealing material physically isolating the first hole from the first cavity and the second hole from the second cavity. In some embodiments, the method includes injecting conductive epoxy into the first cavity through the first hole and through the portion of the sealing material, thereby electrically connecting the first electrode to the first conductive contact and injecting conductive adhesive into the second cavity through the second hole and through the portion of the sealing material, thereby electrically connecting the second electrode to the second conductive contact. In some embodiments, the first and second cavities have a substantially conical shape.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The present embodiments now will be discussed in detail with an emphasis on highlighting the advantageous features. These embodiments are for illustrative purposes only and are not to scale, instead emphasizing the principles of the disclosure. These drawings include the following figures, in which like numerals indicate like parts:

FIG. 4A illustrates a schematic of a pre-connected analyte sensor, according to some embodiments;

FIG. 4B illustrates another schematic of a pre-connected analyte sensor, according to some embodiments;

FIG. 4C illustrates a layered view of a pre-connected analyte sensor, according to some embodiments;

FIG. 23 illustrates a plan view of several example geometries for the pockets of FIG. 22, according to some embodiments;

FIG. 24 illustrates a set of side views of an example step-up transition as would be viewed along the cut-lines A-A' in FIG. 22, an example flush transition as would be viewed along the cut-line B-B' in FIG. 22, and an example step-down transition as would be viewed along the cut-line C-C' in FIG. 22, according to some embodiments;

FIG. 25 illustrates another set of side views of the transitions of FIG. 24 as viewed along the cut-lines A-A', B-B' and C-C' in FIG. 24, according to some embodiments;

Like reference numerals refer to like elements throughout. Elements are not to scale unless otherwise noted.

DETAILED DESCRIPTION

Figure 1:
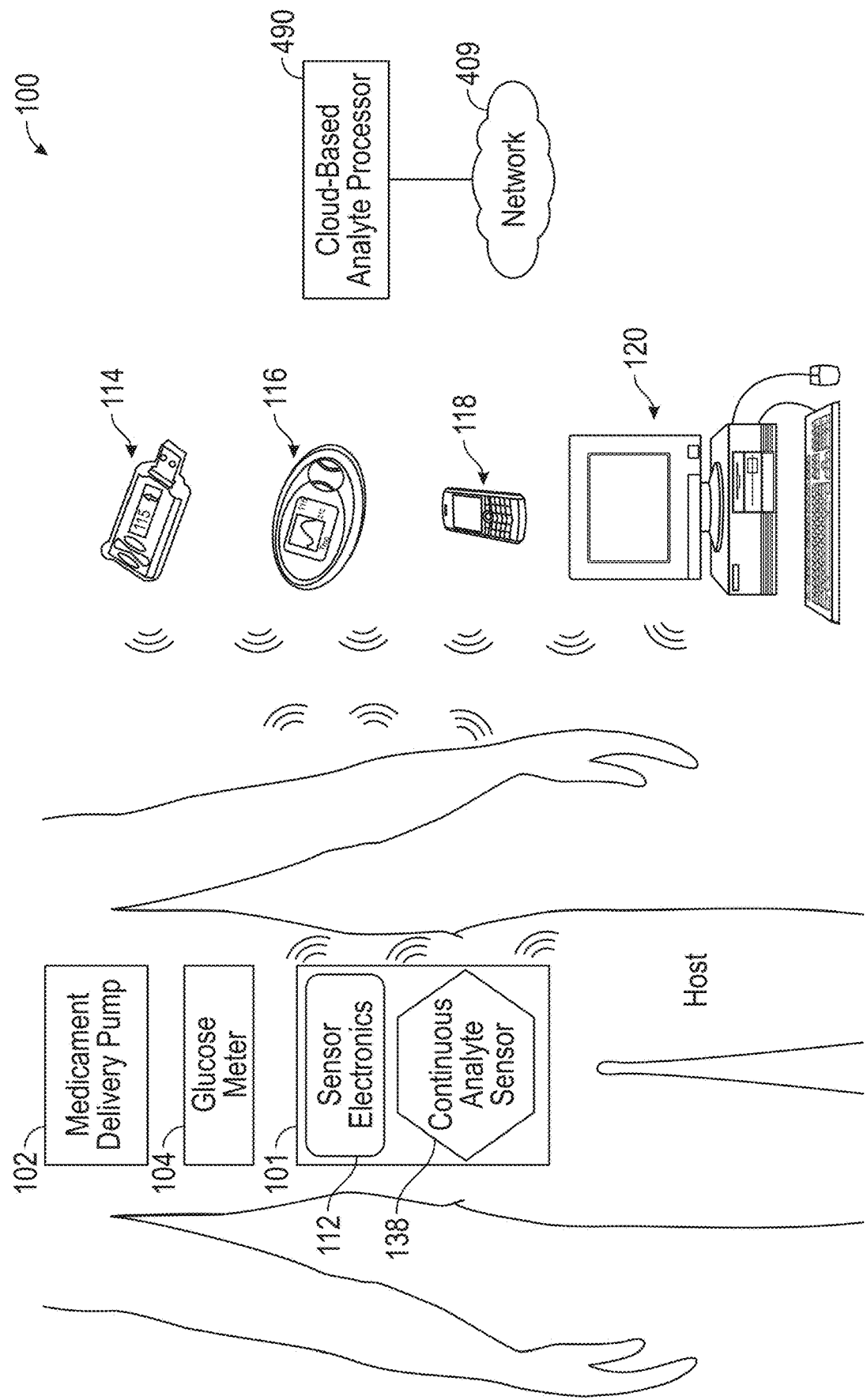
FIG. 1 is a schematic view of an analyte sensor system attached to a host and communicating with a plurality of example devices, according to some embodiments.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Definitions

In order to facilitate an understanding of the various embodiments described herein, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-13 hydroxy-cholic acid; cortisol; creatine kinase; creatine kinase MM isoenzyme; cyclosporin A; D-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, including by use of a sensitivity, to provide a meaningful value to a user.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified. A "lot" of sensors generally refers to a group of sensors that are manufactured on or around the same day and using the same processes and tools/materials. Additionally, sensors that measure temperature, pressure etc. may be referred to as a "sensor".

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like. Determining may also include ascertaining that a parameter matches a predetermined criterion, including that a threshold has been met, passed, exceeded, and so on.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signals directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "sensor electronics," as used herein, is a broad term, and is to be given its ordinary and customary meaning to a person of ordinary skill in the art (and is not to be limited to a special or customized meaning) and refers without limitation to the components (for example, hardware and/or software) of a device configured to process data. As described in further detail hereinafter (see, e.g., FIG. 2) "sensor electronics" may be arranged and configured to measure, convert, store, transmit, communicate, and/or retrieve sensor data associated with an analyte sensor.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., H2O2) associated with the measured analyte (e.g., glucose). For example, in one embodiment, a sensor has a sensitivity from about 1 to about 300 picoamps of current for every 1 mg/dL of glucose analyte.

The term "sample," as used herein, is a broad term, and is to be given its ordinary and customary meaning to a person of ordinary skill in the art (and it is not to be limited to a special or customized meaning), and refers without limitation to a sample of a host body, for example, body fluids, including, blood, serum, plasma, interstitial fluid, cerebral spinal fluid, lymph fluid, ocular fluid, saliva, oral fluid, urine, excretions, or exudates.

The term "distal to," as used herein, is a broad term, and is to be given its ordinary and customary meaning to a person of ordinary skill in the art (and is not to be limited to a special or customized meaning) and refers without limitation to the spatial relationship between various elements in comparison to a particular point of reference. In general, the term indicates an element is located relatively far from the reference point than another element.

The term "proximal to," as used herein, is a broad term, and is to be given its ordinary and customary meaning to a person of ordinary skill in the art (and is not to be limited to a special or customized meaning) and refers without limitation to the spatial relationship between various elements in comparison to a particular point of reference. In general, the term indicates an element is located relatively near to the reference point than another element.

The terms "electrical connection" and "electrical contact," as used herein, are broad terms, and are to be given their ordinary and customary meaning to a person of ordinary skill in the art (and are not to be limited to a special or customized meaning), and refer without limitation to any connection between two electrical conductors known to those in the art. In one embodiment, electrodes are in electrical connection with (e.g., electrically connected to) the electronic circuitry of a device. In another embodiment, two materials, such as but not limited to two metals, can be in electrical contact with each other, such that an electrical current can pass from one of the two materials to the other material and/or an electrical potential can be applied.

The term "elongated conductive body," as used herein, is a broad term, and is to be given its ordinary and customary meaning to a person of ordinary skill in the art (and is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire), an elongated conductive core coated with one, two, three, four, five, or more layers of material, each of which may or may not be conductive, or an elongated non-conductive core with conductive coatings, traces, and/or electrodes thereon and coated with one, two, three, four, five, or more layers of material, each of which may or may not be conductive.

The term "ex vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "in vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "potentiostat," as used herein, is a broad term, and is to be given its ordinary and customary meaning to a person of ordinary skill in the art (and is not to be limited to a special or customized meaning), and refers without limitation to an electronic instrument that controls the electrical potential between the working and reference electrodes at one or more preset values.

The term "processor module," as used herein, is a broad term, and is to be given its ordinary and customary meaning to a person of ordinary skill in the art (and are not to be limited to a special or customized meaning), and refers without limitation to a computer system, state machine, processor, components thereof, and the like designed to perform arithmetic or logic operations using logic circuitry that responds to and processes the basic instructions that drive a computer.

The term "sensor session," as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of (e.g., disconnection from) system electronics).

The terms "substantial" and "substantially," as used herein, are broad terms, and are to be given their ordinary and customary meaning to a person of ordinary skill in the art (and are not to be limited to a special or customized meaning) and refer without limitation to a sufficient amount that provides a desired function.

"Coaxial two conductor wire-based sensor": A round wire sensor consisting of a conductive center core, an insulating middle layer and a conductive outer layer with the conductive layers exposed at one end for electrical contact.

"Pre-connected sensor": A sensor that has a "sensor interconnect/interposer/sensor carrier" attached to it. Therefore this "Pre-connected sensor" comprises two parts that are joined: the sensor itself, and the interconnect/interposer/sensor carrier. The term "pre-connected sensor" unit refers to the unit that is formed by the permanent union of these two distinct parts.

Other definitions will be provided within the description below, and in some cases from the context of the term's usage.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade) ° F. (degrees Fahrenheit), Pa (Pascals), kPa (kiloPascals), MPa (megaPascals), GPa (gigaPascals), Psi (pounds per square inch), kPsi (kilopounds per square inch).

Overview/General Description of System

In vivo analyte sensing technology may rely on in vivo sensors. In vivo sensors may include an elongated conductive body having one or more electrodes such as a working electrode and a reference electrode.

For example, a platinum metal-clad, tantalum wire is sometimes used as a core bare sensing element with one or more reference or counter electrodes for an analyte sensor. This sensing element is coated in membranes to yield the final sensor.

Described herein, according to some embodiments, are pre-connected sensors that include an analyte sensor attached to a sensor carrier (also referred to herein as a "sensor interposer"). The analyte sensor may include a working electrode and a reference electrode at a distal end of an elongated conductive body. The sensor carrier may include a substrate, one or more electrical contacts coupled to one or more electrical contacts of the sensor, and circuitry such as one or more additional or external electrical contacts for coupling the one or more electrical contacts that are coupled to the sensor contact(s) to external equipment such as a membrane dip coating station, a testing station, a calibration station, or sensor electronics of a wearable device. In some embodiments, the substrate can be referred to as an intermediate body.

Further described herein, according to some other embodiments, are sensors, including a working electrode and a reference electrode at a distal end of an elongated conductive body, that are directly attached to a circuit board or substrate of a transmitter without the use of such an above-mentioned sensor carrier. Utilization of a sensor that is directly attached and/or electrically connected to a circuit board or substrate of a transmitter without the use of such above-mentioned sensor carriers can allow for a more streamlined manufacturing process that may comprise fewer steps and/or reduce manufacturing cost compared to embodiments utilizing a sensor that is pre-connected to a sensor carrier.

The following description and examples described the present embodiments with reference to the drawings. In the drawings, reference numbers label elements of the present embodiments. These reference numbers are reproduced below in connection with the discussion of the corresponding drawing features.

Sensor System

FIG. 1 depicts an example system 100, in accordance with some example implementations. The system 100 includes an analyte sensor system 101 including sensor electronics 112 and an analyte sensor 138. The system 100 may include other devices and/or sensors, such as medicament delivery pump 102 and glucose meter 104. The analyte sensor 138 may be physically connected to sensor electronics 112 and may be integral with (e.g., non-releasably attached to) or releasably attachable to the sensor electronics. For example, in some embodiments, continuous analyte sensor 138 may be connected to sensor electronics 112 via a sensor carrier that mechanically and electrically interfaces the analyte sensor 138 with the sensor electronics. In some other embodiments, continuous analyte sensor 138 may be directly connected to sensor electronics 112 without utilization of a sensor carrier that mechanically and electrically interfaces the analyte sensor 138 with the sensor electronics. The sensor electronics 112, medicament delivery pump 102, and/or glucose meter 104 may couple with one or more devices, such as display devices 114, 116, 118, and/or 120.

In some example implementations, the system 100 may include a cloud-based analyte processor 490 configured to analyze analyte data (and/or other patient-related data) provided via network 409 (e.g., via wired, wireless, or a combination thereof) from sensor system 101 and other devices, such as display devices 114, 116, 118, and/or 120 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, entitled "Cloud-Based Processing of Analyte Data" and filed on Mar. 7, 2013, published as U.S. Patent Application Publication 2013/0325352, herein incorporated by reference in its entirety. In some implementations, one or more steps of the factory calibration algorithm can be performed in the cloud.

In some example implementations, the sensor electronics 112 may include electronic circuitry associated with measuring and processing data generated by the analyte sensor 138. This generated analyte sensor data may also include algorithms, which can be used to process and calibrate the analyte sensor data, although these algorithms may be provided in other ways as well. The sensor electronics 112 may include hardware, firmware, software, or a combination thereof, to provide measurement of levels of the analyte via an analyte sensor, such as a glucose sensor. An example implementation of the sensor electronics 112 is described further below with respect to FIG. 2. In one implementation, the factory calibration algorithms described herein may be performed by the sensor electronics.

The sensor electronics 112 may, as noted, couple (e.g., wirelessly and the like) with one or more devices, such as display devices 114, 116, 118, and/or 120. The display devices 114, 116, 118, and/or 120 may be configured for presenting information (and/or alarming), such as sensor information transmitted by the sensor electronics 112 for display at the display devices 114, 116,118, and/or 120. In one implementation, the factory calibration algorithms described herein may be performed at least in part by the display devices.

In some example implementations, the relatively small, key fob-like display device 114 may comprise a wrist watch, a belt, a necklace, a pendent, a piece of jewelry, an adhesive patch, a pager, a key fob, a plastic card (e.g., credit card), an identification (ID) card, and/or the like. This small display device 114 may include a relatively small display (e.g., smaller than the large display device 116) and may be configured to display certain types of displayable sensor information, such as a numerical value, and an arrow, or a color code.

In some example implementations, the relatively large, hand-held display device 116 may comprise a hand-held receiver device, a palm-top computer, and/or the like. This large display device may include a relatively larger display (e.g., larger than the small display device 114) and may be configured to display information, such as a graphical representation of the sensor data including current and historic sensor data output by sensor system 100.

In some example implementations, the analyte sensor 138 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the analyte sensor 138 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the analyte sensor 138 may be implanted as at least one of the following types of analyte sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include an analyte sensor 138 comprising a glucose sensor, the analyte sensor 138 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

In some manufacturing systems, sensors 138 are manually sorted, placed and held in fixtures. These fixtures are manually moved from station to station during manufacturing for various process steps including interfacing electrical measurement equipment for testing and calibration operations. However, manual handling of sensors can be inefficient, can cause delays due to non-ideal mechanical and electrical connections, and can risk damage to the sensor and/or testing and calibration equipment and can induce sensor variability that can lead to inaccurate verification data being collected in manufacturing. In addition, the process of packaging sensor 138 with the sensor electronics 112 into a wearable device involves further manual manipulation of the sensor that can damage sensor 138.

Identification and other data associated with each sensor may be stored on the sensor carrier, if utilized, for logging and tracking of each sensor during manufacturing, testing, calibration, and in vivo operations. Following testing and calibration operations, the sensor carrier may be used to connect the sensor to sensor electronics of a wearable device, such as an on-skin sensor assembly, in an arrangement that is sealed and electrically robust. In embodiment not incorporating such a sensor carrier, the sensor may be directly connected to the sensor electronics (e.g. to the printed circuit board of the sensor electronics) of the wearable device.

Figure 2:
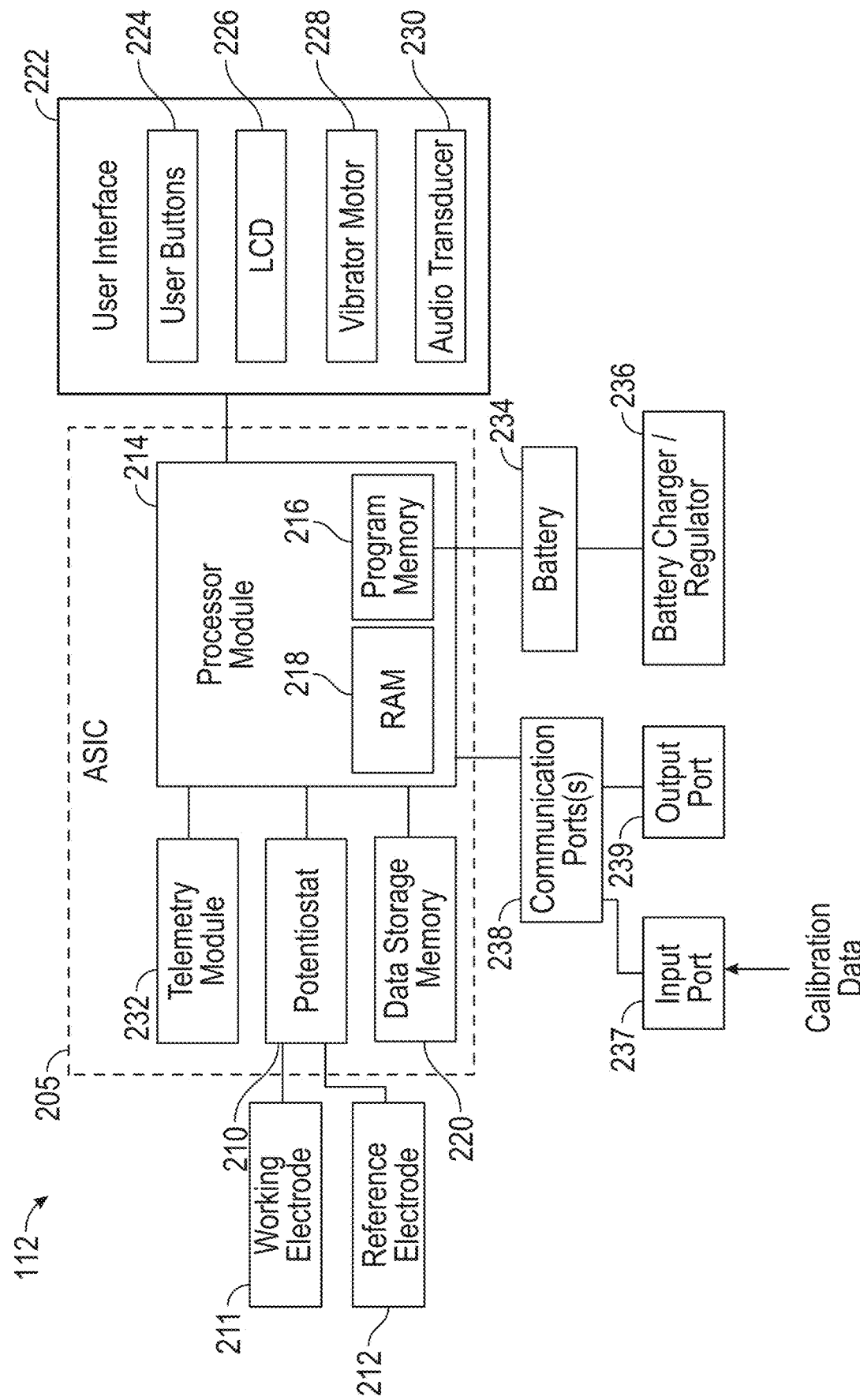
FIG. 2 is a block diagram that illustrates electronics associated with the sensor system of FIG. 1, according to some embodiments.

FIG. 2 depicts an example of electronics 112 that may be used in sensor electronics 112 or may be implemented in a manufacturing station such as a testing station, a calibration station, a smart carrier, or other equipment used during manufacturing of device 101, in accordance with some example implementations. The sensor electronics 112 may include electronics components that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by factory calibration algorithms as disclosed herein, smoothing and/or filtering algorithms of sensor data, and/or the like.

In some embodiments, a processor module 214 is configured to achieve a substantial portion, if not all, of the data processing, including data processing pertaining to factory calibration. Processor module 214 may be integral to sensor electronics 112 and/or may be located remotely, such as in one or more of devices 114, 116, 118, and/or 120 and/or cloud 490. For example, in some embodiments, processor module 214 may be located at least partially within a cloud-based analyte processor 490 or elsewhere in network 409.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 114, 116, 118, and/or 120, to enable calibration of the sensor data from sensor 138. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a factory calibration, as described below.

In some example implementations, the sensor electronics 112 may comprise an application-specific integrated circuit (ASIC) 205 coupled to a user interface 222. The ASIC 205 may further include a potentiostat 210, a telemetry module 232 for transmitting data from the sensor electronics 112 to one or more devices, such as devices 114, 116, 118, and/or 120, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 2, through a first input port 211 for sensor data the potentiostat 210 is coupled to an analyte sensor 138, such as a glucose sensor to generate sensor data from the analyte. The potentiostat 210 may be coupled to a working electrode 211 and reference electrode 212 that form a part of sensor 138. The potentiostat may provide a voltage to one of the electrodes 211, 212 of analyte sensor 138 to bias the sensor for measurement of a value (e.g., a current) indicative of the analyte concentration in a host (also referred to as the analog portion of the sensor). The potentiostat 210 may have one or more connections to sensor 138 depending on the number of electrodes incorporated into the analyte sensor 138 (such as a counter electrode as a third electrode).

In some example implementations, the potentiostat 210 may include a resistor that translates a current value from sensor 138 into a voltage value, while in some example implementations, a current-to-frequency converter (not shown) may also be configured to integrate continuously a measured current value from sensor 138 using, for example, a charge-counting device. In some example implementations, an analog-to-digital converter (not shown) may digitize the analog signal from sensor 138 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 112 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although Bluetooth technology may also be implemented in a combination of the telemetry module 232 and the processor module 214.

The processor module 214 may control the processing performed by the sensor electronics 112. For example, the processor module 214 may be configured to process data (e.g., counts), from the sensor, filter the data, calibrate the data, perform fail-safe checking, and/or the like.

Potentiostat 210 may measure the analyte (e.g., glucose and/or the like) at discrete time intervals or continuously, for example, using a current-to-voltage or current-to-frequency converter.

The processor module 214 may further include a data generator (not shown) configured to generate data packages for transmission to devices, such as the display devices 114, 116, 118, and/or 120. Furthermore, the processor module 214 may generate data packets for transmission to these outside sources via telemetry module 232. In some example implementations, the data packages may include an identifier code for the sensor and/or sensor electronics 112, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 112 and/or charge the battery 234.

The program memory 216 may be implemented as a semi-static memory for storing data, such as an identifier for a coupled sensor 138 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods described below, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, electrically erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of analyte sensor data. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host).

The battery 234 may be operatively connected to the processor module 214 (and possibly other components of the sensor electronics 12) and provide the necessary power for the sensor electronics 112. In other implementations, the receiver can be transcutaneously powered via an inductive coupling, for example.

A battery charger and/or regulator 236 may be configured to receive energy from an internal and/or external charger. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 112. The communication port, for example, may comprise a serial (e.g., universal serial bus or "USB") communication port, and allow for communicating with another computer system (e.g., PC, personal digital assistant or "PDA," server, or the like). In some example implementations, factory information may be sent to the algorithm from the sensor or from a cloud data source.

The one or more communication ports 238 may further include an input port 237 in which calibration data may be received, and an output port 239 which may be employed to transmit calibrated data, or data to be calibrated, to a receiver or mobile device. FIG. 2 illustrates these aspects schematically. It will be understood that the ports may be separated physically, but in alternative implementations a single communication port may provide the functions of both the second input port and the output port.

In some analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 112 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Figure 3A:
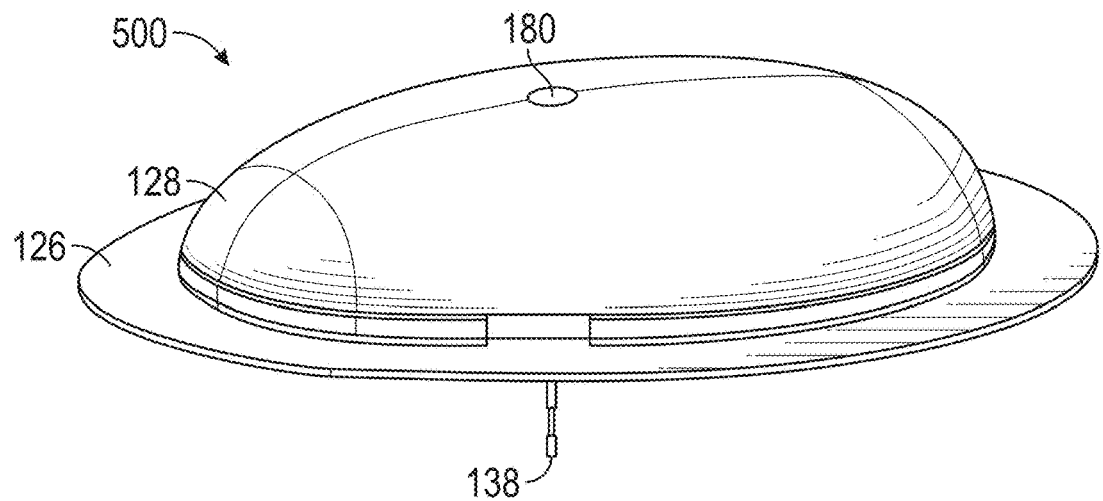
FIGS. 3A-3C illustrate a wearable device having an analyte sensor, according to some embodiments.
Figure 3B:
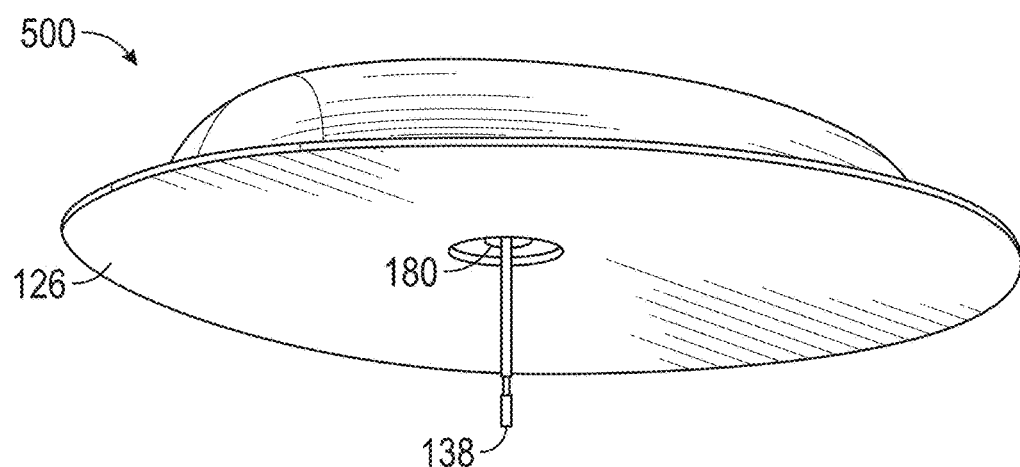
Figure 3C:
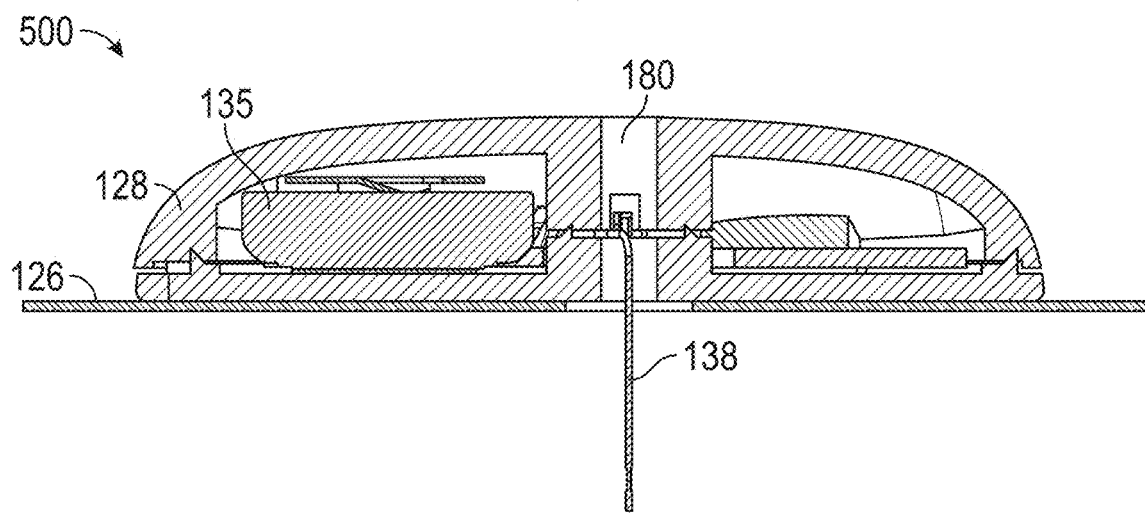

FIGS. 3A, 3B, and 3C illustrate an exemplary implementation of analyte sensor system 101 implemented as a wearable device such as an on-skin sensor assembly 500, 600. As shown in FIG. 3, on-skin sensor assembly comprises a housing 128. An adhesive patch 126 can couple the housing 128 to the skin of the host. The adhesive 126 can be a pressure sensitive adhesive (e.g. acrylic, rubber based, or other suitable type) bonded to a carrier substrate (e.g., spun lace polyester, polyurethane film, or other suitable type) for skin attachment. The housing 128 may include a through-hole 180 that cooperates with a sensor inserter device (e.g., a sensor insertion needle, not shown) that is used for implanting sensor 138 under the skin of a subject.

The wearable sensor assembly 500, 600 can include sensor electronics 112 (e.g., as at least a portion of electronics module 135) operable to measure and/or analyze glucose indicators sensed by glucose sensor 138. Sensor electronics 112 within sensor assembly 500, 600 can transmit information (e.g., measurements, analyte data, and glucose data) to a remotely located device (e.g., 114, 116, 118, 120 shown in FIG. 1). As shown in FIG. 3C, in this implementation sensor 138 extends from its distal end up into through-hole 180 and is routed to an electronics module 135 inside the enclosure 128. The working electrode 211 and reference electrode 212 are connected to circuitry in the electronics module 135 which includes the potentiostat.

Figure 3D:
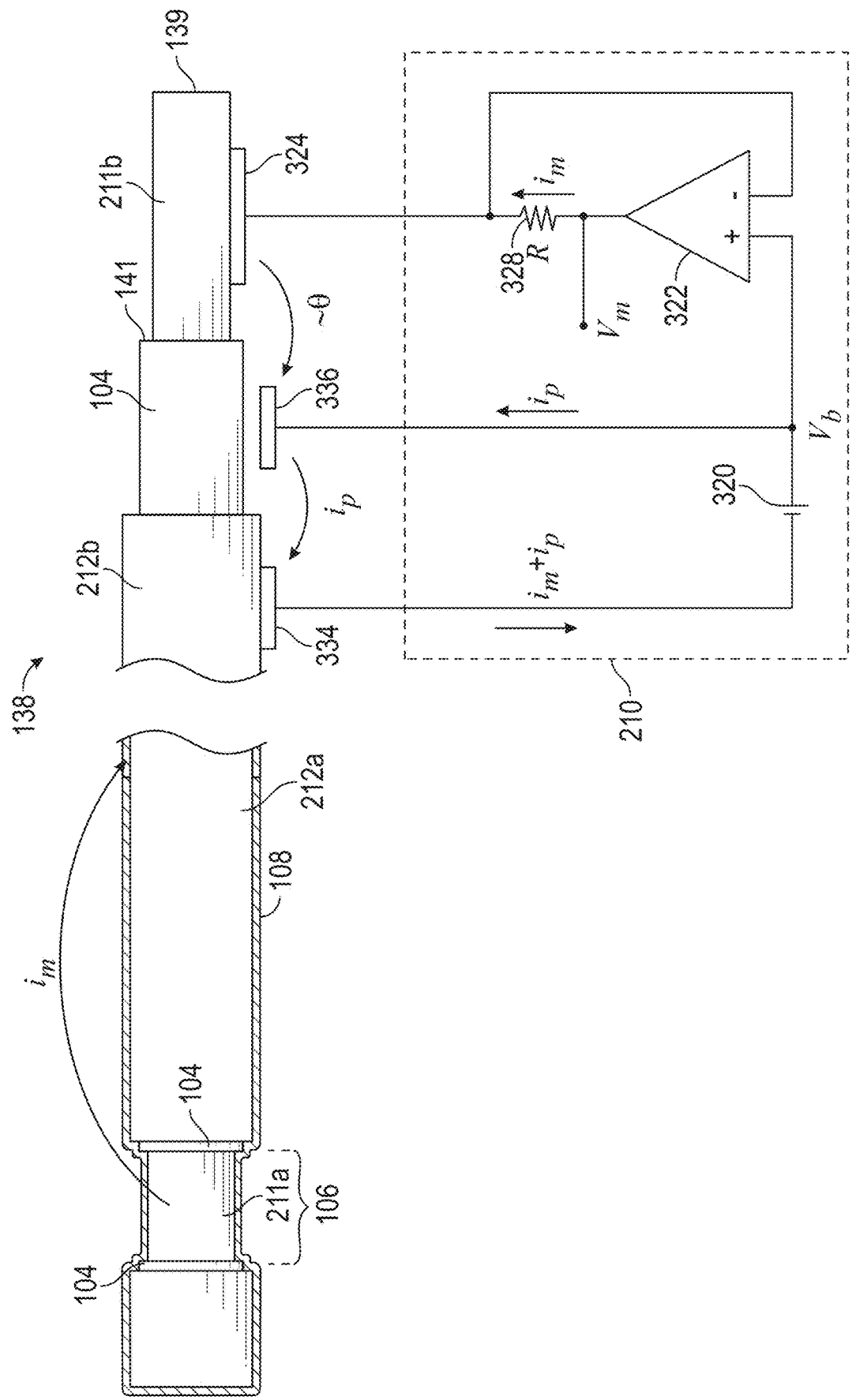
FIG. 3D illustrates one implementation of an elongated sensor connected to a potentiostat.

FIG. 3D illustrates one exemplary embodiment of an analyte sensor 138 which includes an elongated body portion. The elongated body portion may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated herein as having a circular cross-section, in other embodiments the cross-section of the elongated conductive body can be ovoid, rectangular, triangular, or polyhedral, star-shaped, C-shaped, T-shaped, X-shaped, Y-shaped, irregular, or the like.

In the implementation of FIG. 3D, the analyte sensor 138 comprises a wire core 139. At a distal, in vivo portion of sensor 138, the wire core 139 forms an electrode 211$a$. At a proximal, ex vivo portion of sensor 138, the wire core 139 forms a contact 211$b$. The electrode 211$a$ and the contact 211$b$ are in electrical communication over the length of the wire core 139 as it extends along the elongated body portion of sensor 138. The wire core can be made from a single material such as platinum or tantalum, or may be formed as multiple layers, such as a conducting or non-conducting material with an outer coating of a different conducting material.

A layer 104 surrounds a least a portion of the wire core 139. The layer 104 may be formed of an insulating material, such as polyimide, polyurethane, parylene, or any other known insulating materials. For example, in one embodiment the layer 104 is disposed on the wire core 139 and configured such that the electrode 211$a$ is exposed via window 106.

In some embodiments, sensor 138 further comprises a layer 141 surrounding the insulating layer 104 like a sleeve that comprises a conductive material. At a distal, in vivo portion of sensor 138, the sleeve layer 141 forms an electrode 212$a$. At a proximal, ex vivo portion of sensor 138, the sleeve layer 141 forms a contact 212$b$. The electrode 212$a$ and the contact 212$b$ are in electrical communication over the length of the sleeve layer 141 as it extends along the elongated body portion of sensor 138. This sleeve layer 141 may be formed of a silver-containing material that is applied onto the insulating layer 104. The silver-containing material may include any of a variety of materials and be in various forms, such as, Ag/AgCl-polymer pastes, paints, polymer-based conducting mixture, and/or inks that are commercially available, for example. This layer 141 can be processed using a pasting/dipping/coating step, for example, using a die-metered dip coating process. In one exemplary embodiment, an Ag/AgCl polymer paste is applied to an elongated body by dip—coating the body (e.g., using a meniscus coating technique) and then drawing the body through a die to meter the coating to a precise thickness. In some embodiments, multiple coating steps are used to build up the coating to a predetermined thickness.

Sensor 138 shown in FIG. 3D also includes a membrane 108 covering at least a portion of the distal in vivo portion of sensor 138. This membrane is typically formed of multiple layers, which may include one or more of an interference domain, an enzyme domain, a diffusion resistance domain, and a bioprotective domain. This membrane is important to support the electrochemical processes that allow analyte detection and it is generally manufactured with great care by dip-coating, spraying, or other manufacturing steps. It is preferable for the distal in vivo portion of sensor 138 to be subject to as little handling as possible or practical from the time the membrane 108 is formed to the time the distal in vivo portion of sensor 138 is implanted into a subject. In some embodiments, electrode 211$a$ forms a working electrode of an electrochemical measuring system, and electrode 212$a$ forms a reference electrode for that system. In use, both electrodes may be implanted into a host for analyte monitoring.

Although the above description is applicable specifically to a coaxial wire type structure, the embodiments herein are also applicable to other physical configurations of electrodes. For example, the two electrodes 211$a$ and 212$a$ could be affixed to a distal in vivo portion of an elongated flexible strip of a planar substrate such as a thin, flat, polymer flex circuit. The two contacts 211$b$ and 212$b$ could be affixed to the proximal ex vivo portion of this flexible planar substrate. Electrodes 211$a$, 212$a$ could be electrically connected to their respective contacts 211$b$, 212$b$ via circuit traces on the planar substrate. In this case, the electrodes 211$a$ and 212$a$ and the contacts 211$b$ and 212$b$ may be adjacent to one another on a flat surface rather than being coaxial as shown in FIG. 3D.

In some other embodiments, the two contacts 211$b$ and 212$b$ may be coupled directly to one or more contacts and/or traces of sensor electronics 112 (see FIGS. 1 and 2) without utilization of such an above-mentioned flexible strip of planar substrate, as will be described in more detail in the following description.

Also shown in FIG. 3D is an illustration of the contact 211$b$ and the contact 212$b$ electrically coupled to a simple current-to-voltage converter based potentiostat 210. The potentiostat includes a battery 320 that has an output coupled to an input of an operational amplifier 322. The output of the operational amplifier 322 is coupled to a contact 324 that is electrically coupled to the working electrode contact 211$b$ through a resistor 328. The amplifier 322 will bias the contact 324 to the battery voltage $V_b$, and will drive the current $i_m$ required to maintain that bias. This current will flow from the working electrode 211$a$ through the interstitial fluid surrounding sensor 138 and to the reference electrode 212$a$. The reference electrode contact 212$b$ is electrically coupled to another contact 334 which is connected to the other side of the battery 320. For this circuit, the current $i_m$ is equal to $(V_b - V_m)/R$, where $V_m$ is the voltage measured at the output of the amplifier 322. The magnitude of this current for a given bias on the working electrode 211$a$ is a measure of analyte concentration in the vicinity of the window 106.

The contacts 324 and 334 are typically conductive pads/traces on a circuit board. There is always some level of parasitic leakage current $i_p$ over the surface of this board during the test. If possible, this leakage current should not form part of the measurement of current due to analyte. To reduce the effect this leakage current has on the measured current, an optional additional pad/trace 336 may be provided between the biased contact 324 and the return contact 334 that is connected directly to the battery output. This optional additional pad/trace may be referred to as a "guard trace." Because they are held at the same potential, there will be essentially no leakage current from the biased contact 324 and the guard trace 336. Furthermore, leakage current from the guard trace 336 to the return contact 334 does not pass through the amplifier output resistor 328, and therefore is not included in the measurement. Additional aspects and implementations of a guard trace may be found in paragraphs [0128] and [0129] of U.S. Patent Publication 2017/0281092, which are incorporated herein by reference.

During manufacturing, various coating, testing, calibration, and assembly operations are performed on sensor 138. However, it can be difficult to transport individual sensors and electrically interface the sensors with multiple testing and calibration equipment installations. These processes can also subject the sensors to damage from handling. To help address these issues, sensor 138 may be provided as a part of a pre-connected sensor that includes a sensor carrier as described in greater detail below in connection with at least FIGS. 4A-4D and 5A-5C.

However, such pre-connected sensor embodiments may require additional manufacturing steps, which can undesirably increase manufacturing cost. Accordingly, in some other embodiments, at least a portion of sensor 138, for example, contacts 211b and 212b may be coupled directly to one or more contacts and/or traces of sensor electronics 112 (e.g., at least a portion of electronics module 135, see FIGS. 1 and 2) without utilization of a sensor carrier, as will be described in greater detail below in connection with at least FIGS. 6A-6C, thereby reducing a number of manufacturing steps and decreasing manufacturing complexity and/or cost.

Sensors Pre-Connected to a Sensor Carrier

FIG. 4A shows a schematic illustration of a pre-connected sensor 400. As shown in FIG. 4A, pre-connected sensor 400 includes sensor carrier 402 permanently attached to sensor 138. In the example of FIG. 4A, sensor carrier 402 includes an intermediate body such as substrate 404, and also includes one or more contacts such as first internal contact 406, and second internal contact 408. First internal contact 406 is electrically coupled to a first contact on a proximal end of sensor 138 and contact internal 408 is electrically coupled to a second contact on the proximal end of sensor 138. The distal end of sensor 138 is a free end configured for insertion into the skin of the host. Contacts 406 and 408 may, for example, correspond to contacts 324 and 334 of FIG. 3D in some implementations.

As shown in FIG. 4A, first internal contact 406 may be electrically coupled to a first external contact 410 and second internal contact 408 may be electrically coupled to a second external contact 412. As described in further detail hereinafter, external contacts 410 and 412 may be configured to electrically interface with sensor electronics 112 in a wearable device 500 (see FIGS. 5A-5C). Furthermore, external contacts 410 and 412 may be configured to electrically interface with processing circuitry of manufacturing equipment such as one or more testing stations and/or one or more calibration stations. Although various examples are described herein in which two external contacts 410 and 412 on the sensor carrier are coupled to two corresponding contacts on sensor 138, this is merely illustrative. In other implementations, sensor carrier 402 and sensor 138 may each be provided with a single contact or may each be provided with more than two contacts, for example, any number N of external contacts (e.g., more than two external contacts 410 and 412) of the sensor carrier and any number M of contacts (e.g., more than two contacts 406 and 408) of sensor 138 that can be coupled. In some implementations, sensor carrier 402 and sensor 138 may have the same number of contacts (i.e., N=M). In some implementations, sensor carrier 402 and sensor 138 may have a different number of contacts (i.e., N≠M). For example, in some implementations, sensor carrier 402 may have additional contacts for coupling to or between various components of a manufacturing station.

As described in further detail hereinafter, substrate 404 may be configured to couple with sensor electronics 112 in wearable device 500. In some embodiments, substrate 404 may be sized and shaped to mechanically interface with housing 128 and electrically interface with sensor electronics 112 inside housing 128. Further, substrate 404 may be sized and shaped to mechanically interface with manufacturing equipment, assembly equipment, testing stations and/or one or more calibration stations. As described in further detail hereinafter, sensor carrier 402 may be attached and/or electrically coupled to sensor 138. Sensor 138 may be permanently coupled to a component of sensor carrier 402 (e.g. substrate 404) by using, for example, adhesive (e.g. UV cure, moisture cure, multi part activated, heat cure, hot melt, etc.), including conductive adhesive (e.g. carbon filled, carbon nanotube filled, silver filled, conductive additive, etc.), conductive ink, spring contacts, clips, wrapped flexible circuitry, a conductive polymer (e.g. conductive elastomer, conductive plastic, carbon filled PLA, conductive graphene PLA), conductive foam, conductive fabric, a barrel connector, a molded interconnect device structure, sewing, wire wrapping, wire bonding, wire threading, spot welding, swaging, crimping, stapling, clipping, soldering or brazing, plastic welding, or overmolding. In some embodiments, sensor 138 may be permanently coupled to substrate 404 by rivets, magnets, anisotropic conductive films, metallic foils, or other suitable structures or materials for mechanically and electrically attaching sensor carrier 402 to sensor 138 before or during assembly, manufacturing, testing and/or calibration operations. While the above-described attachment techniques for sensor 138 are described in connection with the use of sensor carrier 402, the present disclosure also contemplated the use of any of the above-described techniques for attaching sensor 138 directly to an electronics assembly substrate, for example electronics assembly substrate 630 as will be described in more detail in connection with FIGS. 6A-6C below.

In some embodiments, sensor carrier 402 may be 3-D printed around sensor 138 to form pre-connected sensor 400. Additionally, sensor carrier 402 may include datum features 430 (sometimes referred to as datum structures) such as a recess, an opening, a surface or a protrusion for aligning, positioning, and orienting sensor 138 relative to sensor carrier 402. Sensor carrier 402 may also include, or may itself form, one or more anchoring features for securing and aligning the analyte sensor during manufacturing (e.g., relative to a manufacturing station). Additionally, sensor carrier 402 may include an identifier 450 configured to identify the sensor. In some embodiments, identifier 450 is formed on substrate 404. Identifier 450 will be explained further below.

FIG. 4B illustrates another schematic of a pre-connected analyte sensor 400. The pre-connected analyte sensor 400 shown in FIG. 4B may include similar components of pre-connected analyte sensor 400 shown in FIG. 4A. FIG. 4B is shown without optional cover 460 for clarity. FIG. 4C illustrated an exploded view of pre-connected analyte sensor 400 shown in FIG. 4B.

In the example of FIG. 4B, sensor carrier 402 includes an intermediate body such as a substrate 404, and also includes one or more traces such as first trace 414 and second trace 416. First trace 414 may include a first internal contact 406 and a first external contact 410. Second trace 416 may include a second internal contact 408 and a second external contact 412. In some embodiments, first internal contact 406 is electrically coupled to a first contact on a proximal end of sensor 138 and second internal contact 408 is electrically coupled to a second contact on the proximal end of sensor 138. The distal end of sensor 138 is a free end configured for insertion into the skin of the host. The electrical coupling may comprise clips, conductive adhesive, conductive polymer, conductive ink, metallic foil, conductive foam, conductive fabric, wire wrapping, wire threading or any other suitable method. In some embodiments, a non-conductive adhesive 426 (e.g. epoxy, cyanoacrylate, acrylic, rubber, urethane, hot melt, etc.) can be used to attach sensor 138 to substrate 404. Non-conductive adhesive 426 may be configured to affix, seal, insulate, or provide a strain relief to sensor 138. Sensor 138 may be attached to substrate 404 by other methods, such as those described in FIG. 4A above.

As shown in FIG. 4C, a pressure sensitive adhesive 428 may be configured to isolate an exposed end of traces 414 and 416. For instance, pressure sensitive adhesive 428 may laminate sensor 138 between substrate 404 and cover 460. In such instances, sensor 138, substrate 404, pressure sensitive adhesive 428, and cover 460 may form a laminated configuration. In the laminated configuration, sensor 138 and its connection to one or more contacts (e.g. first internal contact 406 and second internal contact 408) are isolated from one or more exposed contacts (e.g. first external contact 410 and second external contact 412). Furthermore, the laminated configuration may create a moisture sealed region surrounding sensor 138. The moisture seal may be created as embodied by a combination of a pressure sensitive adhesive 428 and a non-conductive adhesive 426. In other embodiments, the laminated structure can be created by one or a combination of the following materials and methods: a non-conductive adhesive, a pressure sensitive adhesive tape, an elastomer, heat bonding, hot plate welding, laser welding, ultrasonic welding, RF welding, or any suitable type of lamination method. The cover 460 may consist of a polymer sheet, structure, or film that at least partially covers the substrate 404. The cover 460 may optionally contain an identifier 450, which can identify sensor 138. In some embodiments, identifier 450 may incorporate various identification protocols or techniques such as, but not limited to, NFC, RFID, QR Code, Bar code, Wi-Fi, Trimmed resistor, Capacitive value, Impedance values, ROM, Memory, IC, Flash memory, etc.

Guide fixture 420, which is an optional component, is an exemplary embodiment of an interface with a work station, such as a testing station, a calibration station, an assembly station, a coating station, manufacturing stations, or as part of the wearable assembly. The guide fixture 420 includes datum features (or datum structures) 430, such as a recess, an opening, a surface or a protrusion for aligning, positioning, and orienting sensor 138 relative to sensor carrier 402. Datum features 430 may be used in manufacturing and for assembly into a wearable electronic component. In some embodiments, datum features 430 are raised protrusions configured to align with corresponding datum features 432 of substrate 404. Corresponding datum features 432 of substrate 404 may feature cutouts, slots, holes, or recesses. The corresponding datum features 432 in the sensor carrier may be placement features that can interface with datum features 430 in a work station, such as a testing station, a calibration station, an assembly station, a coating station, or other manufacturing stations. Guide fixture 420 may be configured to ensure proper placement of the sensor carrier 402 to align the exposed external contacts 410 and 412 for connecting to a work station, such as a testing station, a calibration station, an assembly station, a coating station, or other manufacturing stations. In other embodiments, datum features 430 may consist of female features to engage with male corresponding datum features 432.

Figure 4D:
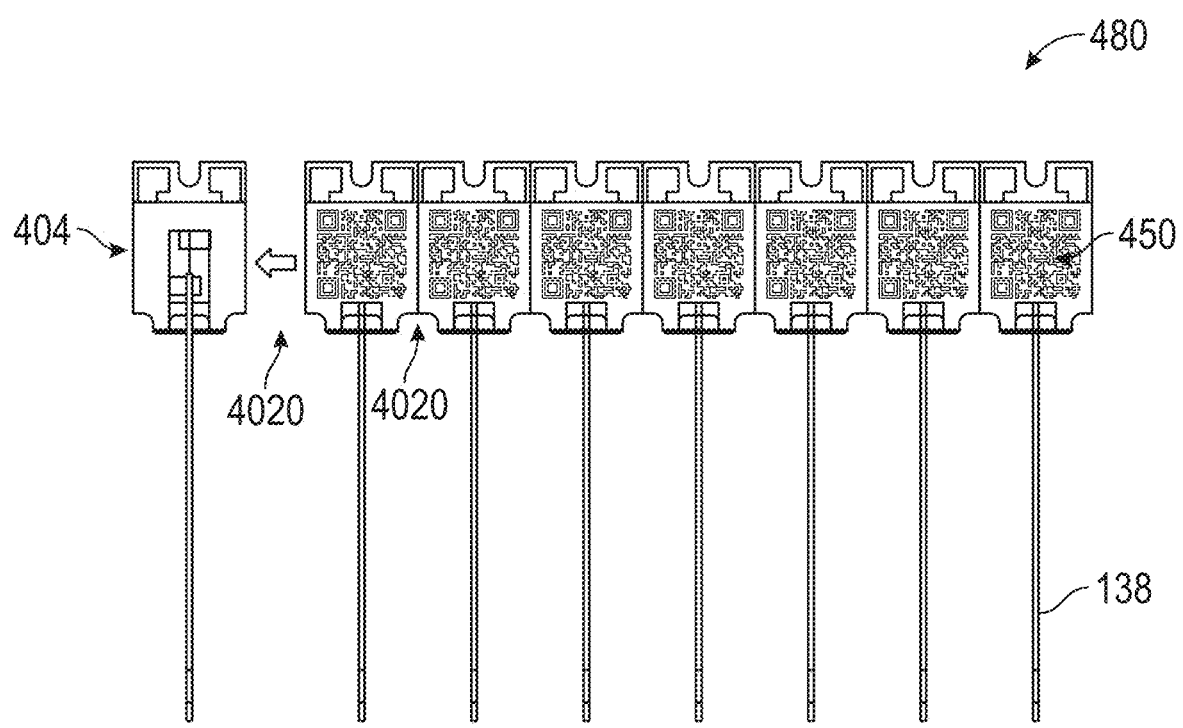
FIG. 4D illustrates a schematic view of an array of pre-connected analyte sensors, according to some embodiments.

FIG. 4D illustrates a schematic view of an array 480 of pre-connected analyte sensors 400 having a plurality of pre-connected sensors 400 with optional identifiers 450. In FIG. 4D, an array formed as a one-dimensional strip of pre-connected analyte sensors 400 is shown, but a two-dimensional array could also be implanted. In some embodiments, the array 480 of pre-connected analyte sensors may be disposed in a cartridge. Each of the plurality of pre-connected sensors 400 can be singulated. In some embodiments, scoring 4020 may be provided to facilitate singulation into individual pre-connected sensors 400. In some embodiments, the array 480 can be used in facilitating manufacturing, testing and/or calibrating multiple sensors 138 individually in sequential or random manners. In some embodiments, the array 480 can be used in facilitating manufacturing, testing and/or calibrating multiple sensors 138 concurrently.

Figure 5A:
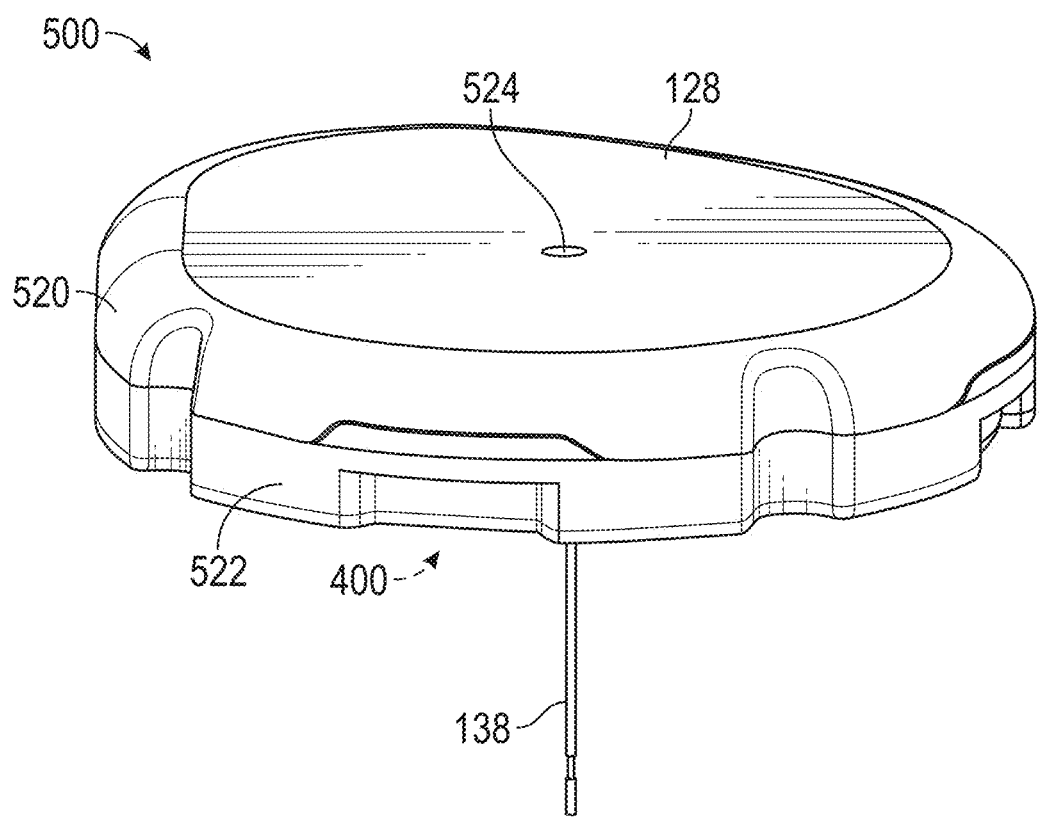
FIGS. 5A-5B illustrate perspective views of a wearable sensor assembly, according to some embodiments.
Figure 5B:
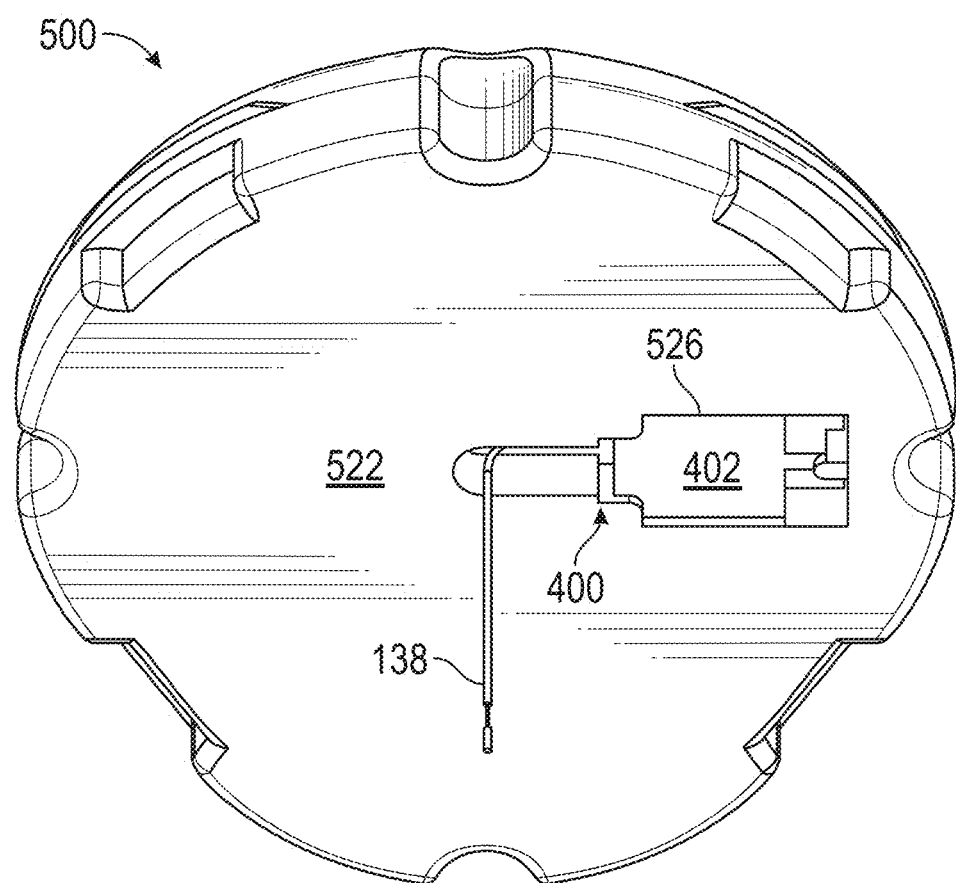

FIGS. 5A and 5B show perspective views of an embodiment of a wearable assembly 500 including a pre-connected sensor 400. Wearable assembly 500 may include sensor electronics and an adhesive patch (not shown). Pre-connected sensor 400 may include a sensor carrier such as sensor carrier 402 described in FIGS. 4A-4D. The sensor carrier 402 may be placed in or on housing 128. Housing 128 may be composed of two housing components, top housing 520 and bottom housing 522. Top housing 520 and bottom housing 522 can be assembled together to form housing 128. Top housing 520 and bottom housing 522 can be sealed to prevent moisture ingress to an internal cavity of housing 128. The sealed housing may include an encapsulating material (e.g. epoxy, silicone, urethane, or other suitable material). In other embodiments, housing 128 is formed as a single component encapsulant (e.g. epoxy) configured to contain sensor carrier 402 and sensor electronics. FIG. 5A illustrates an aperture 524 within top housing 520 configured to allow for an insertion component (e.g. hypodermic needle, C-needle, V-needle, open sided needle, etc.) to pass through the wearable assembly 500 for insertion and/or retraction. Aperture 524 may be aligned with a corresponding aperture in bottom housing 522. In other embodiments, aperture 524 may extend through an off-center location of housing 128. In other embodiments, aperture 524 may extend through an edge of the housing 128, forming a C-shaped channel. In some embodiments the aperture 524 includes a sealing material such as a gel, adhesive, elastomer, or other suitable material located within aperture 524.

FIG. 5B shows a perspective view of the bottom of wearable assembly 500. As illustrated, pre-connected sensor 400 may be disposed within the housing 128. Pre-connected sensor 400 may be installed within an aperture 526 (sometimes referred to as an opening, a cavity, a void, a space or a pocket) of bottom housing 522. As shown in the figure, sensor 138 may extend out from aperture 526. Aperture 526 may be sized and shaped to retain pre-connected sensor 400. Furthermore, aperture 526 may be sized and shaped to retain pre-connected sensor 400 in which sensor 138 extends approximately parallel to the skin surface and forms a 90-degree bend for insertion into the skin. It should be understood that the bottom surface of bottom housing 522 can contain an attachment member (e.g. an adhesive patch) for adhering the wearable assembly to the skin surface of a user.

Figure 5C:
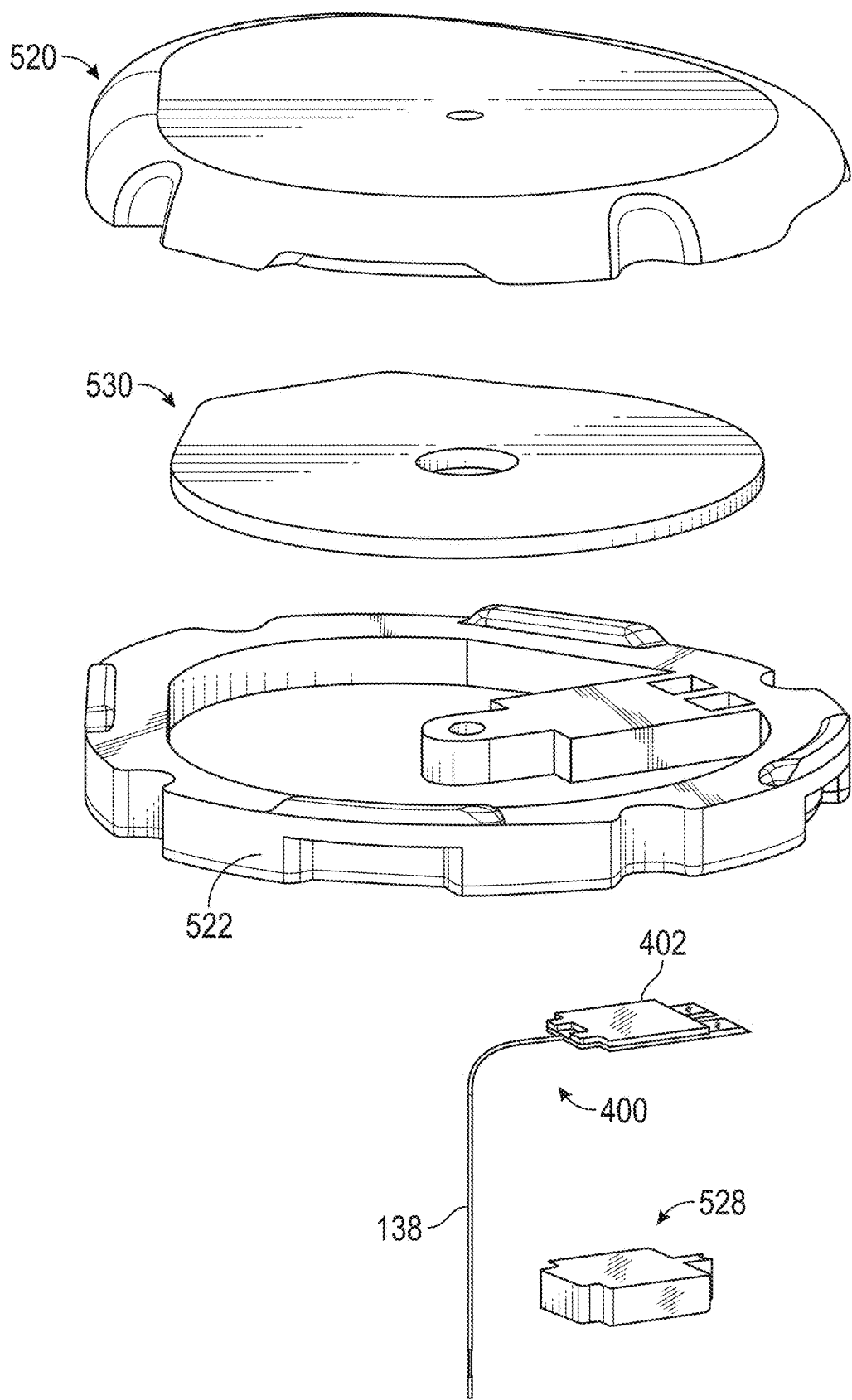
FIG. 5C illustrates an exploded view of components of a wearable sensor assembly, according to some embodiments.

FIG. 5C shows an exploded view of the wearable assembly 500. Various electronic components such as the potentiostat 210 and other components illustrated in FIG. 2 may be mounted on or to an electronics assembly substrate 530, typically some form of printed circuit board. It is contemplated that sensor carrier 402 has an electrical coupling with electronics assembly substrate 530. Various methods may be used to establish electrical connection (e.g. pins, solder, conductive elastomer, conductive adhesive, etc.) between one or more contacts of pre-connected sensor 400, such as external contacts 410 and 412 and electronics assembly substrate 530. Sensor carrier 402 may be configured to interface with electronics assembly substrate 530 through the bottom housing 522. In other implementations, the sensor carrier 402 may be configured to interface with the electronics assembly substrate 530 through top housing 520. In some other implementations, the sensor carrier 402 is configured to interface with the electronics assembly substrate 530 through the side of wearable assembly 500. Also shown in the figure, an optional sealing member 528 may be configured to insulate at least a portion of sensor carrier 402 from potential moisture ingress. In some instances, the sealing member 528 may be liquid dispensed (e.g., adhesive, gel) or a solid material (e.g., elastomer, polymer). The sealing member 528 may be an assembled component that is welded (e.g., laser or ultrasonic, hot plate), or otherwise permanently attached (e.g., anisotropic adhesive film, pressure sensitive adhesive, cyanoacrylate, epoxy, or other suitable adhesive) to create a sealed region. The sealing member 528 may be used to physically couple and/or provide a sealed region for the sensor carrier 402 to the wearable assembly 500.

It is one benefit of the analyte sensor connection techniques described above that the fabrication of the pre-connected sensor 400 may be separated from the fabrication of the electronics (e.g., electronics assembly substrate 530) enclosed within the housing. As described above with reference to the pre-connected sensor structure and the subsequent coating, testing and calibrating processes, the housing with the internally contained electronics can be manufactured in a separate facility from the one that attaches the pre-connected sensor 400 to the sensor electrical interface. This is made possible by providing an analyte sensor electronics interface that is accessible from outside the housing. The housing need not be opened to attach the sensor.

In some advantageous methods, the electrodes for the pre-connected sensor are fabricated and mounted on the substrate in a first location and are shipped to a second location for coating, testing and calibrating. The housing with internal electronics is manufactured in a third location. The housing with the electronics is shipped from the third location to the second location, where the completed analyte sensor is attached to the external electrical interface. The three locations can all be remote from each other. This minimizes handling of the sensitive membrane coated sensor, but still allows separate manufacturing of the other components of the complete device.

Figure 6A:
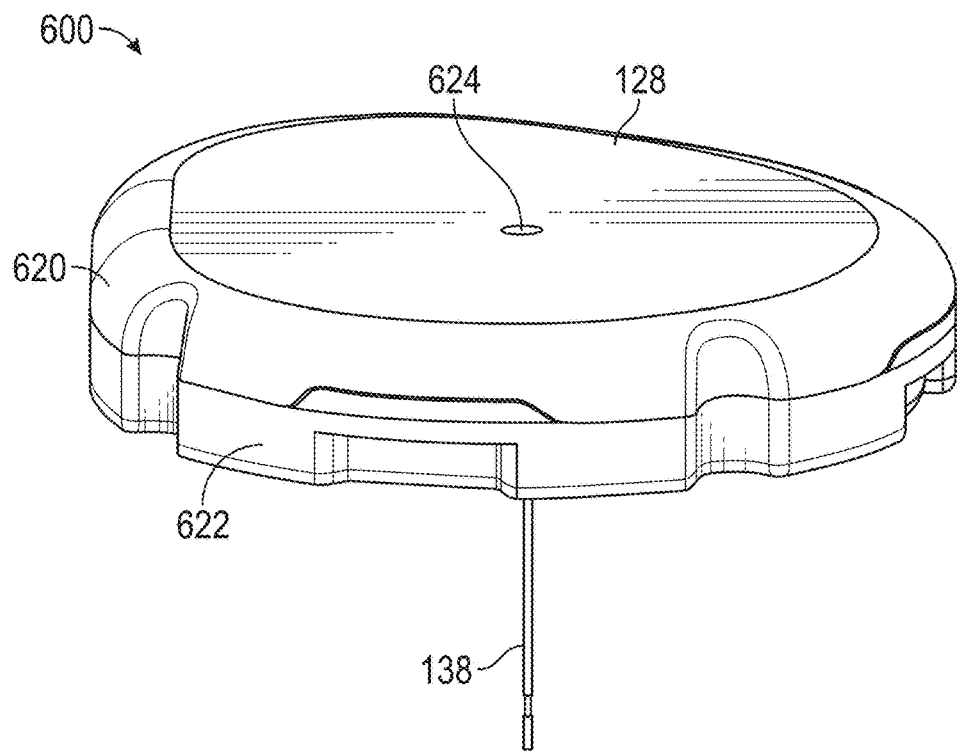
FIG. 6A shows a perspective view of an embodiment of a wearable assembly having a sensor directly connected to an electronics assembly substrate on which sensor electronics are disposed, according to some embodiments.

Sensors Directly Connected to an Electronics Assembly Substrate of a Wearable Assembly FIG. 6A shows a perspective view of an embodiment of a wearable assembly 600 having a sensor 138 directly connected to an electronics assembly substrate 630 via a first conductive contact 324 and a second conductive contact 334 (see FIGS. 6B and 6C) on which sensor electronics 112 can be disposed, according to some embodiments. While not shown in FIG. 6A, wearable assembly 600 may include an adhesive patch 126. Housing 128 may comprise two housing components, a top housing 620 and a bottom housing 622. Top housing 620 and bottom housing 622 can be assembled together to form housing 128. Top housing 620 and bottom housing 622 can be sealed to prevent moisture ingress to at least one internal cavity of housing 128. The sealed housing may include an encapsulating material 628 (e.g. epoxy, silicone, urethane, or other suitable material). In other embodiments, housing 128 is formed as a single component encapsulant (e.g. epoxy) configured to contain at least a proximal portion of sensor 138 and sensor electronics 112. FIG. 6A illustrates an aperture 624 within top housing 620 configured to allow for an insertion component (e.g. hypodermic needle, C-needle, V-needle, open sided needle, etc.) to pass through wearable assembly 600 for insertion and/or retraction. Aperture 624 may be aligned with a corresponding aperture (not shown) in bottom housing 622. In other embodiments, aperture 624 may extend through an off-center location of housing 128. In other embodiments, aperture 624 may extend through an edge of the housing 128, forming a C-shaped channel. In some embodiments aperture 624 includes a sealing material such as a gel, adhesive, elastomer, or other suitable material located within aperture 624.

Figure 6B:
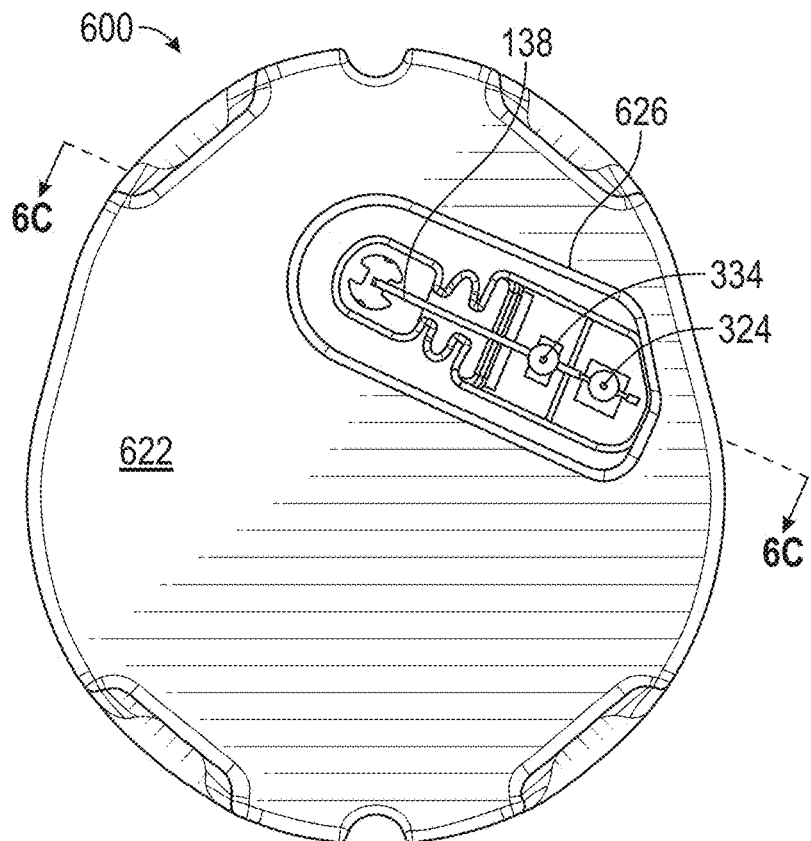
FIG. 6B shows a plan view of the bottom of the wearable assembly of FIG. 6A, according to some embodiments.
Figure 6C:
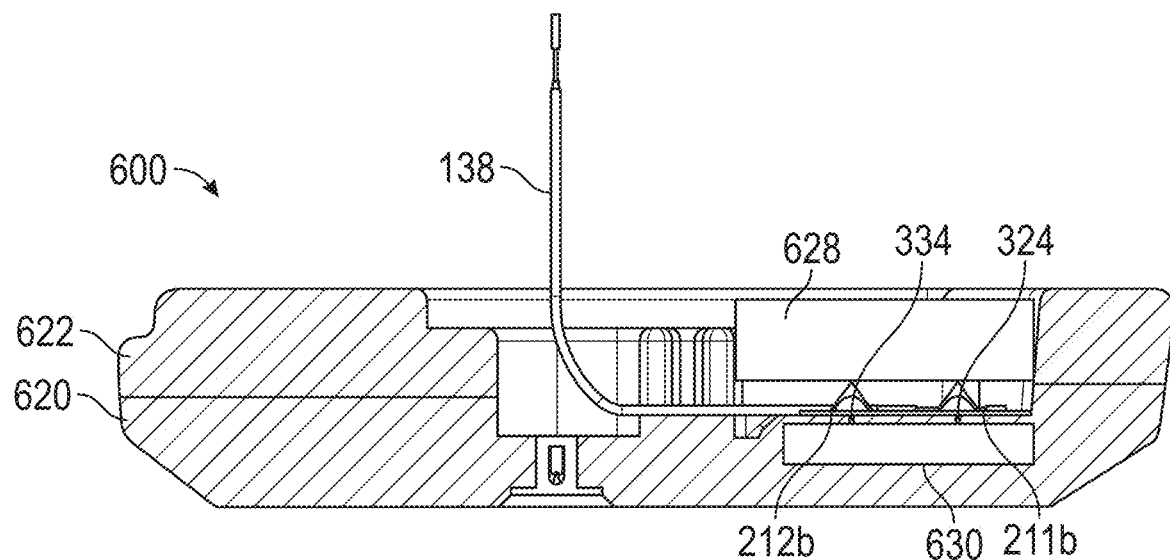
FIG. 6C shows a side cutaway view of the wearable assembly of FIG. 6A, according to some embodiments.

FIG. 6B shows a plan view of the bottom of wearable assembly 600, according to some embodiments. As illustrated, sensor 138 may be directly connected to electronics assembly substrate 630, within the housing 128, via conductive contacts 324, 334, which may extend from electronics assembly substrate 630 through a portion of lower housing 622 and into a cavity of housing 622 within which electrodes of sensor 138 are disposed. Sensor 138 may be installed within an aperture 626 of bottom housing 622. As shown in FIGS. 6A and 6C, sensor 138 may extend out from aperture 626. Aperture 626 may be sized and shaped to retain at least the proximal portion of sensor 138. Sensor 138 may extend approximately parallel to the skin surface and form a 90-degree bend for insertion into the skin. It should be understood that the bottom surface of bottom housing 622 can contain an attachment member (e.g. an adhesive patch 126, not shown) for adhering the wearable assembly to the skin surface of a user.

FIG. 6C shows a side cutaway view of wearable assembly 600 along cut-line 6C-6C of FIG. 6B, according to some embodiments. Various electronic components such as the potentiostat 210 and other components illustrated in FIG. 2 may be mounted on or to electronics assembly substrate 630, typically some form of printed circuit board. It is contemplated that sensor 138 has a direct electrical coupling with electronics assembly substrate 630. Various methods may be used to establish electrical connection (e.g. pins, solder, conductive elastomer, conductive adhesive, etc.) between one or more contacts or electrodes of sensor 138, such as contacts 211*b* and 212*b*, and one or more conductive contacts, such as contacts 324, 334 electrically and/or physically coupled to electronics assembly substrate 630. Sensor 138 may be configured to interface with electronics assembly substrate 630 through the bottom housing 622. In other implementations, sensor 138 may be configured to interface with electronics assembly substrate 630 through top housing 620. In some other implementations, sensor 138 is configured to interface with electronics assembly substrate 630 through the side of wearable assembly 600. Also shown in the figure, an optional sealing member 628 may be configured to insulate at least a portion of sensor 138 and from potential moisture ingress. In some instances, a sealing member 628 may be liquid dispensed (e.g., adhesive, gel, epoxy) or a solid material (e.g., elastomer, polymer). The sealing member 628 may be an assembled component that is welded (e.g., laser or ultrasonic, hot plate), or otherwise permanently attached (e.g., anisotropic adhesive film, pressure sensitive adhesive, cyanoacrylate, epoxy, or other suitable adhesive) to create a sealed region or cavity. In some embodiments, the sealing member 628 may be used to physically secure or couple at least a portion of sensor 138 to wearable assembly 600 and/or to provide a sealed region for at least a proximal portion of sensor 138.

It is one benefit of the analyte sensor connection techniques described above that the fabrication and/or manufacture of wearable assembly 600 can require fewer steps compared to the embodiments utilizing the pre-connected sensor 400 of FIGS. 4A-5C, thereby decreasing manufacturing complexity and cost.

Caps for Simultaneously Sealing from Moisture Ingress and Securing a Sensor

In some embodiments, it is desirable that sensor 138 and/or sensor electronics 112 (see FIG. 1 and, e.g., electronics module 135 of FIG. 3C) be sealed from the outside environment to prevent moisture from seeping into or condensing onto such components, as such moisture can cause shorting, oxidation, or otherwise cause damage. One such solution may be to fill an encapsulating sealant into at least a portion of a cavity within which at least a portion of sensor 138 is disposed. However, care must be taken that such encapsulating sealant does not inappropriately flow to certain other portions of the cavity, or such encapsulating sealant may undesirably occlude other features of wearable assembly 600, for example, through-hole 180 for a needle or other sensor insertion member to pass during deployment of wearable assembly 600. In addition, sensor 138 may need to be held in place while such encapsulating sealant is deployed and/or cured to avoid permanent mispositioning of sensor 138. For example, applying pressure to a pressure-sensitive adhesive in contact with sensor 138 may tend to move sensor 138, causing misalignment. As another example, when using a curable epoxy to set sensor 138 in place, extra fixturing may seem necessary to datum sensor 138 in place during epoxy curing to avoid misalignment.

Some example solutions for simultaneously holding sensor 138 in place while also ensuring encapsulating sealant does not inappropriately flow to undesired portions of a cavity of housing 128 are described in more detail in connection with several of the following figures.

Figure 7A:
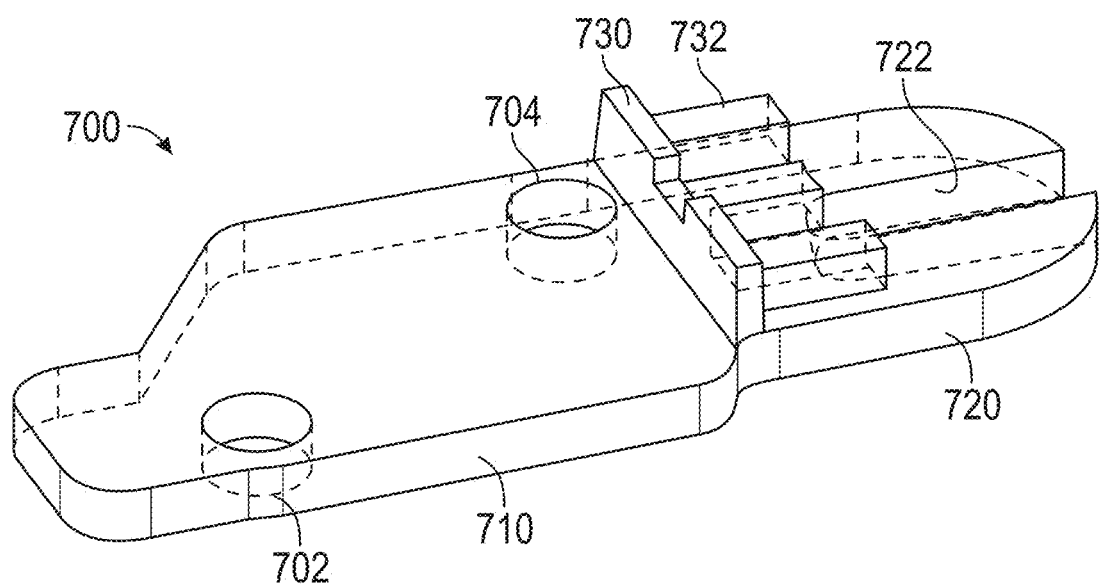
FIG. 7A illustrates a perspective view of a cap for sealing an aperture within a housing of a wearable assembly, according to some embodiments.
Figure 7B:
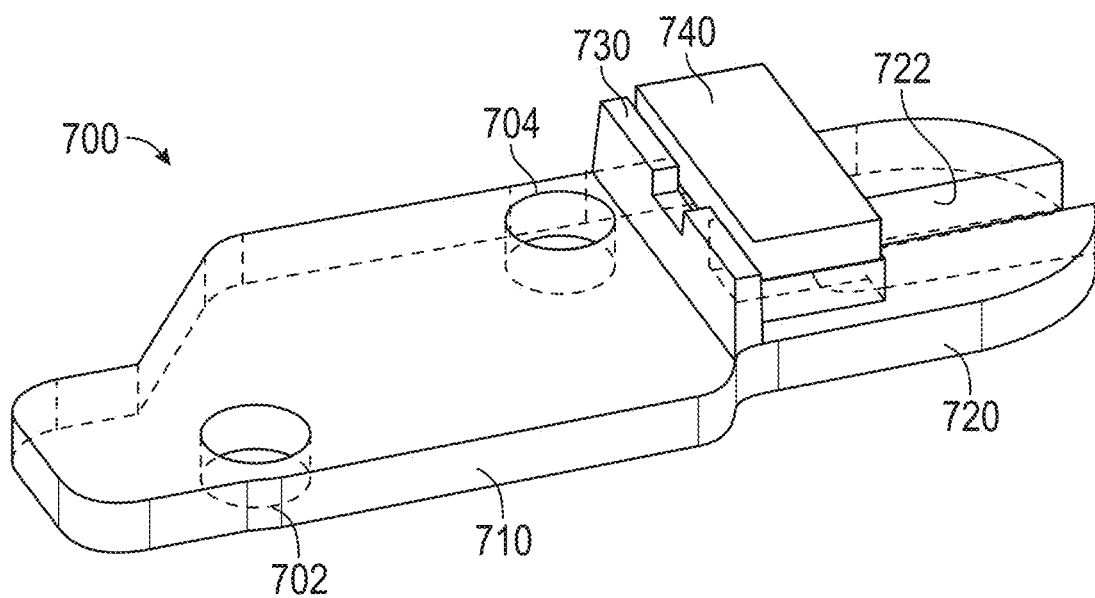
FIG. 7B illustrates another perspective view of the cap of FIG. 7A, according to some embodiments.
Figure 7C:
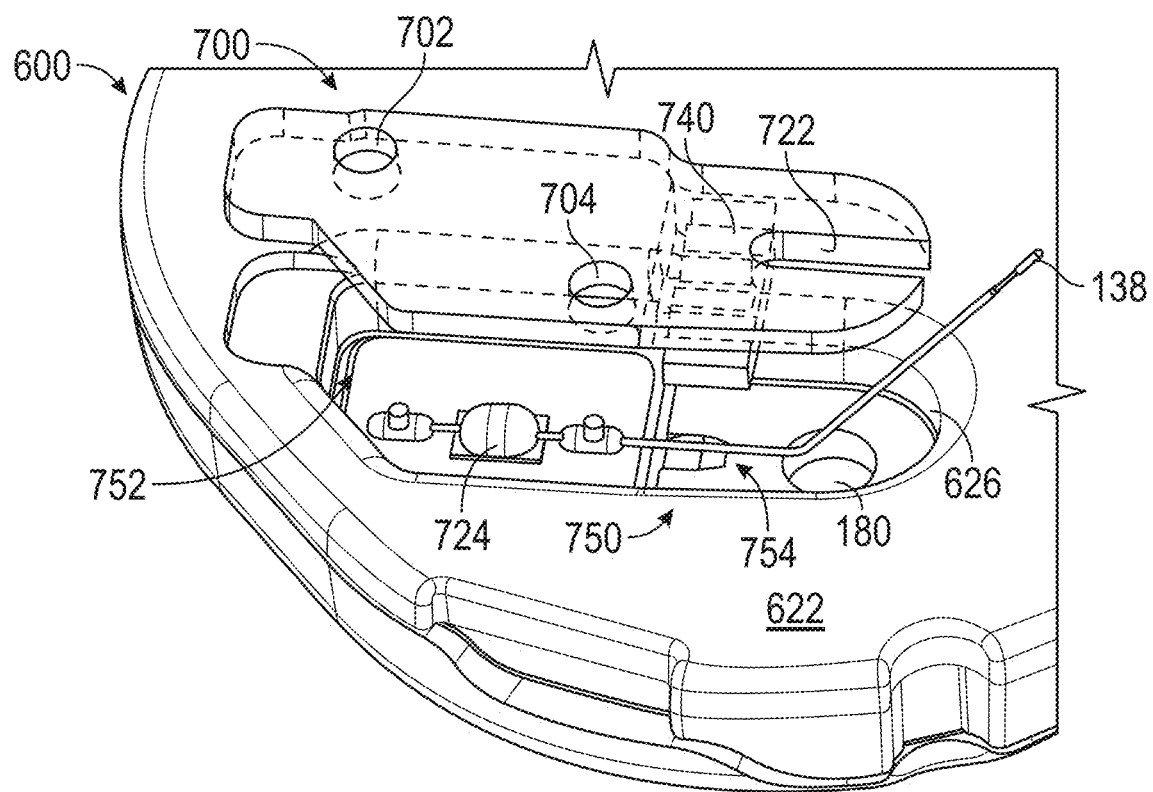
FIG. 7C illustrates a perspective view of the cap of FIGS. 7A and 7B disposed over an aperture within the housing of the wearable assembly, according to some embodiments.

FIGS. 7A and 7B illustrate perspective views of a cap 700 for sealing aperture 624 within housing 128, according to some embodiments. FIG. 7C illustrates a perspective view of cap 700 disposed over aperture 626 within housing 128, according to some embodiments.

As illustrated in FIG. 7C, aperture 626 within lower housing 622 forms, provides or defines a cavity 750 within which sensor electronics 112 is disposed (e.g., on electronics assembly substrate 630). A first portion 752 of cavity 750 may hold at least a portion of sensor 138. A second portion 754 of cavity 750 may include at least through-hole 180. When properly placed, sensor 138 may be directly electrically contacted to sensor electronics 112 on electronics assembly substrate 630, for example via conductive contacts 324, 334, and may have portions disposed within first portion 752 and second portion 754 of cavity 750. As further shown in FIG. 7C, at least a portion of sensor 138 may be adhered to housing 622 utilizing any suitable glue 724, for example a UV curing glue, epoxy or the like, as will be described in more detail in connection with various figures below.

As shown in FIG. 7A, cap 700 is configured to cover, fit into, or fit on aperture 626 of lower housing 622, thereby providing a controlled fill volume within first portion 752 of cavity 750 while at the same time pressing sensor 138 to an inner surface of cavity 750 and/or of lower housing 622, thereby also acting as a datuming feature for sensor 138. In some embodiments, cap 700 may comprise a molded part, a die-cut sheet of material, or any other suitable form. In some embodiments, cap 700 may have an adhesive, for example a pressure-sensitive adhesive, on one side (not shown) for securing cap 700 into or over aperture 626.

Cap 700 comprises a first portion 710 configured to be disposed over first portion 752 of the cavity 750 and a second portion 720 configured to be disposed over second portion 754 of the cavity 750. In some embodiments, first and second portions 710, 720 of cap 700 may be coplanar and may be formed of a single piece. First portion 710 of cap 700 may further comprise a first hole 702 configured as an inlet port for receiving an encapsulating sealant (e.g., a curable epoxy) into first portion 752 of cavity 750 for sealing at least a portion of sensor 138 from moisture. First portion 710 of cap 700 may further comprise a second hole 704 configured as an outlet port for excess encapsulating sealant injected into first portion 752 of cavity 750 through first hole 702. In some embodiments, first hole 702 and second hole 704 may be disposed near opposite ends of first portion 710 of cap 700 to thereby provide for complete or near-complete filling of first portion 752 of cavity 750 with the encapsulating sealant.

Cap 700 may further comprise an encapsulant dam 730 disposed on a side of cap 700 configured to face aperture 626. In some embodiments, encapsulant dam 730 may have a height sufficient for encapsulant dam 730 to contact a surface of lower housing 622 within cavity 750 when cap 700 is properly placed within or on aperture 626. In some other embodiments, encapsulant dam 730 may have a slightly lower height than just described to allow encapsulant dam 730 to nearly contact the surface of lower housing 622 within cavity 750 when cap 700 is properly placed within or on aperture 626.

Cap 700 may further comprise an optional shelf 732 disposed adjacent to dam 730 and configured to receive a compliant component 740 (e.g., a soft, foam or rubber material, see FIG. 7B). In some embodiments, shelf 732 may have a height such that a surface of compliant component 740, configured to face aperture 626, extends slightly farther from cap 700 than a similarly facing surface of dam 730. When cap 700 is properly placed within or on aperture 626, compliant component 740 is configured to press against at least a portion of sensor 138 and against the surface of lower housing 622 within cavity 750. Accordingly, compliant component 740 datums sensor 138 to the surface of lower housing 622 within cavity 750 in a compliant manner and seals first portion 752 of cavity 750 from second portion 754 of cavity 750. In some embodiments, dam 730 can further assist in sealing first portion 752 of cavity 750 from second portion 754 of cavity 750. Accordingly, when encapsulating sealant is injected into first portion 752 of cavity 750 to seal at least some portions of sensor 138 from moisture ingress, dam 730 and/or compliant component 740 prevent the encapsulating sealant from flowing into second portion 754 of cavity 750, thereby preventing undesirable occlusion of through-hole 180, while also providing assembly tolerances between cap 700, aperture 626, and/or lower housing 622.

Second portion 720 of cap 700 may further comprise a slot 722 configured to allow at least a distal portion of sensor 138 to pass through cap 700. Utilizing slot 722 in cap 700 instead of a circular hole may allow a smaller through-hole 180 in wearable assembly 600.

In some embodiments, an outside-facing surface of cap 700 may be configured to fit nominally flush with an outside-facing surface of lower housing 622 when properly placed. In the alternative, the outside-facing surface of cap 700 may be configured to fit slightly recessed compared to the outside-facing surface of lower housing 622 when properly placed. In such nominally-flush or slightly-recessed embodiments, an outer perimeter of cap 700 may substantially correspond to an inner perimeter of aperture 626.

Figure 7D:
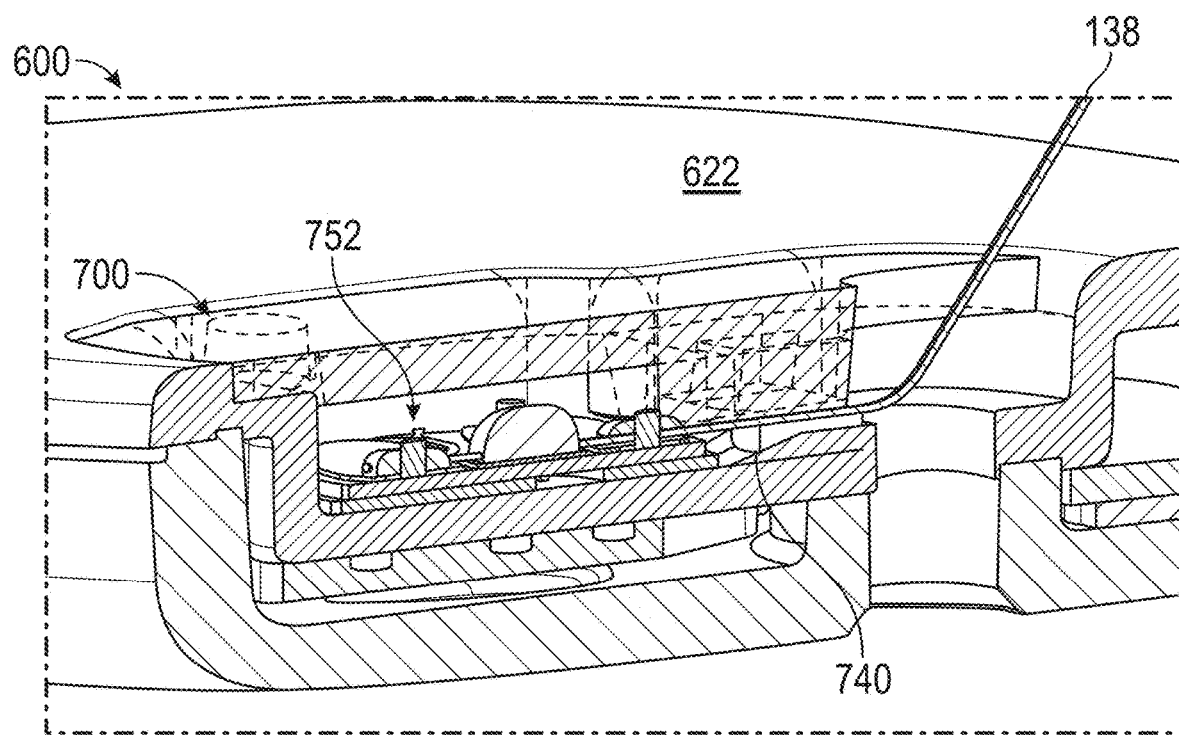
FIG. 7D illustrates a perspective view of the cap of FIGS. 7A-7C disposed flush or slightly recessed within the aperture of the housing, according to some embodiments.

FIG. 7D illustrates a perspective view of cap 700 disposed flush or slightly recessed within aperture 626 of housing 128, according to some embodiments. Cap 700 may be held in place during encapsulating sealant deposition using toe features, snap features, friction-fit features, pressure-sensitive adhesive, or any other suitable securing method. In some embodiments, cap 700 may comprise a material transparent or sufficiently translucent to ultraviolet radiation to allow for curing of a UV-curing epoxy encapsulating sealant disposed in first portion 752 of cavity 750.

In yet another alternative, cap 700 may be configured to cover aperture 626 while being disposed flush on the outside-facing surface of lower housing 622. In such other alternatives, an outer perimeter of cap 700 may be larger than the inner perimeter of aperture 626 and may have any size and shape up to and including an outer perimeter of lower housing 622 (not shown). In such embodiments, cap 700 may be adhered to the outside-facing surface of lower housing 622 at portions of lower housing 622 outside the inner perimeter of aperture 626, which may aid in ultimately adhering wearable assembly 600 to a flat surface of skin.

While cap 700 is described above as utilized in connection with wearable assembly 600, which does not include pre-connected sensor 400 or sensor carrier 402, the present disclosure is not so-limited and cap 700 may also be utilized with wearable assembly 500 comprising pre-connected sensor 400.

Figure 8A:
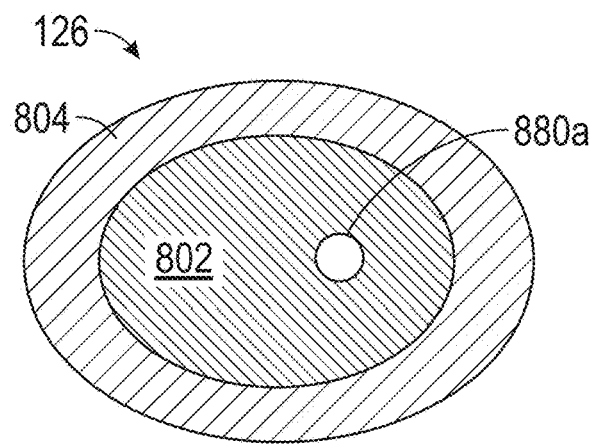
FIG. 8A illustrates a plan view of a two-part patch for securing a wearable assembly to the skin of a host, according to some embodiments.

In some embodiments, rather than utilizing a separate adhesive for adhering cap 700 to lower housing 622, the adhesive portion normally utilized to adhere patch 126 to lower housing 622 of wearable assembly 600 may be repurposed to additionally adhere or otherwise secure cap 700 to lower housing 622 once properly placed in, on or over lower housing 622. For example, as shown in FIG. 8A, patch 126 may comprise two parts: a first adhesive portion 802 configured to secure cap 700 to lower housing 622 and to simultaneously adhere lower housing 622 of wearable assembly 600 to patch 126, and a second adhesive portion 804 configured to adhere the first adhesive portion 802, and so wearable assembly 600, to the skin of the user.

Figure 8B:
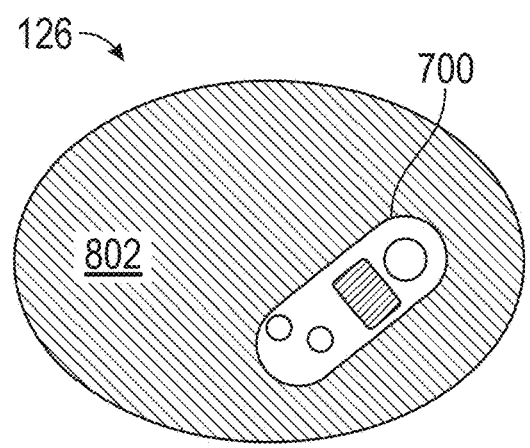
FIG. 8B illustrates a plan view of a cap, such as the caps described in connection with FIGS. 7A-7D, 9 and/or 10, coupled to a patch for securing a wearable assembly to the skin of the host, according to some embodiments.

FIG. 8B illustrates an outward-facing surface of cap 700 secured to first adhesive portion 802. First adhesive portion 802 may comprise apertures or holes configured to coincide with first and second holes 702, 704 of cap 700 and through-hole 180 of wearable assembly 600 when cap 700 is properly placed on, flush with, or recessed within aperture 626 of lower housing 622.

Figure 8C:
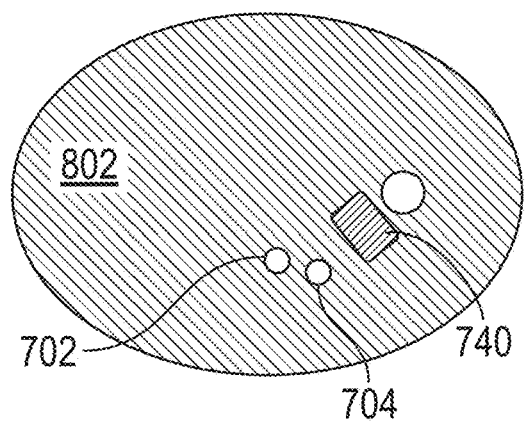
FIG. 8C illustrates a plan view of a patch configured to act as a cap, similar to the caps described in connection with FIGS. 7A-7D, 9 and/or 10, and for securing a wearable assembly to the skin of the host, according to some embodiments.

In an alternative embodiment, as shown in FIG. 8C, cap 700 may be omitted and first adhesive portion 802 may comprise first and second holes 702, 704 and an aperture or hole configured to coincide with through-hole 180 of wearable assembly 600 when first adhesive portion 802 is properly placed on lower housing 622. In such an alternative embodiment, first adhesive portion 802 may further comprise compliant component 740 having substantially the same functionality as previously described in connection with FIGS. 7A-7D. Accordingly, properly placing and applying first adhesive portion 802 on lower housing 622 causes compliant component 740 to press against at least a portion of sensor 138 and against the surface of lower housing 622 within cavity 750. Accordingly, compliant component 740 datums sensor 138 to the surface of lower housing 622 within cavity 750 in a compliant manner and also seals first portion 752 of cavity 750 from second portion 754 of cavity 750. Accordingly, when encapsulating sealant is injected into first portion 752 of cavity 750 to seal sensor electronics 112 and at least a portion of sensor 138 from moisture ingress, compliant component 740 prevents the encapsulating sealant from flowing into second portion 754 of cavity 750, thereby preventing undesirable occlusion of through-hole 180.

Figure 8D:
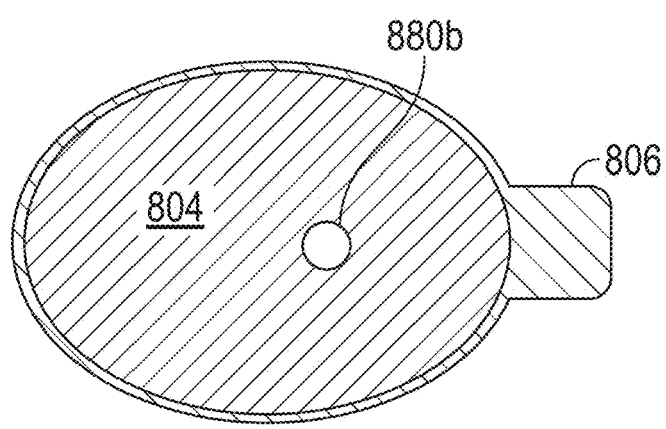
FIG. 8D illustrates a plan view of a portion of the patch of FIG. 8A configured to adhere the patch a cap, such as the caps described in connection with FIGS. 7A-7D, 9 and/or 10, and a wearable assembly to the skin of the host, according to some embodiments.

Regardless of whether embodiments shown in FIG. 8B or 8C are used, second adhesive portion 804 may be initially disposed on a liner 806, which may be removed and second adhesive portion 804 placed, separately, on an outside-facing surface of first adhesive portion 802 of patch 126 for subsequent securing of wearable assembly 600 onto the skin of the user. As shown in FIG. 8D, second adhesive portion 804 may further comprise an aperture or hole 880b configured to coincide with through-hole 180 of wearable assembly 600 when second adhesive portion 804 is properly placed on the outside-facing surface of first adhesive portion 802 of patch 126.

Figure 9:
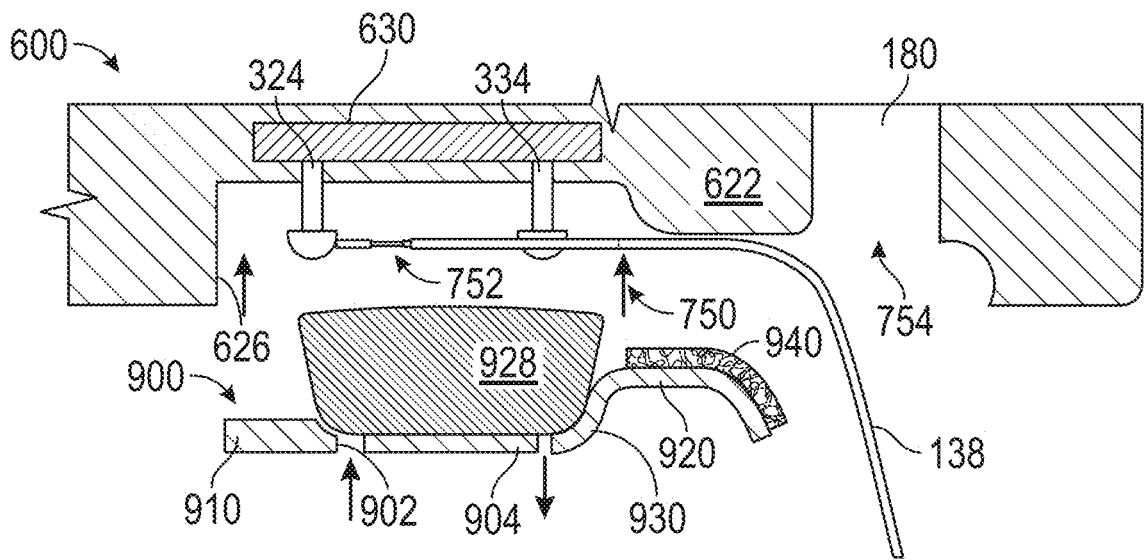
FIG. 9 illustrates a side cutaway view of a cap for sealing an aperture within a housing of a wearable assembly, according to some embodiments.

FIG. 9 illustrates a cutaway side view of an alternative cap 900 to cap 700, according to some embodiments. Like numerals between cap 900 and cap 700 correspond to similar features. Cap 900 comprises a first portion 910 configured to be disposed over first portion 752 of cavity 750 in lower housing 622 and a second portion 920. In some embodiments, second portion 920 is configured to be disposed over second portion 754 of cavity 750, which may comprise through-hole 180 in lower housing 622. In other embodiments, second portion 920 is configured to be disposed adjacent to second portion 754 of cavity 750. First portion 910 comprises a first hole 902 configured as an inlet port for receiving an encapsulating sealant (e.g., epoxy) into first portion 752 of cavity 750 for sealing at least a portion of sensor 138 from moisture ingress. First portion 910 of cap 900 may further comprise a second hole 904 configured as an outlet port for excess encapsulating sealant injected into first portion 752 of cavity 750 through first hole 902. In some embodiments, first hole 902 and second hold 904 may be disposed near opposite ends of the first portion 910 of cap 900 to thereby provide for complete or near-complete filling of first portion 752 of cavity 750 with the encapsulating sealant.

Cap 900 may further comprise an encapsulant dam 930. However, unlike with cap 700, first and second portions 910, 920 of cap 900 may not be coplanar and encapsulant dam 930 may instead comprise at least a portion of cap 900 that extends between the planes of and connects first and second portions 910, 920. Accordingly, at least a portion of second portion 920 disposed adjacent to dam 930 may also function as a shelf 932 configured to receive a compliant component 940 (e.g., a soft, foam or rubber material). When cap 900 is properly placed within or on aperture 626, compliant component 940 is configured to press against at least a portion of sensor 138 and against the surface of lower housing 622 within cavity 750. Accordingly, compliant component 940 datums sensor 138 to the surface of lower housing 622 within cavity 750 in a compliant manner and also, with or without the help of dam 930, seals first portion 752 of cavity 750 from second portion 754 of cavity 750. Accordingly, when encapsulating sealant is injected into first portion 752 of cavity 750 to seal at least a portion of sensor 138 from moisture ingress, dam 930 and/or compliant component 940 prevent the encapsulating sealant from flowing into second portion 754 of cavity 750, thereby preventing undesirable occlusion of through-hole 180, while also providing assembly tolerances between cap 900, aperture 626, and/or lower housing 622.

Although not shown in FIG. 9, second portion 920 of cap 900 may further comprise a slot, similar to slot 722 of cap 700, configured to allow at least a distal portion of sensor 138 to pass through cap 900 when cap 900 is properly placed. Alternatively, in some embodiments where second portion 920 of cap 900 does not extend laterally to through-hole 180, such a slot may be omitted.

While cap 900 is described above as utilized in connection with wearable assembly 600, which does not include pre-connected sensor 400, the present disclosure is not so-limited and cap 900 may also be utilized with wearable assembly 500 comprising pre-connected sensor 400 and sensor carrier 402.

In some embodiments it may be advantageous to mount or bond sensor 138 to a cap before assembly of wearable assembly 600 and provide one or more pairs of mating contacts on the cap and on wearable assembly 600 for connection of the sensor to the electronics in wearable assembly 600 (e.g., sensor electronics 112) when the cap is properly placed on lower housing 622 of wearable assembly 600.

Figure 10:
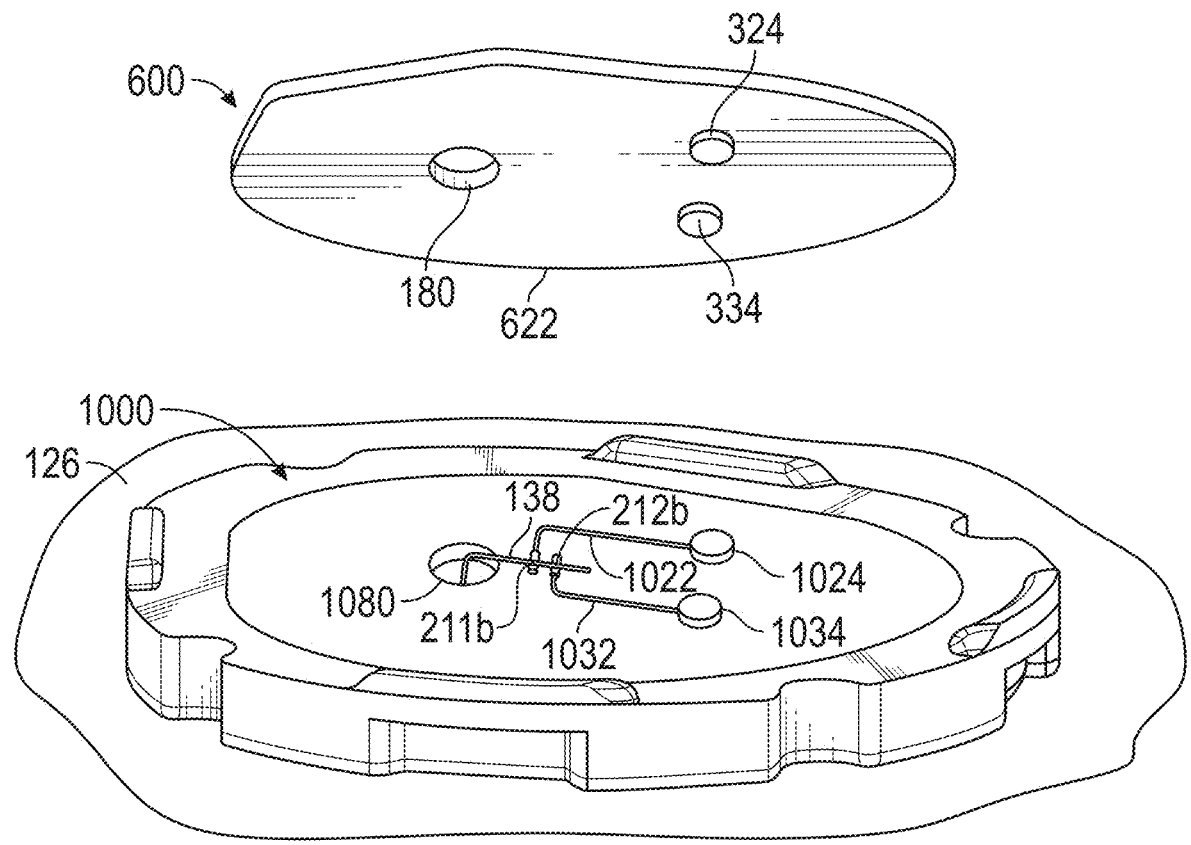
FIG. 10 illustrates a perspective view of a cap comprising a pre-connected sensor and configured to seal an aperture within a housing of a wearable assembly, according to some embodiments.

FIG. 10 illustrates a perspective view of a cap 1000 having sensor 138 pre-mounted thereto, according to some embodiments. FIG. 10 illustrates cap 1000 having an outward-facing side adhered to patch 126, similar to previous description in connection with FIG. 8B. Cap 1000 comprises a through-hole 1080 configured to line up with through-hole 180 of wearable assembly 600 when cap 1000 is properly placed on lower housing 622. Sensor 138 may be adhered or otherwise secured to a top face of cap 1000 such that a distal portion of sensor 138 extends through through-hole 1080 and away from cap 1000. Cap 1000 further comprises a first trace 1022 and a second trace 1032. First trace 1022 is configured to electrically connect contact 211b of sensor 138 to a first contact 1024 on cap 1000. Second trace 1032 is configured to electrically connect contact 212b of sensor 138 to a second contact 1034 on cap 1000. As shown in the figure, lower housing 622 is illustrated as having a plurality of contacts, e.g., contacts 324 and 334, disposed on its outward-facing surface. First and second contacts 1022 and 1024 are configured to make direct electrical and physical contact with respective contacts 324 and 334 when cap 1000 is properly placed on lower housing 622, thereby electrically coupling sensor 138 to sensor electronics 112. Cap 1000 may be bonded, adhered or otherwise attached to lower housing 622 utilizing any suitable means.

Utilizing Sensor Bend Geometry to Locate and Hold the Sensor on a PCB

Due to the small size of sensor 138, and constraints on acceptable handling locations along its length, establishing proper alignment of sensor 138 on wearable assembly 600 can be challenging, particularly when there is no carrier or handle attached to sensor 138 prior to integration with electronics assembly substrate 630, and especially where sensor 138 has a substantially cylindrical or otherwise at least partially rounded shape. In addition, the natural curvature of sensor 138, which can be difficult to straighten, may cause sensor 138 to move around undesirably when handled. Utilization of a single pre-bend in the distal region of sensor 138 has limited usefulness in preventing such undesirable movement at the time of placing sensor 138 within wearable assembly 600 due to the single pre-bend's proximity to the needle through-hole 180 and to membrane 108. Accordingly, several solutions that utilize sensor bend geometry to assist with lateral and rotational location of sensor 138 relative to electronics assembly substrate 630 (e.g., a transmitter PCB) are described below in connection with at least FIGS. 11A-20.

The utilization of such bends, kinks, loops and/or curves in sensor 138, established by one or more pre-forming step(s), provides retaining features in sensor 138 at points that are spaced apart sufficiently to provide support, constraint, bias force, and/or location of sensor 138 relative to features on wearable assembly 600 and/or on electronics assembly substrate 630. These geometries may also be desirably utilized to increase the leakage current path between electrodes on sensor 138 by leveraging a longer insulation region and/or by bending sensor 138 in such a manner that the resultant distance between the electrode pads is increased compared to a straight, unbent, or singly-bent sensor 138. Moreover, intentionally bending sensor 138 at multiple points along its length can create a more easily-handled shape that can mimic a flat surface on which sensor 138 can rest. Moreover, as will be described in more detail below, the elastic properties of sensor 138 can also be leveraged to generate a biasing or retention force against one or more features of electronics assembly substrate 630 and/or of housing 622, thereby causing sensor 138 to remain in place before applying subsequent mechanical features and/or adhesives.

Figure 11A:
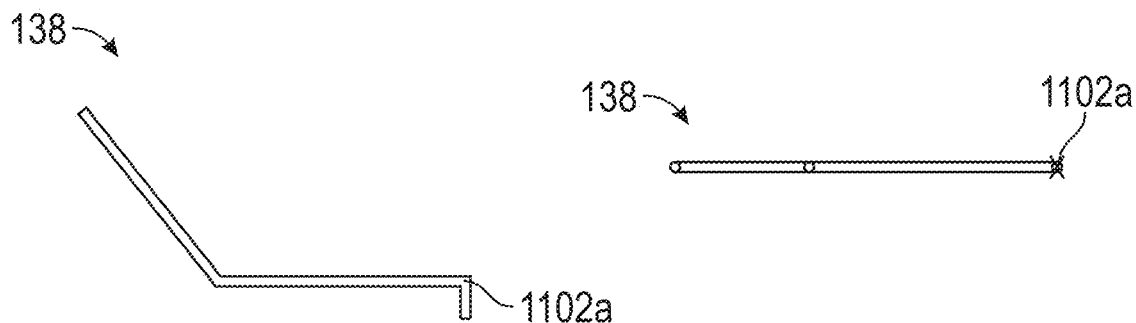
FIG. 11A illustrates side and top views of a first type of sensor bend, according to some embodiments.
Figure 11B:
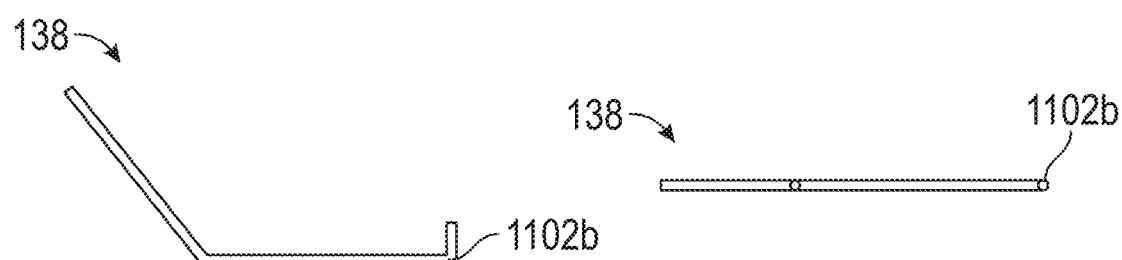
FIG. 11B illustrates side and top views of a second type of sensor bend, according to some embodiments.
Figure 11C:
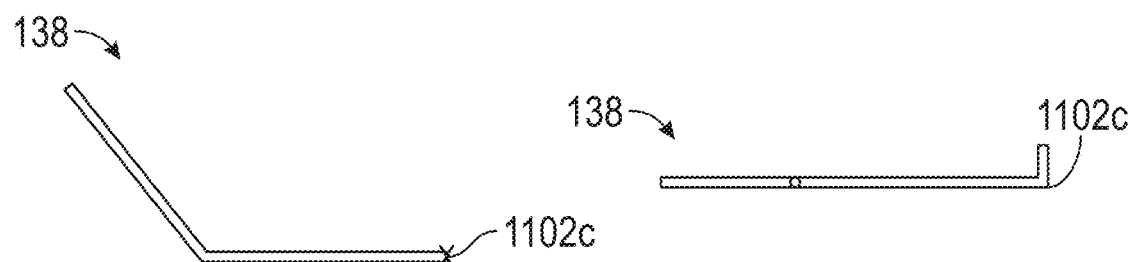
FIG. 11C illustrates side and top views of a third type of sensor bend, according to some embodiments.

FIGS. 11A-11C separately illustrate three main types of bends in sensor 138, according to some embodiments. While embodiments are described for sensor 138 in relation to electronics assembly substrate 630, the present disclosure also contemplates similar embodiments for sensor 138 in relation to lower housing 622. For example, at least a portion of lower housing 622 may physically separate electronics assembly substrate 630 from the portion of lower housing 622 in which at least portions of sensor 138 extends (see, e.g., at least FIGS. 6A-7D and 9), Where sensor 138 is described as contacting, extending in a particular direction with respect to, or applying a force or torque to a surface of electronics assembly substrate 630, the present disclosure additionally and/or alternatively contemplates such contact, direction of extension, and/or applying of force or torque to surfaces of lower housing 622.

FIG. 11A illustrates side and top views of a first type of sensor bend 1102a, in which sensor 138 is bent so a portion of sensor 138 proximal to electronics assembly substrate 630 extends in a direction towards wearable assembly 600, for example, such that the proximal portion of sensor 138 extends through electronics assembly substrate 630. FIG. 11B illustrates side and top views of a second type of sensor bend 1102*b*, in which sensor 138 is bent so the portion of sensor 138 proximal to electronics assembly substrate 630 extends in a direction away from wearable assembly 600, for example, such that the proximal portion of sensor 138 extends away from electronics assembly substrate 630. FIG. 11C illustrates side and top views of a third type of sensor bend 1102*c*, in which sensor 138 is bent so the portion of sensor 138 proximal to electronics assembly substrate 630 extends in a direction neither toward nor away from wearable assembly 600, but substantially parallel to the plane of electronics assembly substrate 630 to which it is mounted and/or electrically connected.

While several examples of each type of sensor bend are described below, the present disclosure contemplates any and all combinations of such examples, with or without additional bends and/or features of sensor 138. Moreover, although embodiments are generally described as relating to the wearable assembly 600, which does not include pre-connected sensor 400, the present disclosure is not so-limited and such embodiments may also be utilized with wearable assembly 500 comprising pre-connected sensor 400 and sensor carrier 402. Several example embodiments of the first type of sensor bend, as illustrated in FIG. 11A, will now be described in connection with FIGS. 12 and 13 below.

Figure 12:
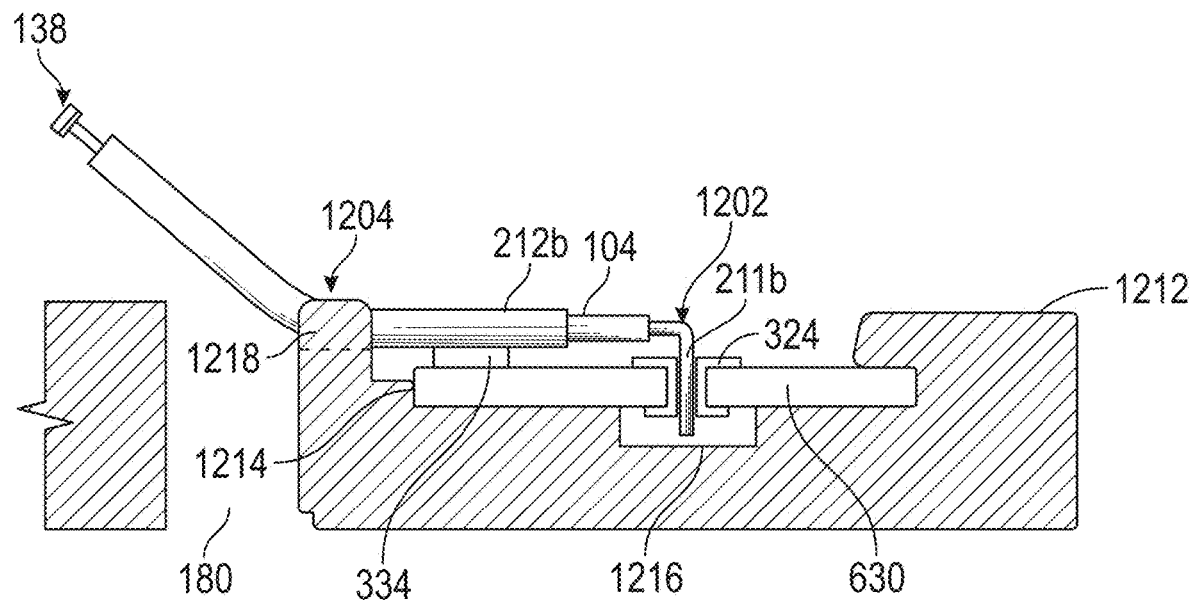
FIG. 12 illustrates a side cutaway view of an example of the first type of sensor bend of FIG. 11A, according to some embodiments.

FIG. 12 shows a side, cutaway view of an example arrangement including a sensor bend 1202 that causes the proximal portion of sensor 138 to extend through electronics assembly substrate 630, according to some embodiments. FIG. 12 illustrates lower housing 622 of wearable assembly 600, electronics assembly substrate 630 disposed on lower housing 622, and sensor 138, comprising a plurality of bends 1202, 1204, disposed on and mechanically and electrically coupled to electronics assembly substrate 630.

Electronics assembly substrate 630 is illustrated as comprising a PCB material such as FR4, although the present disclosure is not so-limited and any suitable PCB material is also contemplated. Electronics assembly substrate 630 further comprises a plurality of electrical contacts, for example contacts 324, 334 as previously described in connection with at least FIG. 3D. In FIG. 12, contact 324 is illustrated as an electrically-conductive, plated through-hole, although the present disclosure is not so-limited and any other suitable contact is also contemplated.

Sensor 138 is illustrated as having a first bend 1202 at a proximal portion of sensor 138 and a second bend 1204 at a medial or distal portion of sensor 138, such that a portion of the elongated body of sensor 138 distal of first bend 1202 extends substantially parallel to a plane of electronics assembly substrate 630 and a portion of the elongated body proximal to first bend 1202 extends substantially perpendicular to the plane of electronics assembly substrate 630 and through electronics assembly substrate 630. In some embodiments, first bend 1202 may be an approximately 90° bend. However, the present disclosure is not so-limited and first bend 1202 may have any suitable bend angle. In some embodiments, first bend 1202 occurs along the working electrode contact 211*b* such that at least a portion of contact 211*b* passes through the through-hole contact 324, thereby establishing mechanical positioning of sensor 138 before conductive connections (e.g., epoxy, solder, or the like) are applied to electrically connect contacts 211*b* and 324 and to electrically connect contacts 212*b* and 334, for example.

Additionally, in some embodiments, lower housing 622 may further comprise a molded geometry comprising one or more features configured to support electronics assembly substrate 630 and/or sensor 138 at or near second bend 1204.

For example, electronics assembly substrate 630 can be configured to rest on a portion of lower housing 622. Lower housing 622 can further comprise one or more ridges, recesses, or surfaces 1212, 1214 configured to abut one or more respective edges (e.g., lateral edges) of electronics assembly substrate 630. Among other advantages, the one or more ridges, recesses, or surfaces 1212, 1214 provide for more accurate placement of electronics assembly substrate 630 with respect to lower housing 622.

In addition, and/or alternative, lower housing 622 can comprise a recess 1216 immediately below plated through-hole contact 324 that allows for the proximal portion of sensor 138 to extend through electronics assembly substrate 630 and, in some cases, at least partially into the recess 1216. Among other advantages, recess 1216 provides additional assembly tolerances for placement of sensor 138 on electronics assembly substrate 630.

In addition, and/or alternative, lower housing 622 can comprise a notch 1218 configured to align a medial and/or distal portion of sensor 138 at, near or adjacent to second bend 1204. Among other advantages, notch 1218 provides additional alignment and restricts undesirable movement of sensor 138 prior to and after securing sensor 138 to electronics assembly substrate 630 and/or to lower housing 622.

In some embodiments, a bend of the first type (e.g., substantially parallel to the plane of electronics assembly substrate 630 to substantially perpendicular and through the plane of electronics assembly substrate 630) may be utilized to purposefully exploit the elastic properties of sensor 138 to generate a biasing or retention force against one or more features of electronics assembly substrate 630 and/or of wearable assembly 600.

Figure 13:
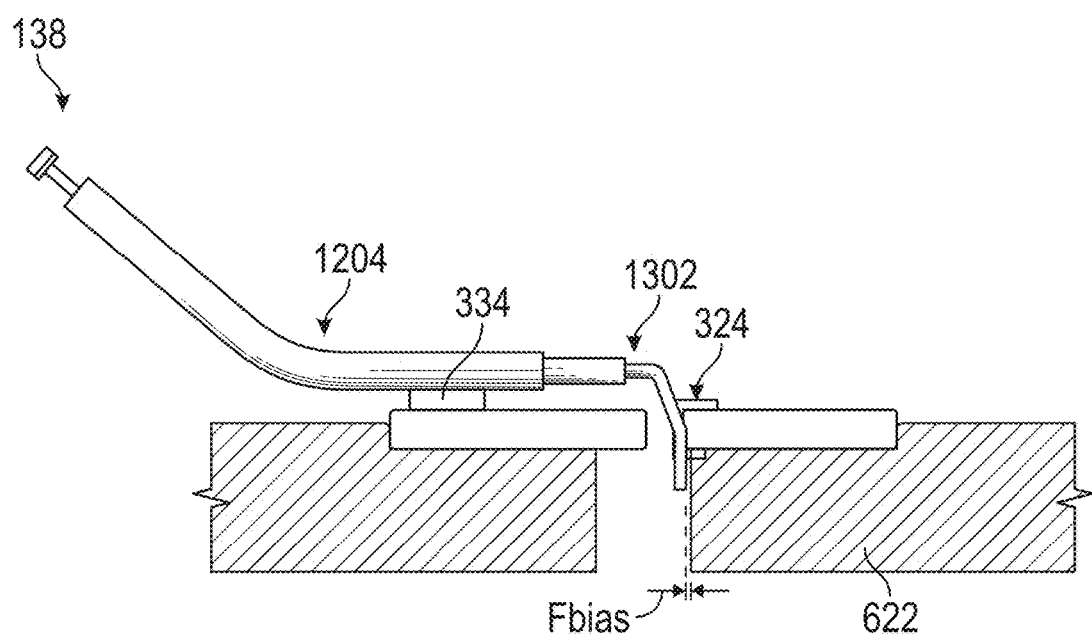
FIG. 13 illustrates a side cutaway view of another example of the first type of sensor bend of FIG. 11A, according to some embodiments.

For example, FIG. 13 shows a side, cutaway view of an example arrangement including a first sensor bend 1302 that causes the proximal portion of sensor 138 to extend through electronics assembly substrate 630 while simultaneously presenting a biasing force against electronics assembly substrate 630, according to some embodiments. Electronics assembly substrate 630 is shown as comprising contact 324, which may be an electrically-conductive, plated through-hole, as previously described in connection with FIG. 12, or which may alternatively be a planar plated contact at least partially surrounding the illustrated through-hole in electronics assembly substrate 630, or a conductive pin or post configured to extend through lower housing 622 to reach connecting portions of sensor 138, as previously described in connection with at least FIGS. 6A-9. Contact 334 may similarly comprise such a conductive pin or post.

Sensor 138 is illustrated as having first bend 1302 at a proximal portion of sensor 138 and second bend 1204, as previously described in connection with FIG. 12, at a medial or distal portion of sensor 138. First bend 1302 may cause a direction of extension of the proximal portion of sensor 138 to transition, by a desired angle (e.g., between 1-179°, from substantially in-plane with electronics assembly substrate 630 to substantially angled through-plane with respect to electronics assembly substrate 630 such that at least some of the proximal portion of sensor 138 contacts and exerts a biasing force against a portion of electronics assembly substrate 630 (e.g., a sidewall of the through-hole). This will cause the sidewall of the through-hole to exert an equal but opposite biasing force on the proximal portion of sensor 138, thereby securing sensor 138 in a desired orientation and position before conductive connections (e.g., epoxy, solder, or the like) are applied between or to the proximal portion of sensor 138 and the contact 324 and between or to an appropriate portion of sensor 138 and the contact 334.

Figure 14A:
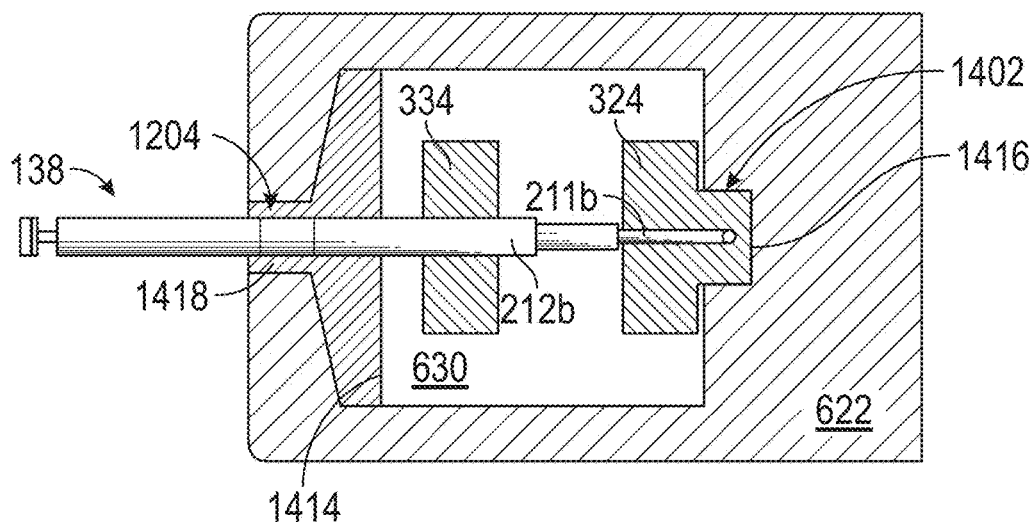
FIG. 14A illustrates a plan view of an example of the second type of sensor bend of FIG. 11B, according to some embodiments.
Figure 14B:
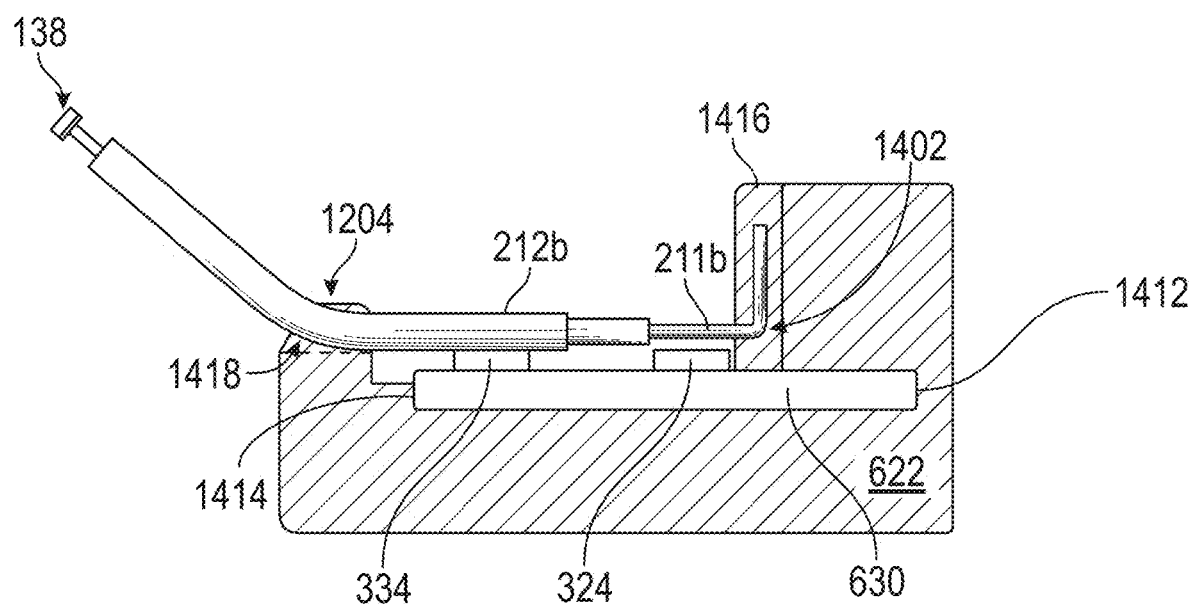
FIG. 14B illustrates a side cutaway view of the example of FIG. 14A.

Several example embodiments of the second type of sensor bend, as illustrated in FIG. 11B, will now be described in connection with FIGS. 14A-16 below. FIG. 14A shows a top view of an example arrangement including a sensor bend 1402 that causes the proximal portion of sensor 138 to extend away from electronics assembly substrate 630 (e.g., out of plane), according to some embodiments. FIG. 14B illustrates a side, cutaway view of the arrangement of FIG. 14A. Discussion below references both figures. The figures illustrate lower housing 622 of wearable assembly 600, electronics assembly substrate 630 disposed on, or alternatively within, lower housing 622, and sensor 138, comprising a plurality of bends 1402, 1204, disposed on and electrically coupled to electronics assembly substrate 630.

Electronics assembly substrate 630 may comprise a PCB material such as FR4, although the present disclosure is not so-limited and any suitable PCB material is also contemplated. Electronics assembly substrate 630 further comprises a plurality of electrical contacts, for example, contacts 324, 334 as previously described in connection with at least FIG. 3D.

Sensor 138 is illustrated as having a first bend 1402 at a proximal portion of sensor 138 and second bend 1204, as previously described in connection with FIG. 12, at a medial or distal portion of sensor 138. A portion of the elongated body of sensor 138 distal of first bend 1302 extends substantially parallel to a plane of electronics assembly substrate 630 and a portion of the elongated body proximal to first bend 1302 extends substantially perpendicular to the plane of electronics assembly substrate 630 and away from electronics assembly substrate 630. In some embodiments, the first bend 1402 occurs along the working electrode contact 211b.

Lower housing 622 may further comprise a molded geometry comprising one or more features configured to support electronics assembly substrate 630 and/or sensor 138 at or near each of the first bend 1402 and second bend 1204. For example, electronics assembly substrate 630 can be configured to rest on a portion of lower housing 622. Lower housing 622 can further comprise one or more ridges, recesses, or surfaces 1412, 1414 configured to abut one or more respective edges (e.g., lateral edges) of electronics assembly substrate 630. Among other advantages, the one or more ridges, recesses, or surfaces 1412, 1414 provide for more accurate placement of electronics assembly substrate 630 with respect to lower housing 622.

In addition, and/or alternative, lower housing 622 can comprise a recess 1416 in a sidewall of lower housing 622 immediately adjacent contact 324 that allows for the proximal portion of sensor 138 to extend substantially perpendicularly away from and with respect to electronics assembly substrate 630 and at least partially within the recess 1416. Among other advantages, recess 1416 establishes mechanical positioning of sensor 138 before conductive connections (e.g., epoxy, solder, or the like) are applied to electrically connect contacts 211b and 324 and to electrically connect contacts 212b and 334, for example.

In addition, and/or alternative, lower housing 622 can comprise a notch 1418 configured to align a medial and/or distal portion of sensor 138 at, near or adjacent to second bend 1204. Among other advantages, notch 1418 provides additional alignment and restricts undesirable movement of sensor 138 prior to and after securing sensor 138 to electronics assembly substrate 630 and/or to lower housing 622.

In some embodiments, a bend of the second type (e.g., substantially parallel to a plane of electronics assembly substrate 630 to substantially perpendicular to and away from electronics assembly substrate 630) may be utilized to purposefully exploit the elastic properties of sensor 138 to generate a biasing or retention force against one or more features of electronics assembly substrate 630 and/or of lower housing 622. Examples are described below in connection with FIGS. 15 and 16.

Figure 15:
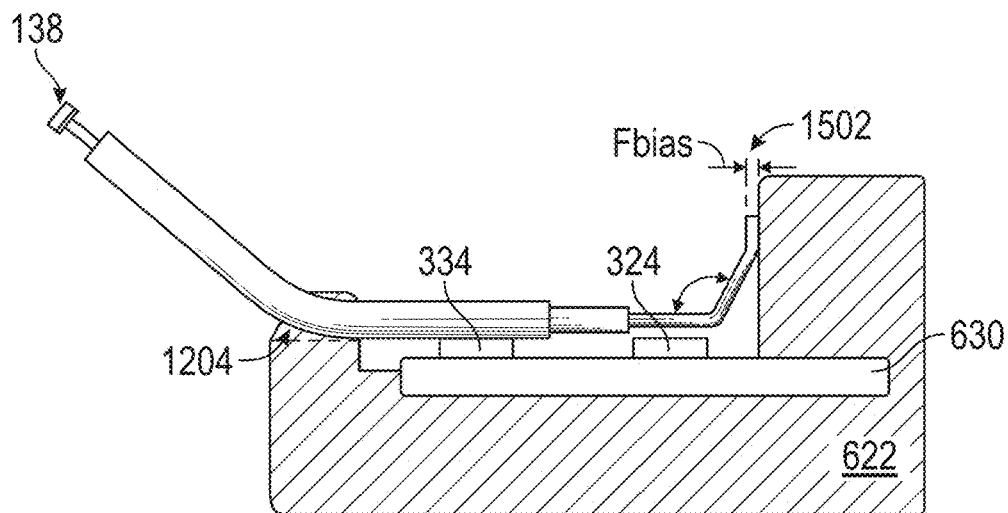
FIG. 15 illustrates a side cutaway view of another example of the second type of sensor bend of FIG. 11B, according to some embodiments.

FIG. 15 shows a side, cutaway view of an example arrangement including a sensor bend 1502 that causes the proximal portion of sensor 138 to extend away from electronics assembly substrate 630 while simultaneously presenting a biasing force against lower housing 622, according to some embodiments. For ease of illustration and discussion, contacts on sensor 138 and on electronics assembly substrate 630 are not shown.

Sensor 138 is illustrated as having a first bend 1502 at a proximal portion of sensor 138 and second bend 1204, as previously described in connection with FIG. 12, at a medial or distal portion of sensor 138. The first bend 1502 may cause a direction of extension of the proximal portion of sensor 138 to transition, by a desired angle (e.g., between 90-180°, from substantially in-plane with electronics assembly substrate 630 to substantially angled out-of-plane with respect to electronics assembly substrate 630 such that at least some of the proximal portion of sensor 138 contacts and exerts a biasing force against a sidewall of lower housing 622, for example, against a sidewall within recess 1416 as previously described in connection with FIG. 14. This will cause the sidewall of lower housing 622 to exert an equal but opposite biasing force on the proximal portion of sensor 138, thereby securing sensor 138 in a desired orientation and position before conductive connections (e.g., epoxy, solder, or the like) are applied between or to the proximal portion of sensor 138 and contact 324 and between or to an appropriate portion of sensor 138 and contact 334.

Figure 16A:
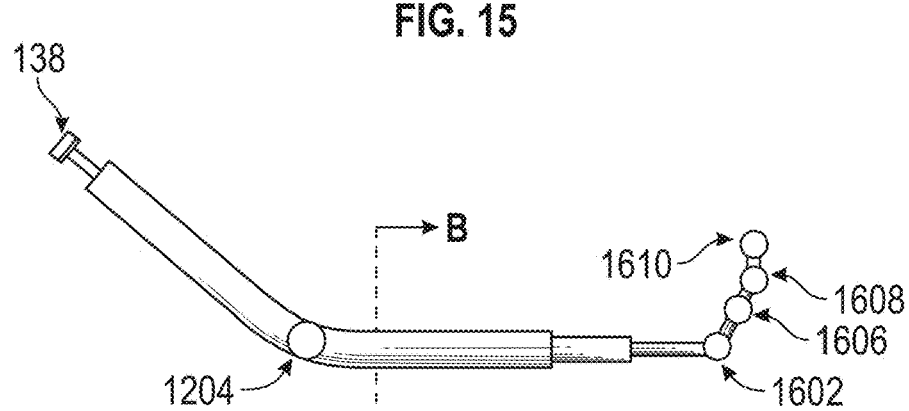
FIG. 16A illustrates a first side cutaway view of yet another example of the second type of sensor bend of FIG. 11B, according to some embodiments.
Figure 16B:
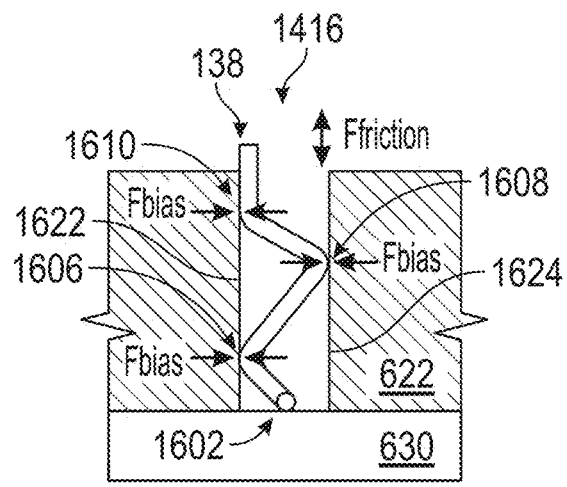
FIG. 16B illustrates a second side cutaway view of FIG. 16A as viewed along the cut line B-B', according to some embodiments.

FIG. 16A shows a first side view of an example arrangement including multiple sensor bends 1602, 1204, 1606, 1608, 1610, at least some of which cause biasing forces against portions of lower housing 622, according to some embodiments. FIG. 16B shows a second side view of the example arrangement of FIG. 16A taken along the section line B-B' in FIG. 16A.

Sensor 138 is illustrated as having a first bend 1602 at a proximal portion of sensor 138, one or more additional bends 1606, 1608, 1610 proximal to the first bend 1602, and the bend 1204, as previously described in connection with FIG. 12, at a medial or distal portion of sensor 138 that is distal to bends 1602, 1606, 1608, 1610. The first bend 1602 may cause a direction of extension of the proximal portion of sensor 138 to transition, by a desired angle (e.g., approximately 90.degree., from substantially parallel to the plane of electronics assembly substrate 630 to substantially perpendicular to the plane of and away from electronics assembly substrate 630. In some embodiments, at least some portions of sensor 138 proximal to first bend 1602 may be disposed within a recess in a sidewall of lower housing 622, for example, recess 1416 as previously described in connection with FIG. 14.

As shown in FIG. 16B, the one or more additional bends 1606, 1608, 1610 cause portions of sensor 138 proximal to first bend 1602 to extend at angles with respect to opposing sidewalls 1622, 1624 of recess 1416. Accordingly, sensor 138 contacts and exerts biasing forces against the sidewalls 1622, 1624 of recess 1416 at least at the locations of bends 1606, 1608, 1610. Exertion of such biasing forces by sensor 138 will cause the sidewalls 1622, 1624 to exert equal but opposite biasing forces on the proximal portion of sensor

138. The result of these biasing forces can secure sensor 138 in a desired orientation and position before conductive connections (e.g., epoxy, solder, or the like) are applied between or to an appropriate portion of sensor 138 and contact 324 and between or to another appropriate portion of sensor 138 and contact 334 (not shown in FIGS. 16A-16B). As shown, the biasing forces Fb.sub.ias, exerted normal to the points of contact between sensor 138 and the sidewalls 1622, 1624, will cause a frictional force F.sub.friction in a direction parallel to sidewalls 1622 at the points of contact between sensor 138 and the sidewalls 1622, 1624 to resist movement of sensor 138 with respect to lower housing 622 and electronics assembly substrate 630. Among other advantages, the one or more additional bends 1606, 1608, 1610 provide additional alignment and restrict undesirable movement or rotation of, and centerline constraint for, sensor 138 prior to and after securing sensor 138 to electronics assembly substrate 630 and/or to lower housing 622.

Figure 17:
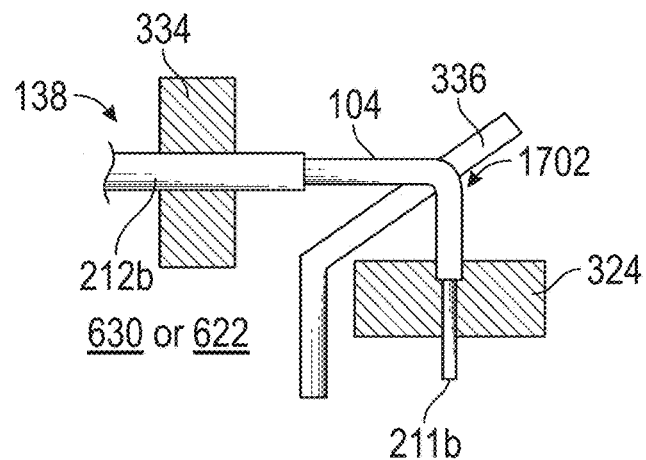
FIG. 17 illustrates a plan view of an example of the third type of sensor bend of FIG. 11C, according to some embodiments.

Several example embodiments of the third type of sensor bend, as illustrated in FIG. 11C, will now be described in connection with FIGS. 17-20 below. FIG. 17 shows a top view of an example arrangement including a sensor bend 1702 that causes the proximal portion of sensor 138 to maintain extension substantially in-plane with respect to electronics assembly substrate 630, according to some embodiments. FIG. 17 illustrates electronics assembly substrate 630 and sensor 138, comprising at least bend 1702, disposed on and electrically coupled to electronics assembly substrate 630.

Electronics assembly substrate 630 may comprise a PCB material such as FR4, although the present disclosure is not so-limited and any suitable PCB material is also contemplated. Electronics assembly substrate 630 further comprises a plurality of electrical contacts, for example, contacts 324, 334, 336 as previously described in connection with at least FIG. 3D. As previously described, contact 336 may comprise a guard trace.

Sensor 138 is illustrated as having at least a first bend 1702 at a proximal portion of sensor 138. The first bend 1702 may cause a direction of extension of the proximal portion of sensor 138 to transition from substantially in-plane with electronics assembly substrate 630, by any desired in-plane angle (shown as approximately 90° in FIG. 17), such that at least a portion of sensor 138 proximal to the first bend 1702 remains substantially in-plane with electronics assembly substrate 630. In some embodiments, the first bend 1702 occurs along the insulation layer 104, which in some embodiments may comprise polyurethane or any other suitable electrical insulator. Although not shown in FIG. 17, sensor 138 may comprise any number of additional bends, for example second bend 1204, as previously described in connection with FIG. 12, at a medial or distal portion of sensor 138.

Contact 212b of sensor 138 may be in mechanical and electrical contact with contact 334. Insulation layer 104 may be in mechanical and electrical contact with contact 336. Contact 211b of sensor 138 may be in mechanical and electrical contact with contact 324. Among other advantages, the first bend 1702, by redirecting at least a first portion of sensor 138 between the contact 211b and the contact 212b to extend in a different, in-plane direction compared to a second portion of sensor 138 between the contact 211b and the contact 212b, allows the contacts 211b, 212b to be separated by a greater linear distance along sensor 138 and so separated by a greater linear length of insulation layer 104. This may be at least partly a function of the limited dimension of electronics assembly substrate 630 in any single direction. By causing portions of sensor 138 to extend in at least two different in-plane directions with respect to electronics assembly substrate 630, the contacts 211b, 212b may be separated by a greater linear distance along sensor 138. In addition, the first bend 1702, by causing portions of sensor 138 to extend in at least two different in-plane directions with respect to electronics assembly substrate 630, provides at least three in-plane points of contact (e.g., contacts 324, 334, 336) that create a more easily handled shape and that can mimic a flat surface for which sensor 138 can rest.

In some embodiments, a bend of the third type (e.g., changing a direction of extension of at least a portion of sensor 138 while remaining substantially in-plane with electronics assembly substrate 630) may be utilized to purposefully exploit the elastic properties of sensor 138 to generate a biasing or retention force against one or more features of electronics assembly substrate 630 and/or of wearable assembly 600. Examples are described below in connection with FIGS. 18-20.

Figure 18:
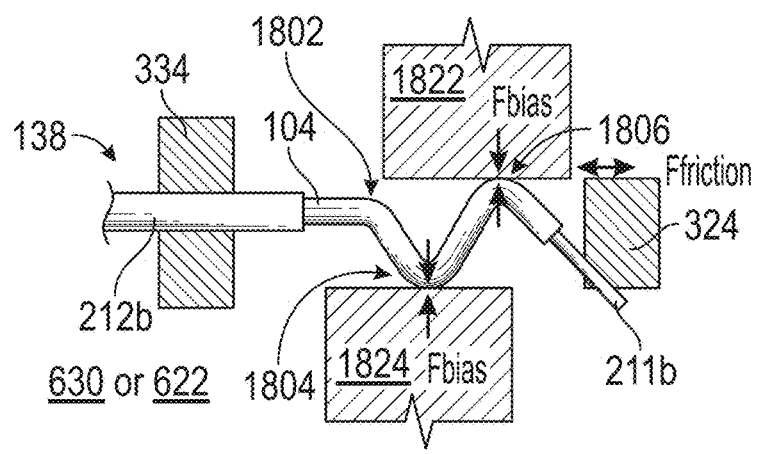
FIG. 18 illustrates a plan view of another example of the third type of sensor bend of FIG. 11C, according to some embodiments.

FIG. 18 shows a top view of an example arrangement including multiple sensor bends 1802, 1804, 1806, at least some of which cause a biasing force against portions 1822, 1824 of lower housing 622 or electronics assembly substrate 630, according to some embodiments.

Sensor 138 is illustrated as having a first bend 1802 at a proximal portion of sensor 138 and one or more additional bends 1804, 1806 proximal to the first bend 1802. Although not shown in FIG. 18, sensor 138 may further comprise the bend 1204, as previously described in connection with FIG. 12, at a medial or distal portion of sensor 138 that is distal to bends 1802, 1804, 1806.

The one or more additional bends 1804, 1806 cause portions of sensor 138 proximal to first bend 1802 to extend at angles with respect to opposing sidewalls 1822, 1824 of lower housing 622 and/or of electronics assembly substrate 630 such that sensor 138 contacts and exerts biasing forces $Fb_{ias}$ against the sidewalls 1822, 1824 at least at the locations of bends 1804, 1806, which will cause the sidewalls 1822, 1824 to exert equal but opposite biasing forces on the proximal portion of sensor 138, thereby securing sensor 138 in a desired orientation and position before conductive connections (e.g., epoxy, solder, or the like) are applied between or to contacts 211b and 324 and between or to contacts 212b and 334.

Similar to that previously described in connection with FIG. 16, the biasing forces $F_{bias}$, exerted normal to the points of contact between sensor 138 and the sidewalls 1822, 1824, will cause a frictional force Ffnction in a direction parallel to sidewalls 1822, 1824 at the points of contact between sensor 138 and the sidewalls 1822, 1824 to resist movement of sensor 138 with respect to lower housing 622 and electronics assembly substrate 630. Among other advantages, the one or more additional bends 1804, 1806 provide additional alignment and restrict undesirable movement or rotation of, and centerline constraint for, sensor 138 prior to and after securing sensor 138 to electronics assembly substrate 630 and/or to lower housing 622.

Figure 19:
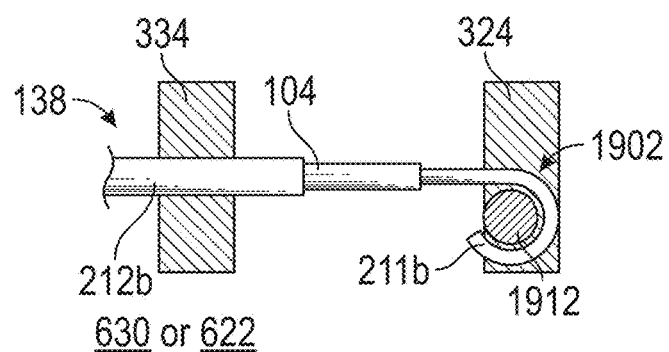
FIG. 19 illustrates a plan view of yet another example of the third type of sensor bend of FIG. 11C, according to some embodiments.

FIG. 19 shows a top view of an example arrangement including at least one sensor bend 1902, which substantially immobilizes or anchors sensor 138 to a pin or post 1912 of or fabricated on a portion of the housing 128, for example lower housing 622 or electronics assembly substrate 630, according to some embodiments.

Sensor 138 is illustrated as having a first bend 1902 at a proximal portion of sensor 138. In some embodiments, the first bend 1902 is an at least partially circumferential bend configured to wrap a proximal portion of the sensor at least partway around a pin or post 1912, which may comprise a part of contact 324 which can be a part of electronics assembly substrate 630. The first bend 1902 may change a direction of extension of at least a portion of sensor 138 while remaining substantially in-plane with electronics assembly substrate 630.

Among other advantages, the first bend 1902, extending at least partially around a circumference or perimeter of pin or post 1912, secures sensor 138 in a desired orientation and position before conductive connections (e.g., epoxy, solder, or the like) are applied between or to contacts 211b and 324 and between or to contacts 212b and 334. Accordingly, the arrangement of FIG. 19 also provides alignment and restricts undesirable movement or rotation of, and centerline constraint for, sensor 138 prior to and after securing sensor 138 to electronics assembly substrate 630 and/or to lower housing 622.

Although not shown in FIG. 19, sensor 138 may further comprise the bend 1204, as previously described in connection with FIG. 12, at a medial or distal portion of sensor 138 that is distal to bend 1902.

Figure 20:
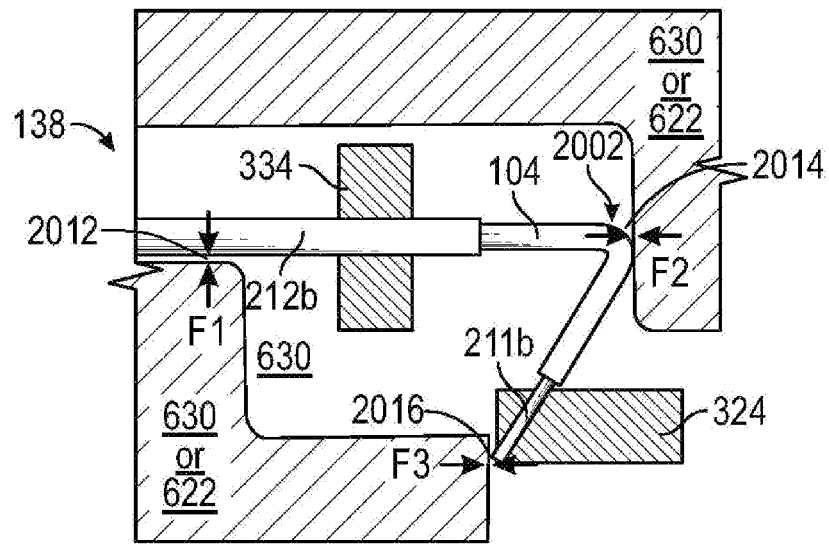
FIG. 20 illustrates a plan view of yet another example of the third type of sensor bend of FIG. 11C, according to some embodiments.

FIG. 20 shows a top view of an example arrangement including at least one sensor bend 2002, which causes at least one biasing force F1, F2, F3 against one or more portions 2012, 2014, 2016 of lower housing 622 or of electronics assembly substrate 630, according to some embodiments.

Sensor 138 is illustrated as having a first bend 2002 at a proximal portion of sensor 138. First bend 2002 causes portions of sensor 138 proximal to first bend 2002 to change a direction of extension of at least a portion of sensor 138 while remaining substantially parallel to the plane of electronics assembly substrate 630. For example, first bend 2002 is illustrated as occurring along the portion of sensor 138 where the insulated layer 104 is present and exposed. However, the present disclosure is not so limited and first bend 2002 can occur along any suitable portion of sensor 138. First bend 2002 is illustrated as having an angle of less than 90°. However, the present disclosure is not so-limited and any suitable bend angle may be utilized, depending on the particular context of the situation and the layout of the particular features of wearable assembly 600.

A first portion of sensor 138 may be configured to contact a first sidewall or other feature 2012 of lower housing 622 or of electronics assembly substrate 630. In FIG. 20, this first portion of sensor 138 is illustrated as a portion of the reference electrode or contact 212b. However, the present disclosure is not so-limited and any other portion of sensor 138 is also contemplated.

Sensor 138 may be configured to contact a second sidewall or other feature 2014 of lower housing 622 or of electronics assembly substrate 630 at the location of first bend 2002.

A second portion of sensor 138 may be configured to contact a third sidewall or other feature 2016 of lower housing 622 or of electronics assembly substrate 630. In FIG. 20, this third portion of sensor 138 is illustrated as a portion of the working electrode or contact 211b proximal of first bend 2002. However, the present disclosure is not so-limited and any other portion of sensor 138 is also contemplated.

In FIG. 20, a contacting surface of first sidewall 2012 and biasing force F1 are illustrated as facing substantially perpendicular to a direction of extension of the first portion of sensor 138 (e.g., the reference electrode) and substantially perpendicular to respective contacting surfaces of each of the second and third sidewalls 2014, 2016. However, the present disclosure is not so limited and the contacting surface of first sidewall 2012 can have any suitable orientation(s) with respect to any of the first portion of sensor 138 and/or the respective contacting surfaces of each of the second and third sidewalls 2014, 2016.

In FIG. 20, the respective contacting surfaces of the second and third sidewalls 2014, 2016 and biasing forces F2 and F3 are illustrated as facing in opposite directions. However, the present disclosure is not so-limited and the respective contacting surfaces of the second and third sidewalls 2014, 2016 and biasing forces F2 and F3 can have any suitable orientation(s) with respect to one another and/or with respect to any other features of wearable assembly 600.

Sensor 138 may be initially bent at first bend 2002 to an angle less than the ultimate angle illustrated in FIG. 20 or desired in actual implementation and then placed in the illustrated or desired orientation, thereby increasing the angle of first bend 2002 slightly beyond the initial bend angle. As illustrated in FIG. 20, due to the elastic and/or resilient properties of sensor 138, sensor 138 will exhibit a tendency to attempt to reduce the angle of first bend 2002 from the illustrated angle toward the initial bend angle. This tendency will cause sensor 138 to develop at least one biasing or retention force(s) F1, F2, F3 in directions substantially normal to and against the points of contact with the one or more respective sidewalls 2012, 2014, 2016 of electronics assembly substrate 630 and/or of lower housing 622.

For example, as illustrated, the tendency of sensor 138 to decrease the bend angle of first bend 2002 will cause a torque at first bend 2002 that pushes the second portion of sensor 138 against the contacting surface of the third sidewall 2016 with a force F3, producing an equal but opposite biasing force on the second portion of sensor 138. This opposite biasing force will push sensor 138 against the contacting surface of the second sidewall 2014 at first bend 2002 with a force F2, producing an equal but opposite biasing force on sensor 138 at first bend 2002.

The torque at first bend 2002 caused by the tendency of sensor 138 to decrease the bend angle of first bend 2002 will also push the first portion of sensor 138 against the contacting surface of first sidewall 2012 with the force F1, producing an equal but opposite biasing force on the first portion of sensor 138.

The biasing or retaining forces F1, F2, F3 will also cause orthogonal frictional forces (not shown) in respective directions parallel to the sidewalls 2012, 2014, 2016 at the points of contact that will further resist movement of sensor 138 with respect to lower housing 622 and electronics assembly substrate 630. Alone or in combination, these biasing, retaining and/or frictional forces act to secure sensor 138 in a desired orientation and position before conductive connections (e.g., epoxy, solder, or the like) are applied between or to contacts 212b and 324 and between or to contacts 211b and 334.

Among other advantages, first bend 2002 provides additional alignment and restricts undesirable movement or rotation of, and centerline constraint for, sensor 138 prior to and after securing sensor 138 to electronics assembly substrate 630 and/or to lower housing 622.

Utilizing Substrate Dams to Form Wells for Direct-to-Board Sensor Connection

With some sensor wire direct-to-board designs, conductive epoxies or other adhesive epoxies used at different locations to bond sensor 138 to the PCB (e.g., electronics assembly substrate 630) can bleed or run together, undesirably causing electrical shorts, or otherwise undesirably bleed or run along the sensor into adjacent areas. Several solutions are described below in connection with at least FIGS. 21A-27.

Figure 21A:
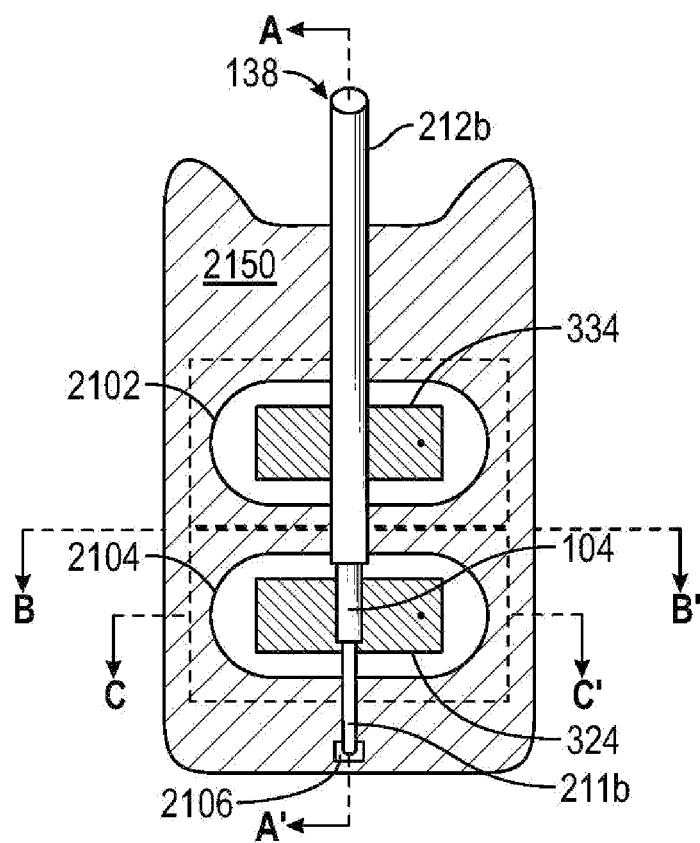
FIG. 21A illustrates a top view of a portion of a wearable assembly comprising a plurality of dams that form a plurality of wells for containing and preventing undesirable bleeding or migration of epoxy, according to some embodiments.
Figure 21B:
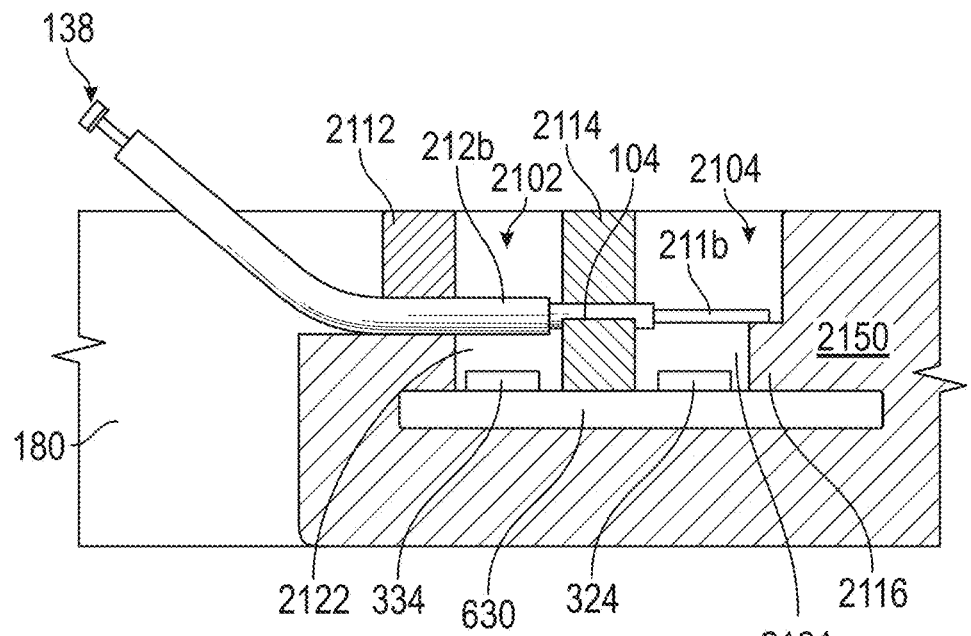
FIG. 21B illustrates a side cutaway view of the portion of the wearable assembly of FIG. 21A viewed along the cut line A-A', according to some embodiments.
Figure 21C:
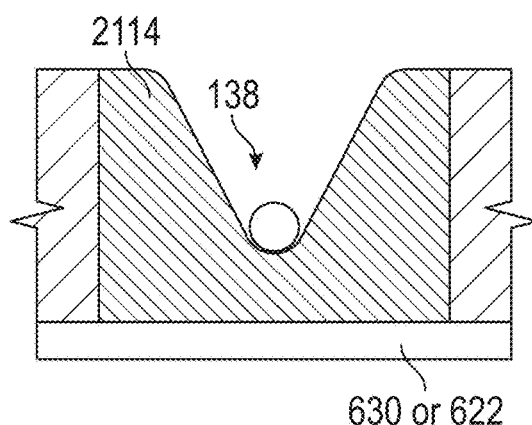
FIG. 21C illustrates another side cutaway view of the portion of the wearable assembly of FIG. 21A viewed along the cut line B-B', according to some embodiments.
Figure 21D:
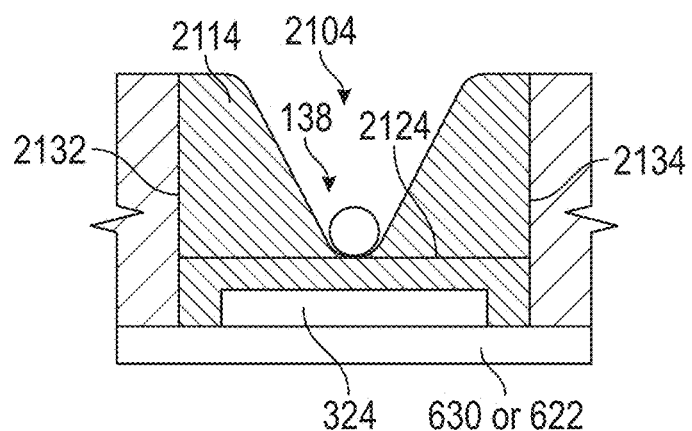
FIG. 21D illustrates another side cutaway view of the portion of the wearable assembly of FIG. 21A viewed along the cut line C-C', according to some embodiments.

FIG. 21A shows a top view of a portion of a wearable assembly 600 comprising a plurality of dams 2112, 2114, 2116 that form a plurality of wells 2102, 2104 for containing and preventing undesirable bleeding or migration of epoxy 2122, 2124, according to some embodiments. FIGS. 21B, 21C and 21D each show side cutaway views of the portion of wearable assembly 600 illustrated in FIG. 21A taken along cut-lines A-A', B-B' and C-C', respectively. The portion of wearable assembly 600 shown in FIGS. 21A-21D may be fabricated according to any suitable process, for example low pressure overmolding of electronics assembly substrate 630 and/or of lower housing 622. Further discussion follows with reference to each of FIGS. 21A-21D.

FIG. 21B illustrates electronics assembly substrate 630 comprising contacts 324, 334 as previously described in connection with at least FIG. 3D. An overmold structure 2150 may be formed on, over, around or as an integral part of electronics assembly substrate 630, for example utilizing a low-pressure overmolding process. Such a low-pressure overmolding process can allow full shut off around electronics assembly substrate 630, thereby sealing portions of electronics assembly substrate 630 from moisture ingress and leaving less of electronics assembly substrate 630 exposed for subsequent potting processes.

Overmold structure 2150 comprises a plurality of dams 2112, 2114, 2116 spaced adjacent to contacts 324, 334. Contacts 324 and 334 may each be a contact pad or plate disposed on electronics assembly substrate 630. In some embodiments, contacts 324 and 334 may be formed by gold plating. As shown, contacts 324 and 334 are rectangular shaped. In other embodiments, contacts 324 and 334 may be circular shaped, oval shaped, diamond shaped, rounded rectangular shaped, rounded diamond shaped, polygonal-shaped, or rounded polygonal shaped. As illustrated, first dam 2112 is disposed adjacent to a first side of contact 334. Second dam 2114 is disposed adjacent to a second side of contact 334 opposite the first side, between contacts, 324, 334, and adjacent to a first side of contact 324. Third dam 2116 is disposed adjacent to a second side of contact 324 opposite the first side. Accordingly, first and second dams 2112, 2114 define a first well 2102 within which contact 334 is disposed, while second and third dams 2114, 2116 define a second well 2104 within which contact 324 is disposed. As shown in FIG. 21D, sidewalls 2132 and 2134, disposed on opposite sides of contact 324, form the remaining walls of second well 2104. While not explicitly shown and labeled in FIGS. 21A-21D, a similar pair of sidewalls, are disposed on opposite sides of contact 334 thereby forming the remaining walls of first well 2102.

Once wells 2102, 2104 are formed, conductive epoxy 2122, 2124 can be deposited over contacts 324, 334 within wells 2102, 2104 in preparation for sensor 138 placement.

As shown in FIGS. 21C and 21D, at least one of dams 2112, 2114, 2116 can have a sloped cross-section, as viewed perpendicular to cut lines B-B' or C-C'. For example, dams 2112, 2114, 2116 can have a triangularly-, parabolically-, semi-circularly-, hyperbolically- or otherwise-recessed cross-section having a lowest point substantially equidistant from corresponding sidewalls of the respective wells along the cross-section (e.g., sidewalls 2132, 2134 for second well 2104), or at any other desired location along the cross-section(s). Respective portions of sensor 138 are configured to rest substantially at this lowest point of the recess or cross-section of each of dams 2112, 2114, 2116 due to their sloped or notched character. Accordingly, dams 2112, 2114, 2116 not only define wells 2102, 2104 but also guide the respective portions of sensor 138 to desired locations before they are secured in place.

In some embodiments, one or more of the dams (e.g., third dam 2116 as shown in FIGS. 21A-21B) may have a substantially flat cross-section, rather than the sloped cross-section described above. For example, where first and second dams 2112, 2114 have the above-described sloped cross-section and adequately constrain at least lateral positioning of sensor 138, third dam 2116 need not have the sloped cross-section and the flat cross-section may merely serve as a platform on which the proximal end of sensor 138 rests.

As shown in at least FIGS. 21B and 21D, epoxy 2122, 2124 can be deposited in each of wells 2102, 2104 at least to a minimum height. In some embodiments, such a minimum height is sufficiently large that respective portions of sensor 138 physically and electrically contact at least the top surface of epoxy 2122, 2124 when sensor 138 is disposed transversely across dams 2112, 2114, 2116, as shown in FIG. 21A. For example, contact 212b (of a reference electrode) can contact conductive epoxy 2122 disposed on contact 334 in first well 2102, while contact 211b (of a working electrode) can contact conductive epoxy 2124 disposed on contact 324 in second well 2104. A portion of sensor 138 distal to the portion of contact 212b contacting conductive epoxy 2122 can rest on first dam 2112, insulation layer 104 of sensor 138 can rest on second dam 2114, and a portion of sensor 138 proximal to the portion of contact 211b contacting conductive epoxy 2124 can rest on third dam 2116.

As shown in FIG. 21B, conductive epoxy 2122 may fill in a void in first well 2102 between contact 334 of electronics assembly substrate 630 and contact 212b of sensor 138 (e.g. reference electrode). As such, conductive epoxy 2122 may physically separate contact 334 and contact 212b. One advantage of this separation may be the reduction of signal noise or signal shift of sensor 138 that can occur when contact 334 and contact 212b are in physical contact. It is contemplated that, in some instances, the material of contact 212b of the reference electrode may galvanically react with the material of contact 334 of electronics assembly substrate 630. For example, contact 212b may comprise silver and silver chloride and contact 334 may comprise gold, nickel, and copper. It is contemplated that the galvanic interaction between gold and silver/silver chloride or copper and silver/silver chloride may result in corrosion of contact 334. Thus, filling in the space between contact 334 and contact 212b with conductive epoxy 2122 may reduce corrosion of contact 334. In some embodiments, contact 334 may have a channel (not shown) extending through a middle of the contact to allow for conductive epoxy to be deposited. In other embodiments, contact 334 may have an intermediate layer (not shown) disposed over contact 334 that separates contact 334 and contact 212b. In such embodiments, the intermediate layer may comprise plastic, epoxy, or a composite material such as FR4. It is also contemplated that in embodiments where contact 334 is in physical contact with contact 212b (for example, FIG. 15), a carbon conductive ink may be disposed over an underlying copper layer of contact 334. The carbon conductive ink would replace the more common gold layer in which it is contemplated that the carbon in the carbon conductive ink has lower galvanic potential which would increase resistance to corrosion. In some embodiments, a corrosion inhibiter layer may be formed on contact 334 to increase resistance to corrosion. It is also contemplated that any of the above features and techniques may be applied to contact 324 as well.

In some embodiments where sensor 138 is attached directly to electronics assembly substrate 630 without utilizing a separate sensor carrier, sensor 138 may be handed off to wearable assembly 600 from a placement gripper during manufacture. Such a "hand-off" method should maintain the position of sensor 138 as placed by such a placement gripper while an epoxy, for example an ultraviolet curing epoxy, can be used to seal or adhere sensor 138 to electronics assembly substrate 630. However, this epoxy must be prevented from running along sensor 138 into adjacent areas, for example an area in which through-hole 180 of on-skin sensor assembly 500, 600 resides. In addition, strain relief may be desirable outside of the encapsulant to reduce wire strain and maintain the position of sensor 138 against the mounting surface.

An additional or alternative solution that not only holds sensor 138 as placed by such a placement gripper while epoxy is being cured, but also prevents wicking of the epoxy along sensor 138 while simultaneously providing strain relief to sensor 138 is described in connection with FIGS. 22-27 and 40A-41 below. Pockets of varying geometry, configured to hold a predetermined amount of epoxy for securing sensor 138, are utilized in combination with step-up, step-down or flush transitions from the pockets to adjacent areas, the transitions specifically designed as "fluidic stops" that prevent epoxy deposited in the pockets from bleeding, wicking or otherwise running beyond the boundaries of the pocket and into the adjacent areas or onto the sensor are described. In some embodiments, the pockets, transitions, and adjacent areas may be formed utilizing a low-pressure molding process or any other suitable process. In some embodiments, the pockets and their adjacent areas are continuous with respect to one another, e.g., the adjacent areas are disposed immediately adjacent to their respective pocket without features, other than the transitions, therebetween. In some embodiments, the epoxy is composed of a non-conductive material. In some embodiments, the epoxy is composed of a conductive material.

Figure 22:
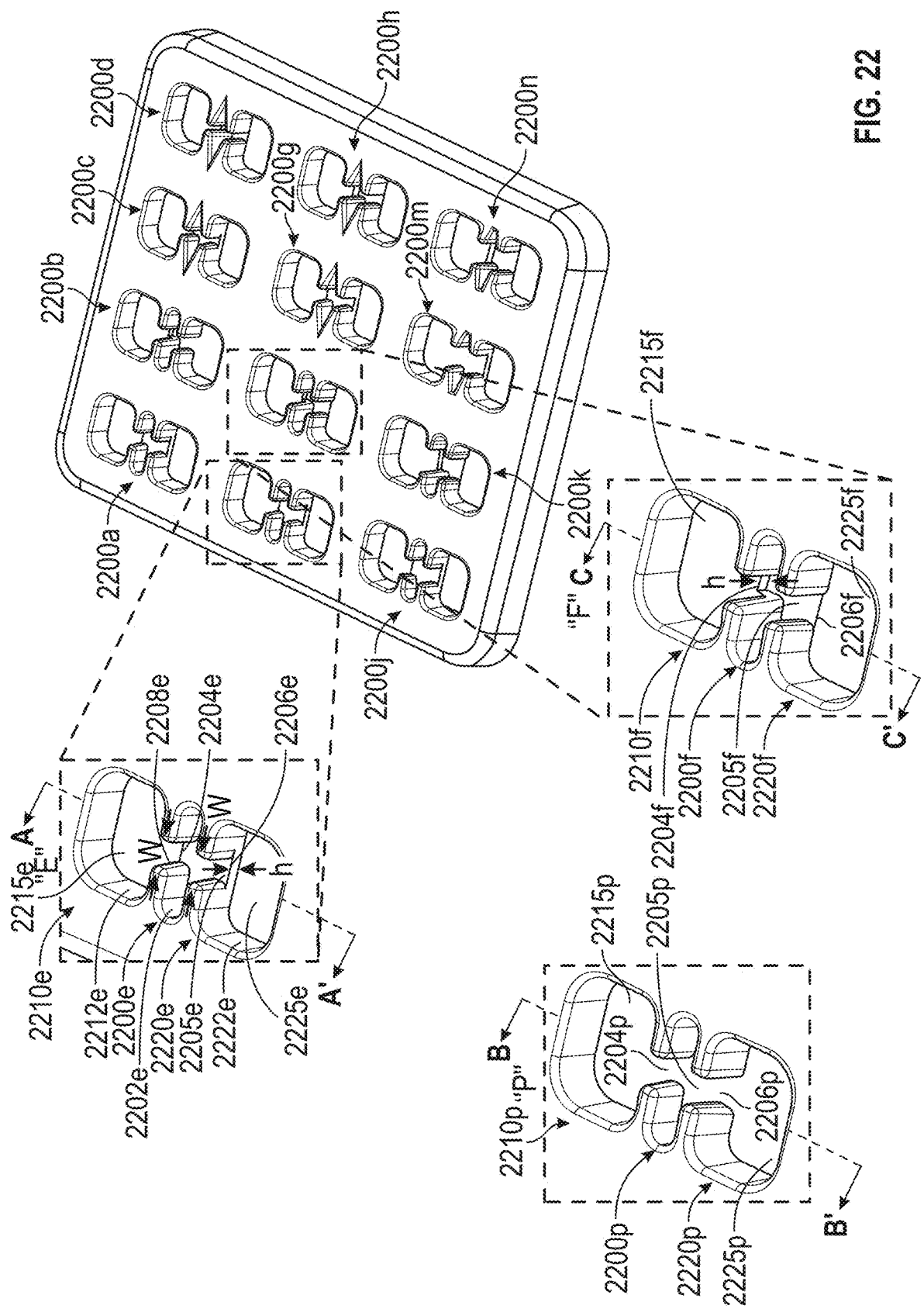
FIG. 22 illustrates a perspective view of a plurality of pockets having varying geometries for securing a sensor utilizing epoxy, in combination with step-up, step-down or flush transitions of varying widths for preventing the epoxy from bleeding to adjacent areas, according to some embodiments.

FIG. 22 shows a perspective view of a plurality of pockets having varying geometries in combination with step-up, step-down or flush transitions of varying widths to adjacent areas, according to some embodiments. FIG. 23 illustrates a plan view of several example geometries for the pockets of FIG. 22. FIG. 24 illustrates a set of side views of an example step-up transition as would be viewed along the cut-lines A-A' in FIG. 22, an example flush transition as would be viewed along the cut-line B-B' in FIG. 22, and an example step-down transition as would be viewed along the cut-line C-C' in FIG. 22. FIG. 25 illustrates a set of side views viewed along the cut-lines A-A', B-B' and C-C' in FIG. 24, further illustrating an example width "w" of the transitions and example orientations of the sidewalls of the pockets and/or adjacent areas. The pockets, transitions and adjacent areas will now be discussed in combination with FIGS. 22-25.

FIG. 22 illustrates a plurality of pockets 2200a-2200p, each pocket having a corresponding adjacent area on either side. Each of the pockets 2200a-2200p are illustrated as having a different combination of pocket geometry, type of transition between the pocket and the adjacent areas, and transition widths "w." The callouts "E," "F" and "P" in FIG. 22 illustrate several of the aspects of these different combinations, which will be described in more detail in connection with FIGS. 23-25. It should be understood that any of the pockets, adjacent areas, and/or transitions therebetween, described in connection with at least FIGS. 22-25, can be implemented into the housings of any of wearable assemblies 500, 600 as previously described in connection with at least FIGS. 5A-6C.

As shown in callout "E," a first adjacent area 2210e is disposed at a first side of pocket 2200e and a second adjacent area 2220e is disposed at a second side of pocket 2200e opposite the first side. Callout "E" further illustrates a first transition 2204e between pocket 2200e and the first adjacent area 2210e and a second transition 2206e between pocket 2200e and the second adjacent area 2220e. First and second transitions 2204e, 2206e may comprise the structure and/or geometry that separates respective bases 2215e, 2225e of first and second adjacent areas 2210e, 2220e from a base 2205e of pocket 2200e. In callout "E" the first and second transitions 2204e, 2206e are shown as "step-down" transitions, so-called because respective bases 2215e, 2225e of each of adjacent areas 2210e, 2220e are disposed at a lower height than base 2205e of pocket 2200e by an amount "h." An example value for "h" is 0.5 mm, however, the present disclosure is not so limited and any suitable value for "h" is also contemplated. Each of the transitions 2204e, 2206e is also shown as having a width "w." In some embodiments, width "w" may be defined as a separation distance between sidewalls of 2208e of a particular transition 2204e, 2206e. An example range of values for "w" is 0.5-2.0 mm, however, the present disclosure is not so limited and any suitable value or range for "w" is also contemplated. The first adjacent area 2210e has sidewalls 2212e. The second adjacent area 2220e has sidewalls 2222e, the pocket has sidewalls 2202e, and the sidewalls at the first and second transitions 2204e, 2206e are illustrated as 2208e. Callout "E" further illustrates a cut-line A-A' along which the "step down" view illustrated in FIG. 24 may correspond.

Callout "P" illustrates pocket 2200p having a first transition 2204p to a first adjacent area 2210p and a second transition 2206p to a second adjacent area 2220p. The arrangement in callout "P" is substantially similar to the arrangement in callout "E" except first and second transitions 2204p, 2206p are illustrated as "flush" transitions, so-called because respective bases 2215p, 2225p of each of adjacent areas 2210p, 2220p are disposed at the same height as a base 2205p of pocket 2200p. Callout "P" further illustrates a cut-line B-B' along which the "flush" view illustrated in FIG. 24 may correspond.

Callout "F" illustrates pocket 2200f having a first transition 2204f to a first adjacent area 2210f and a second transition 2206f to a second adjacent area 2220f. The arrangement in callout "F" is substantially similar to the arrangement in callout "E" except first and second transitions 2204f, 2206f are illustrated as "step-up" transitions, so-called because respective bases 2215f, 2225f of each of adjacent areas 2210f, 2220f are disposed at an elevated height compared to a base 2205f of pocket 2200f by an amount "h." An example value for "h" is 0.5 mm, however, the present disclosure is not so limited and any suitable value for "h" is also contemplated. Callout "F" further illustrates a cut-line C-C' along which the "step up" view illustrated in FIG. 24 may correspond.

As illustrated in FIG. 23, such pockets may have any one of several geometries. In some embodiments, a substantially rectangular pocket 2300a may be utilized. The sidewalls of rectangular pocket 2300a are shown as substantially planar such that they meet one another to form sharp, angled corners.

In some other embodiments, a substantially rounded rectangular pocket 2300b may be utilized. Portions of the sidewalls of rounded rectangular pocket 2300b are shown as substantially planar, while other portions of the sidewalls, connecting the substantially planar portions, are curved such that sharp, angled corners are not formed. Pockets 2200a, 2200b, 2200e, 2200f, 2200j, 2200k and 2200p of FIG. 22 are illustrated as having such a rounded rectangular geometry.

In yet other embodiments, a substantially triangular or diamond-shaped pocket 2300c may be utilized. The sidewalls of triangular or diamond-shaped pocket 2300b are shown as substantially planar such that they meet one another to form sharp, angled corners. Pockets 2200c, 2200d, 2200g, and 2200h of FIG. 22 are illustrated as having such a triangular or diamond-shaped geometry.

In yet other embodiments, a substantially rounded triangular or diamond-shaped pocket (not shown) may be utilized. Similar to the rounded rectangular pocket 2300b, portions of the sidewalls of rounded triangular or diamond-shaped pocket can be substantially planar, while other portions of the sidewalls, connecting the substantially planar portions, are curved such that sharp, angled corners are not formed.

In yet other embodiments, a substantially polygonal pocket 2300d may be utilized. The sidewalls of polygonal pocket 2300d are shown as substantially planar such that they meet one another to form sharp corners. Pockets 2200m and 2200n of FIG. 22 are illustrated as having such a polygonal geometry.

In yet other embodiments, a substantially rounded polygonal pocket (not shown) may be utilized. Similar to the rounded rectangular pocket 2300b, portions of the sidewalls of rounded polygonal pocket can be substantially planar, while other portions of the sidewalls, connecting the substantially planar portions, are curved such that sharp, angled corners are not formed.

In addition, although the above geometries have been described in connection with the pockets themselves, the present disclosure also contemplates that such geometries may be applied to any of the adjacent areas as well. For example, while the adjacent areas illustrated in FIG. 22 are shown as having rounded square or rectangular geometries, any other suitable geometry, as described above or elsewhere in this disclosure, may also be applied to the adjacent areas, including any suitable variable shape as a particular context may require or desire.

Figure 30A:
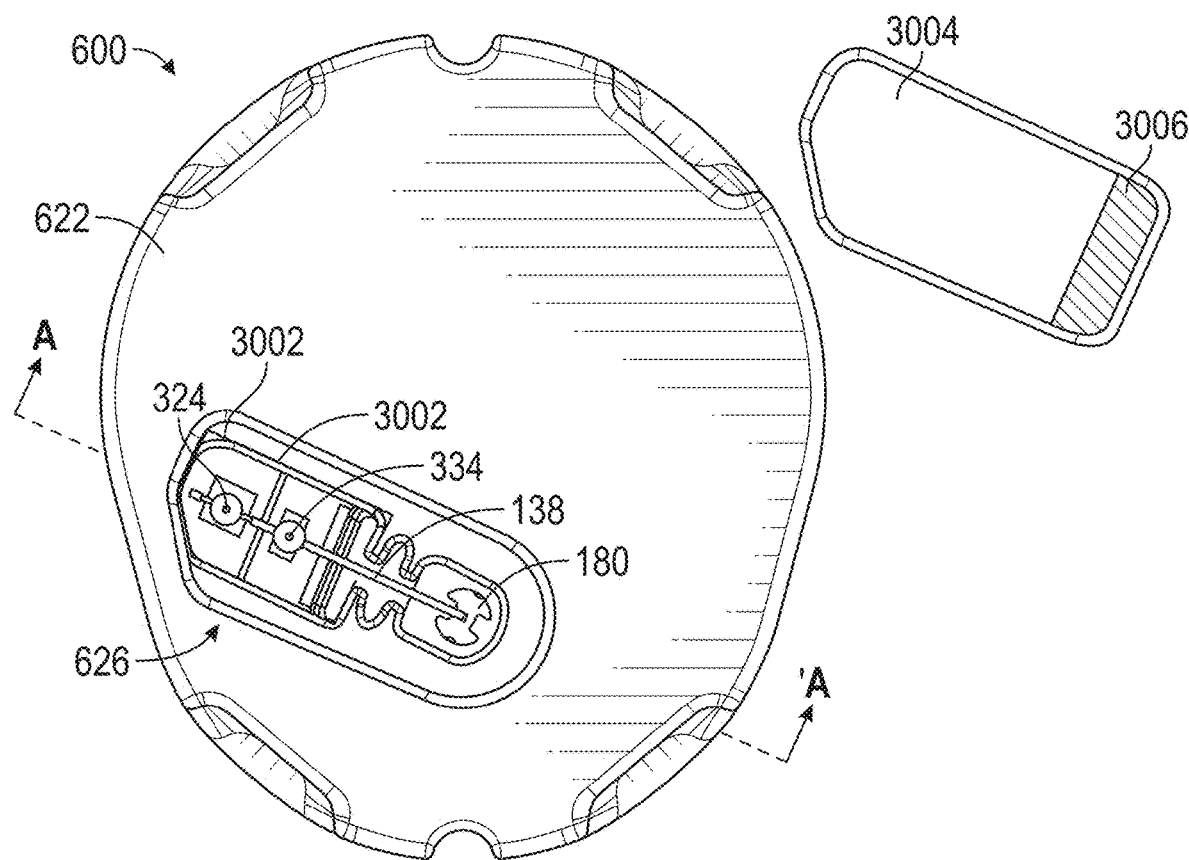
FIG. 30A illustrates a plan view of a wearable assembly having a heat-sealable thermoplastic elastomer and a mating cap having the heat-sealable thermoplastic elastomer, according to some embodiments.

As illustrated in FIG. 24, pockets may also have any one of several types of transitions to adjacent areas, e.g., fluidic stops. For example, the "Step Down" embodiment shows a sidewall 2412a of a first adjacent area 2410a, a sidewall 2402a of a pocket 2400a, a sidewall 2422a of a second adjacent area 2420a, and sidewalls 2408a at first and second transition areas 2404a, 2406a. Respective bases 2415a, 2425a of first and second adjacent areas 2410a, 2420a are illustrated as disposed at a lower height than a base 2405a of pocket 2400a by an amount "h." An example value for "h" is 0.5 mm, however, the present disclosure is not so limited and any suitable value for "h" is also contemplated. As illustrated, when epoxy 2430a is disposed on base 2405a of pocket 2400a, first and second step-down transitions 2404a and 2406a can inhibit or prevent epoxy 2430a from running into first and second adjacent areas 2410a, 2420a due in part to the surface tension and surface energy of epoxy 2430a causing a downward-inflecting meniscus 2432a to form at first and second transitions 2404a, 2406a, which adheres to the edges of first and second transitions 2404a, 2406a. In some embodiments, the step-down height "h," as well as, in some cases the width "w" of transitions 2404a, 2406a, and/or the area or volume of pocket 2400a, may depend not only on the predetermined amount of epoxy 2430a applied, but also on the specific viscosity, surface energy and/or surface tension characteristics between epoxy 2430a, surrounding environment, and the surfaces of the pocket, sensor, dispensing tip, or any other contacting surfaces or fluids. Other factors include the surrounding geometry of the pocket and the surrounding environment (e.g., materials, temperature, or humidity.) This adhering effect of such "step down" transitions and its inhibition or prevention of epoxy 2430a running may run contrary to conventional wisdom, which could expect that such a "step down" transition would not adequately inhibit or prevent epoxy 2430a from running into first and second adjacent areas 2410a, 2420a. FIG. 6B and FIG. 30A both illustrate an example of step down transitions.

The "flush" embodiment of FIG. 24 shows a sidewall 2412b of a first adjacent area 2410ab, a sidewall 2402b of a pocket 2400b, a sidewall 2422b of a second adjacent area 2420b, and sidewalls 2408b at first and second transition areas 2404a, 2406b. Respective bases 2415b, 2425b of first and second adjacent areas 2410b, 2420b are illustrated as disposed at the same height as a base 2405b of pocket 2400b. As illustrated, when epoxy 2430b is disposed on base 2405b of pocket 2400b, first and second flush transitions 2404b and 2406b can prevent epoxy 2430b from running into first and second adjacent areas 2410b, 2420b due in part to the surface tension and surface energy of epoxy 2430b causing a meniscus 2432b to form at first and second transitions 2404a, 2406b. In addition, interactions between epoxy 2430b and transition sidewalls 2408b and the width "w" of the transitions (as will be described in more detail in connection with the orthogonal side views of FIG. 25) can also affect the tendency of epoxy 2430b to be retained within pocket 2400b by transitions 2404b, 2406b, with relatively narrower widths "w" potentially providing better retention of epoxy 2430b within pocket 2400b. This adhering effect of such "flush" transitions and its inhibition or prevention of epoxy 2430b running may run contrary to conventional wisdom, which could expect that such a "flush" transition would not adequately inhibit or prevent epoxy 2430b from running into first and second adjacent areas 2410b, 2420b.

The "step-up" embodiment of FIG. 24 shows a sidewall 2412c of a first adjacent area 2410c, a sidewall 2402c of a pocket 2400c, a sidewall 2422c of a second adjacent area 2420c, and sidewalls 2408c at first and second transition areas 2404a, 2406c. Respective bases 2415b, 2425b of first and second adjacent areas 2410c, 2420c are illustrated as disposed at an elevated height "h" compared to a base 2405c of pocket 2400c by an amount "h." An example value for "h" is 0.5 mm, however, the present disclosure is not so-limited and any suitable value for "h" is also contemplated. As illustrated, when epoxy 2430c is disposed on base 2405c of pocket 2400c, first and second step-up transitions 2404c and 2406c can prevent epoxy 2430c from running into first and second adjacent areas 2410c, 2420c. However, the surface tension and surface energy of epoxy 2430c can cause an upward-inflecting meniscus 2432c to form at first and second transitions 2404a, 2406c and at the step-up. Retention of epoxy 2430c within pocket 2400c may be most effective where the height "h" of the step-up exceeds a height of upward-inflecting meniscus 2432c, since the surface tension and surface energy of epoxy 2430c can cause epoxy 2430c to creep along the top portion of meniscus 2432c and into adjacent areas 2410c, 2420c if upward-inflecting meniscus 2432c reaches the level of bases 2415c, 2425c of either of adjacent areas 2410c, 2420c. Accordingly, the step-up height "h," as well as, in some cases the width "w" of transitions 2404c, 2406c, the area or volume of pocket 2400c, may depend not only on the predetermined amount of epoxy 2430c applied, but also on the specific viscosity, surface energy and/or surface tension characteristics between epoxy 2430c, surrounding environment, and the surfaces of the pocket, sensor, dispensing tip, or any other contacting surfaces or fluids. Other factors include the surrounding geometry of the pocket and the surrounding environment (e.g., materials, temperature, or humidity.) This creeping effect of epoxy 2430b when utilized with such "step up" transitions having insufficient height "h" and its limited ability to inhibit or prevent epoxy 2430c from running into adjacent areas may run contrary to conventional wisdom, which could expect that such a "step up" transition would adequately inhibit or prevent epoxy 2430c from running into first and second adjacent areas 2410c, 2420c even if a height of upward-inflecting meniscus 2432c did reach the transition height "h."

As illustrated in FIGS. 22 and 25, transitions between pockets 2400a-c and adjacent areas 2410a-c, 2420a-c may also have varying widths "w" between the transition's sidewalls. An example range of values for "w" is 0.5-2.0 mm, however, the present disclosure is not so-limited and any suitable value for "w" is also contemplated. For example, the first row of pockets 2200a, 2200b, 2200c and 2200d of FIG. 22 are shown as having a relatively narrow transition width "w" of approximately 0.5 mm; the second row of pockets 2200e, 2200f, 2200g and 2200h and 2200p of FIG. 22 are shown as having a relatively moderate transition width "w" of approximately 1.0 mm, greater than the above-described relatively narrow transition width; and the third row of pockets 2200j, 2200k, 2200m and 2200n of FIG. 22 are shown as having a relatively wide transition width "w" of approximately 2.0 mm, greater than either of the above-described relatively narrow or relatively moderate transition widths. FIG. 25 shows transition widths "w" which may correspond to any desired and/or suitable width(s) capable of retaining epoxy in the pocket. Furthermore, transitions on either side of a pocket may have different widths from one another. For example, a first width of a first transition between a pocket and a first adjacent area can be greater than or less than a second width of a second transition between the pocket and a second adjacent area.

As further illustrated in FIG. 25, in some embodiments, adjacent area sidewalls 2422a-c, pocket sidewalls (not shown in FIG. 25) and/or transition sidewalls 2408a-c may be substantially perpendicular to their respective bases 2415a-c, 2425a-c, 2405a-c, as illustrated by the solid vertical lines at the sidewalls. In yet other embodiments, adjacent area sidewalls 2422a-c, pocket sidewalls (not shown in FIG. 25) and/or transition sidewalls 2408a-c may be slightly sloped or angled from such a substantially perpendicular orientations to their respective bases 2415a-c, 2425a-c, 2405a-c, as illustrated by the dashed lines at the sidewalls.

While the embodiments illustrated in FIGS. 22-25 show the same types of transitions on either side of a particular pocket, the present disclosure is not so-limited and any combinations of step-up, step-down and flush transitions may be used on any pocket. For example, a first transition to a first side may be any of a step-up, flush or step-down transition, while the second transition on another side of the pocket may be any of a step-up, flush or step-down transition.

In addition, any number of pockets and or adjacent areas may be utilized in the same wearable assembly 600, on the same housing 622 for such a wearable assembly 600, on the same electronics assembly substrate 630 or even to secure different portions of the same sensor 138. For example, in some embodiments, two or more pockets may be formed in proximity to one another and each may have its own respective adjacent areas or, alternatively, adjacent pockets may share an intervening adjacent area from different sides. Some embodiments further contemplate more or fewer than the two adjacent areas per pocket described.

Figure 26:
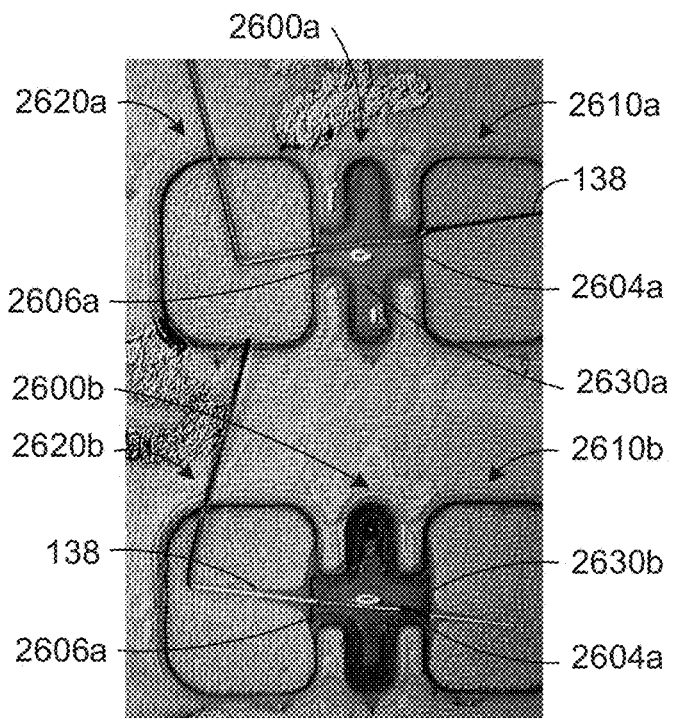
FIG. 26 illustrates a photograph of a top view of example first and second arrangements of epoxied pockets in combination with step-up and step-down transitions to adjacent areas, according to some embodiments.

FIG. 26 illustrates a photograph of a first arrangement comprising a pocket 2600a, a first step-down transition 2604a to a first adjacent area 2610a, and a second step-down transition 2606a to a second adjacent area 2620a. As pictured, epoxy 2630a adhering sensor 138 was substantially contained within pocket 2600a. As previously described in connection with FIG. 24, first and second step-down transitions 2604a, 2606a can inhibit or prevent epoxy 2630a from running into first and second adjacent areas 2610a, 2620a due in part to the surface tension and surface energy of epoxy 2630a causing a downward-inflecting meniscus to form at first and second transitions 2604a, 2606a, which adheres to the edges of first and second transitions 2604a, 2606a. FIG. 26 further illustrates a second arrangement, below the first, comprising a pocket 2600b, a first step-up transition 2604b to a first adjacent area 2610b, and a second step-up transition 2606b to a second adjacent area 2620b. As pictured, epoxy 2630b adhering sensor 138 crept beyond transitions 2604b, 2606b and into adjacent areas 2610b, 2620b.

It is contemplated that the failure of the second arrangement to retain epoxy 2630b within pocket 2600b may have been due to the height of transitions 2604b, 2606b being insufficient such that an upward-inflecting meniscus of epoxy 2630b at step-up transitions 2604b, 2606b reached the bases of first and second adjacent areas 2610b, 2610b, causing epoxy 2630b to creep along the tops of the meniscus and overflow into adjacent areas 2610b, 2620b. Once epoxy 2630b began to run, sensor 138 may have provided a further surface along which epoxy 2630b could overflow.

In some embodiments, flush or step up transitions with insufficient height "h," as previously described in connection with FIGS. 22-26 can be purposefully implemented between one or more pockets and one or more adjacent areas in order to intentionally overflow epoxy onto, for example, certain parts of sensor 138 (e.g., reference electrode 212). In some of those embodiments, a step-down transition may also be utilized between the one or more pockets and other adjacent areas in order to intentionally inhibit or prevent overflow of the epoxy onto, for example, other parts of sensor 138 (e.g., working electrode 211).

Figure 27:
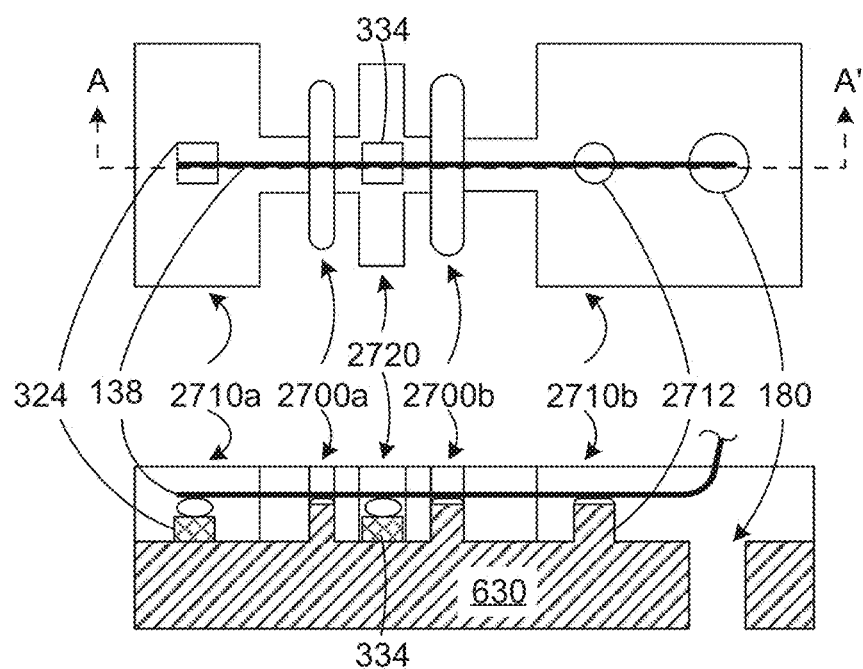
FIG. 27 illustrates a plan view and a side cutaway view of an arrangement utilizing pockets and adjacent areas similar to those described in connection with FIGS. 22-26 for securing a sensor directly to an electronics substrate assembly, further utilizing a post for centering the sensor, according to some embodiments.

FIG. 27 shows a plan view (top) and a side cutaway view (bottom) along cut-line A-A' of an arrangement utilizing pockets 2700a, 2700b and adjacent areas 2710a, 2710b, 2720 similar to that described above in connection with FIGS. 22-26 for securing a sensor 138 directly to electronics substrate assembly 630, and further utilizing an optional post 2712 for centering sensor 138, according to some embodiments. In the figure, a first pocket 2700a and a second pocket 2700b are each illustrated as having step-down transitions on either side to adjacent areas 2710a, 2710b, 2720. Adjacent area 2710a is shown as a first adjacent area for first pocket 2700a, adjacent area 2710b is shown as a first adjacent area for second pocket 2700b, and adjacent area 2720 is shown as a second adjacent area for each of first and second pockets 2700a, 2700b. Contact 324 is shown in adjacent area 2710a, contact 334 is shown in adjacent area 2720, and through-hole 180 is shown in adjacent area 2710b. Adjacent area 2710b is further shown to have post 2712 disposed therein. While specific orientations and placements of the above pockets, adjacent areas, contacts and posts are given, they are to be construed as examples and not limiting of this disclosure, which contemplates any arrangements of all or a subset of the above described features alone or in combination with any other features described in this disclosure or otherwise.

Conductive epoxy or other suitable conductive material is disposed on contacts 324, 334 for electrically coupling respective portions of sensor 138 thereto (e.g., contacts 211*b* and 212*b*, respectively as previously described in connection with at least FIG. 3D).

As further illustrated in FIG. 27, and previously described in connection with FIGS. 22-26, epoxy is disposed within pockets 2700*a*, 2700*b* and is retained therein by virtue of the step-down transitions, e.g., fluidic stops, between pockets 2700*a*, 2700*b* and adjacent areas 2710*a*, 2710*b*, 2720. Similarly, epoxy can be disposed on a top surface of post 2712, which also has step-down features at a transition from its circumferential edges and the base of adjacent area 2710*b* within which post 2712 is disposed that retains the epoxy on the top surface of post 2712. Accordingly, when sensor 138 is placed on the arrangement of FIG. 27, respective portions of sensor 138 can contact and be secured by not only the conductive epoxy disposed on contacts 324, 334, but also by the UV-curable epoxy disposed within pockets 2700*a*, 2700*b* and on post 2712. In addition, due to the substantially symmetrical geometry and relatively smaller top surface of post 2712, the surface energy and surface tension of the epoxy disposed on the top surface of post 2712 will tend to exert a small centering force on the portion of sensor 138 disposed thereon, maintaining or self-correcting alignment of sensor 138.

While post 2712 is shown as having a substantially circular geometry, the present disclosure is not so-limited and post 2712 may have any suitable geometry, though symmetrical geometries as viewed through a centerline defined by the direction of extension of sensor 138 across the top surface of post 2712 may best allow the surface energy and/or surface tension of the epoxy disposed thereon to provide symmetrical forces that center the portion of sensor 138 resting on post 2712.

Figure 40A:
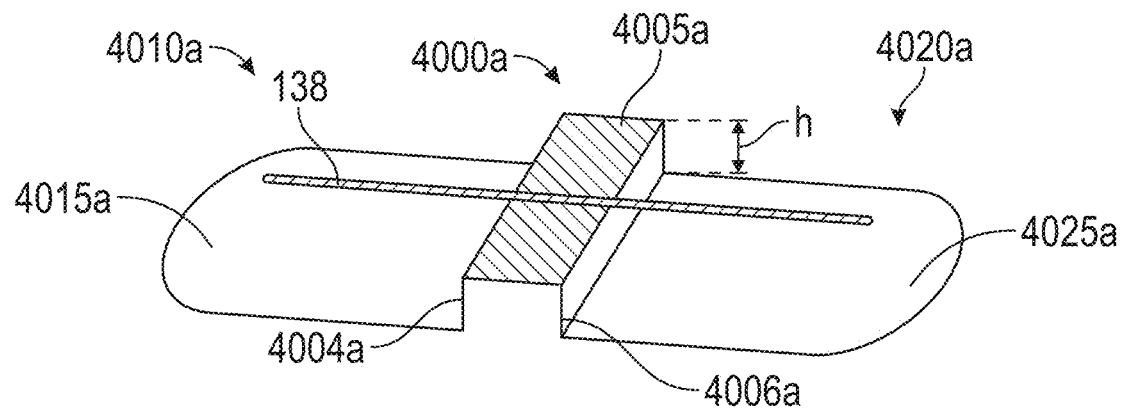
FIG. 40A illustrates a perspective view of a pocket and step-down transitions to adjacent areas having different surface energies than the pocket for preventing the epoxy from bleeding to adjacent areas, according to some embodiments.

In addition, or alternative, to the use of step-up, step-down, and/or flush transitions as previously described in connection with FIGS. 22-27, the present disclosure also contemplates forming bases of the adjacent areas to have different surfaces energies compared to the pocket to thereby prevent the epoxy from bleeding to adjacent areas. FIG. 40A illustrates a perspective view of a pocket 4000*a* with a base 4005*a* having a first surface energy, adjacent areas 4010*a*, 4020*a* with respective bases 4015*a*, 4025*a* having a different surface energy from the first surface energy of pocket base 4005*a*. In some embodiments, bases 4015*a*, 4025*a* can have a same, second surface energy that is different from the first surface energy of pocket base 4005*a*. In some other embodiments, base 4015*a* can have the second surface energy, while base 4025*a* can have a third surface energy different from the first and second surface energies. In some embodiments, the first, second and/or third surface energies of pocket base 4005*a* and adjacent area bases 4015*a*, 4025*a* can be determined, set and/or modified by applying one or more of, e.g., a plasma etch, a Teflon tape, a relatively low-surface energy tape, a different surface texture, grooves or any other suitable materials or features to one or more of pocket base 4005*a* and adjacent area bases 4015*a*, 4025*a*. FIG. 40A further illustrates step-down transitions 4004*a* and 4006*a* to respective adjacent areas 4010*a*, 4020*a*.

Figure 40B:
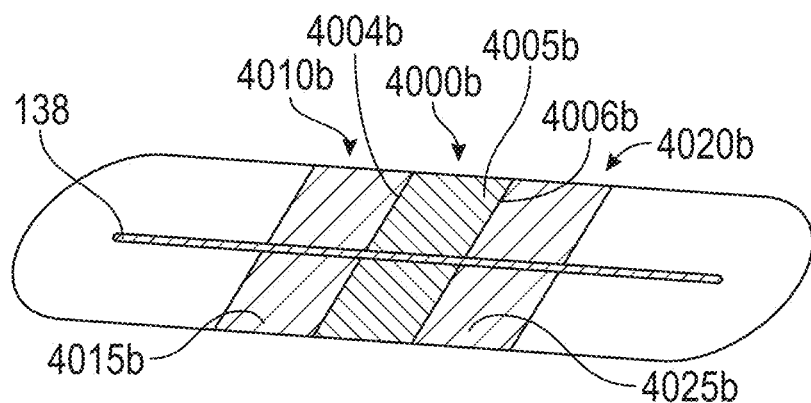
FIG. 40B illustrates a perspective view of a pocket and flush transitions to adjacent areas having different surface energies than the pocket for preventing the epoxy from bleeding to adjacent areas, according to some embodiments.

FIG. 40B illustrates a pocket 4000*b* with a base 4005*b* having a first surface energy, adjacent areas 4010*a*, 4020*b* with respective bases 4015*a*, 4025*b* having a different surface energy from the first surface energy of pocket base 4005*b*. In some embodiments, bases 4015*a*, 4025*b* can have a same, second surface energy that is different from the first surface energy of pocket base 4005*b*. In some other embodiments, base 4015*b* can have the second surface energy, while base 4025*b* can have a third surface energy different from the first and second surface energies. In some embodiments, the first, second and/or third surface energies of pocket base 4005*b* and adjacent area bases 4015*a*, 4025*b* can be determined, set and/or modified by applying one or more of, e.g., a plasma etch, a Teflon tape, a relatively low-surface energy tape, a different surface texture, grooves or any other suitable materials or features to one or more of pocket base 4005*b* and adjacent area bases 4015*a*, 4025*b*. In contrast to FIG. 40A, FIG. 40B further illustrates flush transitions 4004*b* and 4006*b* to respective adjacent areas 4010*a*, 4020*b*.

The differing surface energies at the transitions 4004*a-b*, 4006*a-b* can cause epoxy disposed within pockets 4000*a-b* to form a down-ward inflecting meniscus at transitions 4004*a-b*, 4006*a-b*, respectively, similar to that previously described in connection with at least FIGS. 24 and 25, thereby preventing the epoxy from undesirably creeping from pocket base 4005*a-b* to adjacent areas 4010*a-b*, 4020*a-b*.

Figure 41:
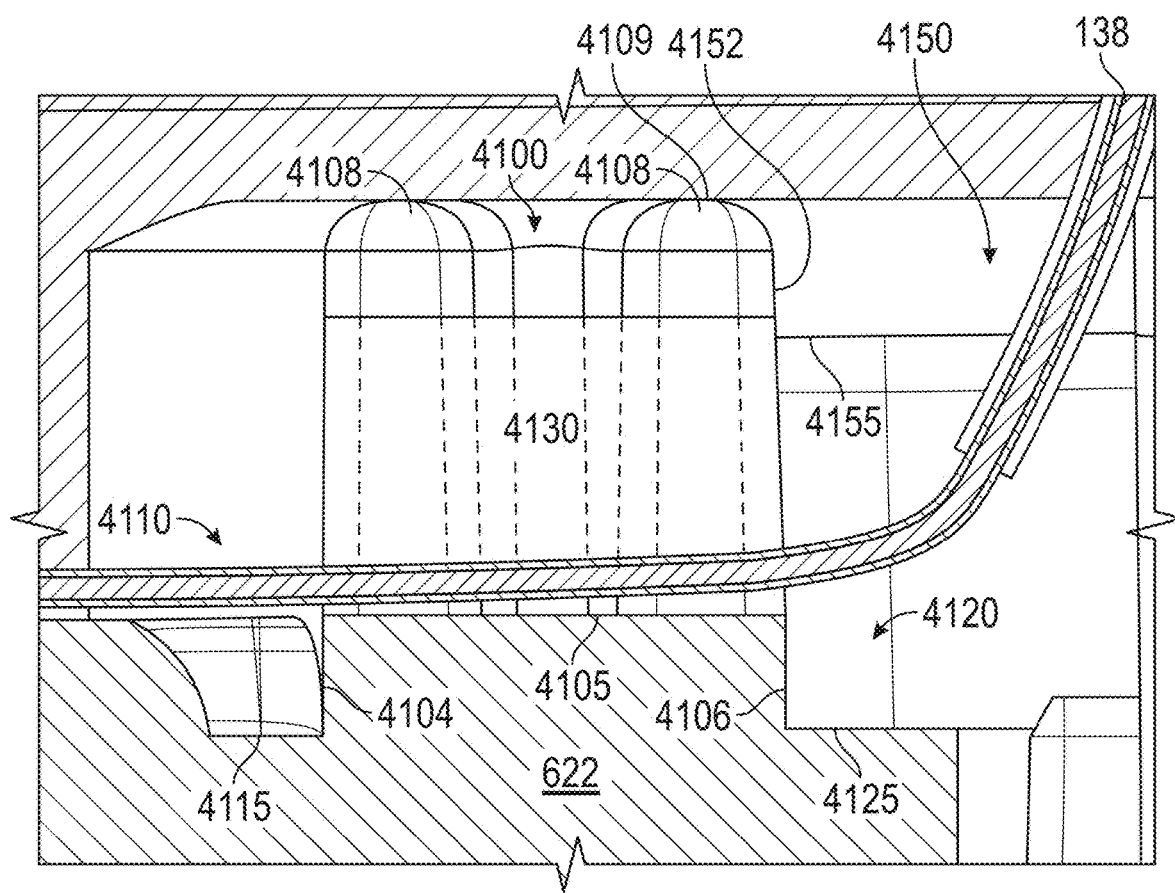
FIG. 41 illustrates a side cutaway view of a pocket having step-down transitions to adjacent areas, and further including an additional step-down transition to an additional adjacent area for preventing the epoxy from bleeding to adjacent areas, according to some embodiments.

FIG. 41 illustrates a side cutaway view of a pocket 4100 having step-down transitions 4104, 4106 to respective adjacent areas 4110, 4120, and further including an additional step-down transition 4152 to an additional adjacent area 4150 for preventing epoxy from bleeding to adjacent areas 4110, 4120, according to some embodiments.

In some embodiments, in addition to, or in the alternative of, utilizing one or more adjacent areas as previously described in connection with at least FIGS. 22-27, one or more adjacent areas 4150 may be disposed immediately adjacent to and/or abutting a sidewall 4108 of a pocket 4100 and configured to accept at least an excess portion of epoxy 4130 disposed within pocket 4100, thereby preventing epoxy 4130 from creeping into at least one of adjacent areas 4110, 4120.

For example, FIG. 41 shows pocket 4100 having base 4105 and sidewalls 4108 having a top surface 4109, an adjacent area 4110 having a base 4115, a transition 4104 between base 4115 and base 4105, an adjacent area 4120 having a base 4125, and a transition 4106 between base 4125 and base 4105. Transitions 4104, 4106 are shown as "step down" transitions as previously described in connection with FIGS. 22-27. However, the present disclosure is not so limited and one or both of transitions 4104, 4106 can alternatively be "flush" or "step up" transitions as previously described.

While transitions 4104, 4106 may be configured to prevent an epoxy 4130, disposed within pocket 4100 on base 4105, from wicking and/or creeping into adjacent areas 4110, 4120, if pocket 4100 is sufficiently overfilled with epoxy 4130, the adhering character of one or both of transitions 4104, 4106 with respect to epoxy 4130, in isolation, may be insufficient to prevent epoxy 4130 from wicking and/or creeping into adjacent areas 4110, 4120. Accordingly, by providing adjacent area 4150 with a base 4155 disposed at a lower elevation than top surface 4109 of sidewall 4108 of pocket 4100 and a transition 4152 between top surface 4109 of sidewall 4108 of pocket 4100 and base 4155, adjacent area 4150 can be configured to accept at least an excess portion of epoxy 4130 disposed within pocket 4100, thereby preventing epoxy 4130 from creeping into at least one of adjacent areas 4110, 4120. In such embodiments, step down transition 4152 may be specifically configured to allow excess portions of epoxy 4130 to flow, creep and/or wick into adjacent area 4150 and not into adjacent areas 4110, 4120. In some embodiments, transition 4152 may alternatively be configured to cause epoxy 4130 disposed within pocket 4100 to adhere to transition 4152 and thereby inhibit epoxy 4130 from creeping into adjacent area 4150.

In any of the above embodiments featuring a pocket and an adjacent area, an additional conductive adhesive material, such as a conductive epoxy, may be implemented to mechanically and electrically connect sensor 138 to contacts of electronics assembly substrate 630. For example, sensor 138 may be affixed to a pocket as described above, and affixed and electrically connected to electronics assembly substrate 630 as described in FIGS. 21A-21D. In some embodiments, sensor 138 is first affixed to a pocket and then affixed to the electronics assembly substrate. In other embodiments, sensor 138 is first affixed to the electronics assembly substrate and then affixed to a pocket.

Utilization of a Passivation Layer on a Connected Sensor in a Pocket of a Wearable Transmitter Wearable analyte sensor transmitter assemblies 500, 600 as previously described may be vulnerable to leakage currents in the circuitry disposed therein as a consequence of undesirable moisture ingress. Such leakage currents may be detected during long-term heat and humidity testing of the analog front end (AFE) of such transmitters. Accordingly, it may be desirable to prevent moisture from interfering with the signal received by the AFE. An example solution is described in connection with FIGS. 28A-28C below.

Figure 28A:
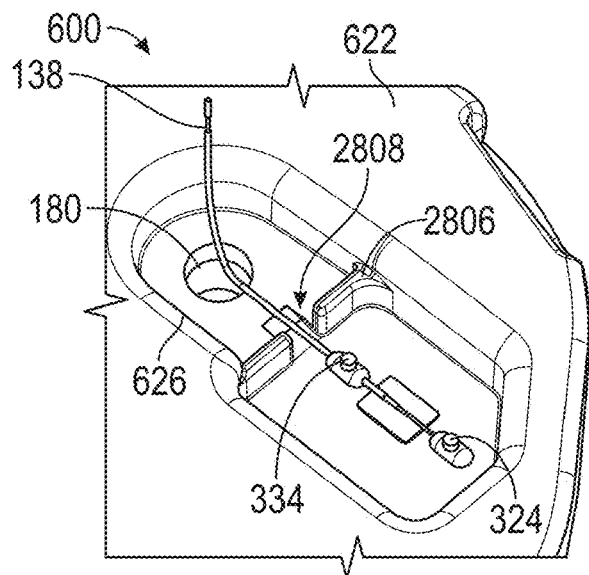
FIG. 28A illustrates a perspective view of a wearable assembly having a sensor directly connected to an electronics assembly substrate, according to some embodiments.

FIG. 28A shows a perspective view of wearable assembly 600 comprising lower housing 622 having aperture 626, sensor 138 having at least a portion disposed within aperture 626 and being directly connected to electronics assembly substrate 630 (not shown in FIGS. 28A-28C) by one or more conductive contacts (e.g., conductive contacts 324, 334), as previously described in FIGS. 6A-6C, for example. FIG. 28A further illustrates a dam 2806 separating a first portion of a cavity, formed by aperture 626 and having at least a proximal portion of sensor 138 disposed therein, from a second portion of the cavity having through-hole 180 and a medial and/or distal portion of sensor 138. Dam 2806 is shown to have a narrow gap 2808 through which sensor 138 is configured to pass.

Figure 28B:
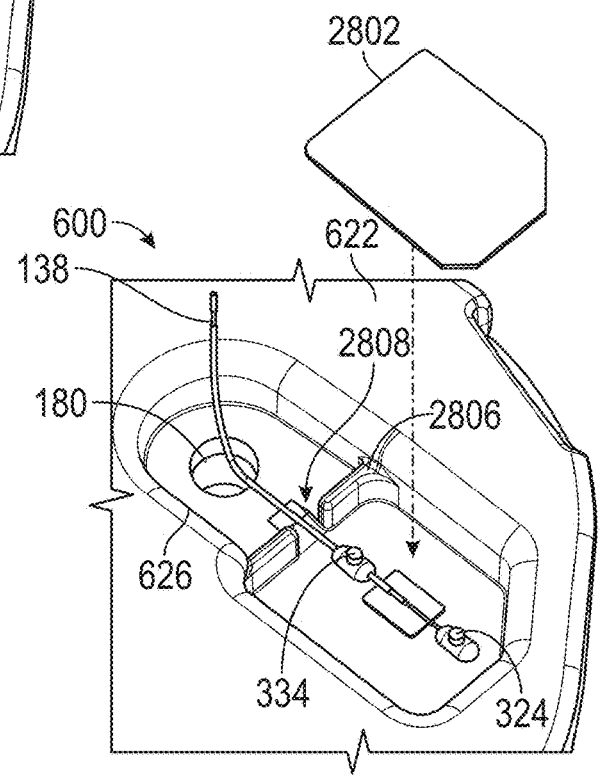
FIG. 28B illustrates an exploded perspective view of the wearable assembly of FIG. 28A further including a passivation layer deposited over at least a portion of the electronics assembly substrate and the sensor.

As shown by FIG. 28B, an electrical and moisture passivation layer 2802 can be applied to the top surface of at least the proximal portion of sensor 138 and at least a portion of housing 622 disposed within the first portion of the cavity utilizing any suitable method, for example, vacuum deposition, inkjet printing, 3D printing, sputtering, chemical vapor deposition or any other suitable deposition technique.

Figure 28C:
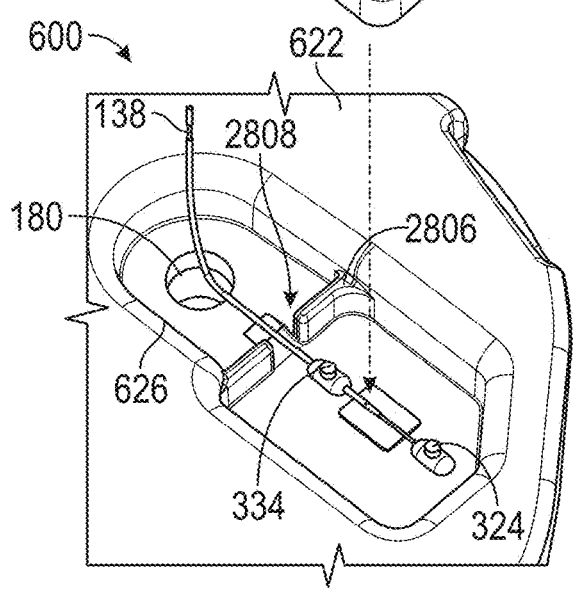
FIG. 28C illustrates an exploded perspective view of the wearable assembly of FIG. 28B further including an encapsulating sealant disposed over the passivation layer.

Once passivation layer 2802 has been applied, the first portion of the cavity formed by aperture 626 and containing at least the proximal portion of sensor 138 can be filled with an epoxy or other suitable material for mechanical fixation and protection of at least the proximal portion of sensor 138. In addition, or in the alternative, to filling the first portion of the cavity with epoxy, a cap may be placed over aperture 626, for example, as previously described in connection with FIGS. 7A-10. While FIGS. 28A-28C illustrate dam 2806 being a part of lower housing 622, the present disclosure is not so-limited and such a dam may be made a part of a cap that is disposed within, on or over aperture 626, also as previously described in connection with at least FIGS. 7A-10.

Figure 29:
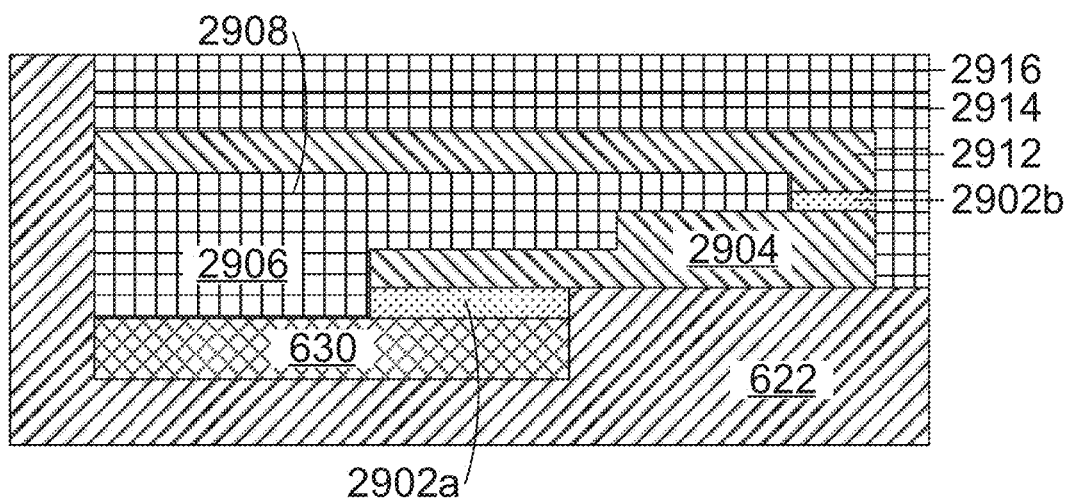
FIG. 29 illustrates a side cutaway view of a wearable assembly comprising an electronics assembly substrate having a plurality of passivation layers and conductive trace layers serially deposited thereon, according to some embodiments.

Another passivation technique that may be utilized to prevent or substantially reduce moisture ingress to circuitry of wearable 500, 600 is shown in FIG. 29. As shown in the figure, lower housing 622 may have a molded geometry configured to receive electronics assembly substrate 630. Rather than directly connecting one or more electrical connections to electronics assembly substrate 630, a plurality of contacts, conductive trace layers, and passivation layers may be serially deposited such that those electrical connections can be made at a level above that of electronics assembly substrate 630 while still sealing and protecting the underlying electronics assembly substrate 630 and/or sensor 138 from moisture ingress.

For example, one or more electrical contacts, conductive pucks or other conductive structures 2902a can be deposited at the appropriate locations on electronics assembly substrate 630. One or more conductive trace layers 2904 can be deposited on contact(s) 2902a and on a portion of lower housing 622. In some embodiments, conductive trace layer(s) 2904 extend to a greater extent laterally than either or both of contact(s) 2902a and electronics assembly substrate 630. A plurality of passivation layers 2906, 2908 can then be deposited over at least a remaining exposed portion of electronics assembly substrate 630 and portions of conductive trace layer(s) 2904, thereby sealing and passivating electronics assembly substrate 630 and/or sensor 138 from moisture ingress from the outside environment. In some embodiments, passivation layers 2906, 2908 may comprise different passivating materials from one another, for example, a conformal coating, a UV-curable glue, a sputtered metal (e.g., aluminum), a thin metal coating, a polymer (e.g., polyethylene), an elastomer, a ceramic or any other suitable material. One or more electrical contacts, conductive pucks or other conductive structures 2902b can be deposited at the appropriate exposed locations on conductive trace layer(s) 2904 and one or more additional conductive trace layers 2912 can be deposited over contact(s) 2902b and passivation layer(s) 2906, 2908. In some embodiments, conductive trace layer(s) 2912 extend laterally from contact(s) 2902b such that one or more electrical connections can be made at a location on conductive trace layer(s) 2912 laterally removed from contact(s) 2902b. One or more additional passivation layers 2914, 2916 can then be deposited over the underlying layers to seal and protect not only the underlying passivation and conductive layers, but also electronics assembly substrate 630 from mechanical- and moisture-related damage.

Sealing a Housing Cavity Without UV Epoxy Fill and Encapsulation

In some embodiments it may be desirable to be able to seal a cavity of housing 622 and the electronic circuitry disposed therein form moisture ingress without having to fill the cavity with a curable epoxy. Accordingly, several solutions are described below in connection with FIGS. 30A-33.

Figure 30B:
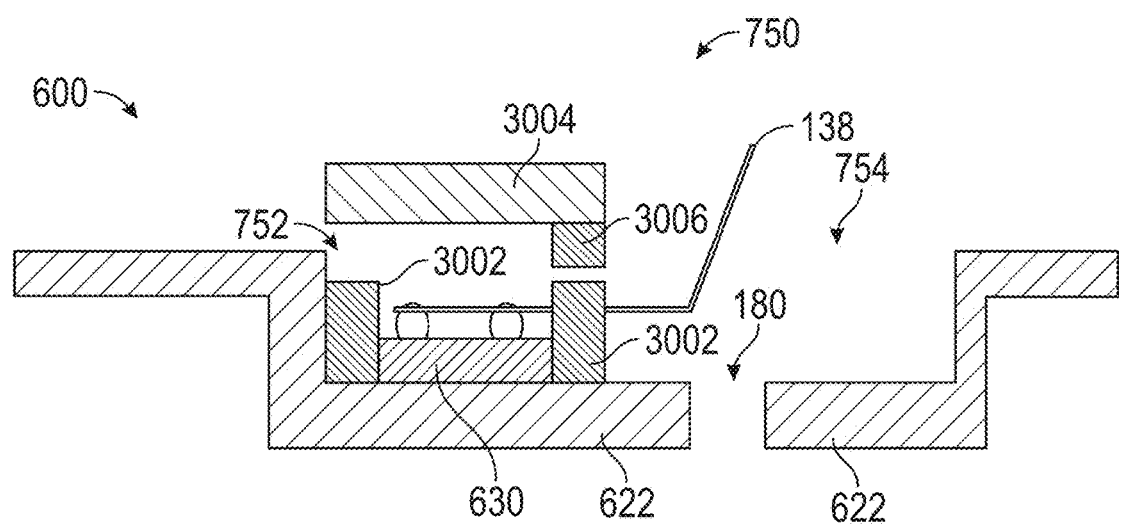
FIG. 30B illustrates a side cutaway view of the wearable assembly of FIG. 30A, as viewed along the cutline A-A' and the mating cap disposed for securing to wearable assembly, according to some embodiments.

FIG. 30A illustrates a plan view of a wearable assembly 600 including a heat-sealable thermoplastic elastomer 3002 and a mating cap 3004 including a heat-sealable thermoplastic elastomer 3006, according to some embodiments. FIG. 30B illustrates a side cutaway view of wearable assembly 600, as viewed along the cutline A-A' in FIG. 30A, and mating cap 3004 disposed for securing to wearable assembly 600.

Wearable assembly 600 comprises lower housing 622, including aperture 626 that forms a cavity within lower housing 622. A first portion of this cavity is configured to house at least a proximal portion of sensor 138, while a second portion of this cavity comprises through-hole 180 through which a sensor applicator needle is configured to pass. Heat-sealable thermoplastic elastomer 3002 is disposed partially or completely around the first portion of the cavity formed by aperture 626. As shown in FIG. 30B, heat-sealable thermoplastic elastomer 3002 surrounds at least the proximal portion of sensor 138 as placed in the first portion of the cavity. Sensor 138 is further shown as being electrically connected to electronics assembly substrate 630 and passing through a slit (not shown) in heat-sealable thermoplastic elastomer 3002, thereby extending into the second portion of the cavity having through-hole 180. While FIG. 30B illustrates electronics sensor assembly 630 as being within a same cavity as the proximal portion of sensor 138, the present disclosure is not so limited. Electronics sensor assembly 630 can alternatively be disposed within a different cavity within housing 622 than the proximal portion of sensor 138 and may be separated from sensor 138 by at least a portion of housing 622, through which one or more conductive contacts (e.g., contacts 324, 334 of FIG. 3D) can provide direct electrical connection between sensor 138 and electronics assembly substrate 630 (see, e.g., FIGS. 6A-6C).

As further shown in FIG. 30B, the heat-sealable thermoplastic elastomer 3006 disposed on cap 3004 is configured to abut a portion of heat-sealable thermoplastic elastomer 3002 adjacent to or abutting the second portion of the cavity through which sensor 138 is configured to pass when cap 3004 is properly placed. Upon proper placement of cap 3004 on lower housing 622 of wearable assembly 600, heat may be applied to heat-sealable thermoplastic elastomers 3002, 3006, for example by laser, to melt heat-sealable thermoplastic elastomers 3002, 3006 against respective portions of cap 3004 and lower housing 622, thereby welding and sealing at least the first portion of the cavity formed by aperture 626 that houses at least the proximal portion of sensor 138 from moisture ingress. Among other advantages, because the seal provided by melting heat-sealable thermoplastic elastomers 3002, 3006 is moisture-tight, curable epoxy encapsulation within the cavity (as previously described in connection with at least FIGS. 6A-10) is not necessary and can be eliminated, reducing manufacturing complexity.

Figure 31:
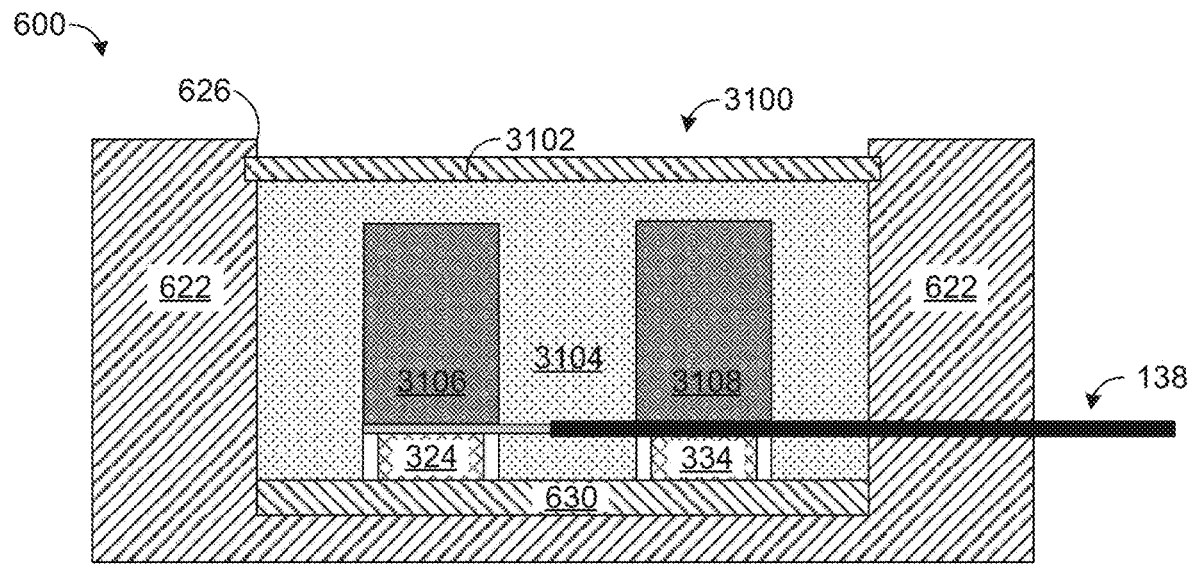
FIG. 31 illustrates a side cutaway view of a wearable assembly and an overmolded cap, according to some embodiments.

Another solution will now be described in connection with FIG. 31 below. FIG. 31 illustrates a side cutaway view of a portion of lower housing 622 of wearable assembly 600 and an overmolded cap 3100, according to some embodiments. As shown, electronic assembly substrate 630 is configured to rest within the geometry of lower housing 622. Contacts 324, 334 are disposed on electronic assembly substrate 630. Sensor 138 is disposed over contacts 324, 334 such that respective portions of the sensor make physical and electrical contact with contacts 324, 334 (e.g., respective contacts 211b and 212b, as previously described in connection with at least FIG. 3D). While electronics assembly substrate 630 is shown as disposed within a same cavity as at least a proximal portion of sensor 138, the present disclosure is not so limited and at least a portion of housing 622 can physically separate electronics assembly substrate 630 from the cavity within which the proximal portion of sensor 138 is disposed (see, e.g., FIGS. 6A-6C). In such embodiments, contacts 324, 334 can extend through the portion of housing 622 that physically separates electronics assembly substrate 630 to make electrical contact with sensor 138.

FIG. 31 further shows a cap or an overmolded cap 3100 comprising a base material 3102, for example polycarbonate, plastic, metal, or any other material with suitable strength to maintain a seal. The overmolded cap 3100 further comprises an insulating and sealing material 3104 having a plurality of cavities in which conductive elastomeric pucks 3106 and 3108 reside in or fit into. In some embodiments, the cavities and the conductive elastomeric pucks 3106, 3108 may have a substantially cylindrical shape. However, the present disclosure is not so-limited and any shape is also contemplated. In some embodiments, a portion of insulating and sealing material 3104 is disposed directly between facing surfaces of base material 3102 and conductive elastomeric pucks 3106 and 3108. When overmolded cap 3100 is placed over and/or within the cavity of housing 622, conductive elastomeric pucks 3106 and 3108 press against portions of sensor 138 and contacts 324, 334, thereby securing the portions of sensor 138 to their respective contacts 324, 334. Although not shown, it is contemplated that, in some embodiments, conductive elastomeric pucks 3106 and 3108 may be disposed adjacent to contacts 324 and 334, respectively, and sensor 138 may be disposed adjacent to conductive elastomeric pucks 3106 and 3108 on the side opposite contacts 324 and 334. In such embodiments, conductive elastomeric puck 3106 may press against a first electrode of sensor 138 on one side and press against cap 3100 on the other. Conductive elastomeric puck 3108 may press against a second electrode of sensor 138 on one side and press against cap 3100 on the other. Further, in other embodiments, conductive elastomeric pucks 3106 and 3108 may each be composed of two halves, in which portions of sensor 138 may reside between the two halves of puck 3106 or 3108 or both pair of halves of pucks 3106 and 3108. Further, in other embodiments, it is contemplated that one or more of contacts 324 and 334 may have a gap formed within the contact. In such embodiments, at least one of conductive elastomeric pucks 3106 and 3108 may reside within (e.g. via press fit or friction fit) the gap of either contact 324 or 334.

As shown in FIG. 31, insulating and sealing material 3104 is configured to fill or at least partially fill the cavity contacts 324, 334 and the contacting portions of sensor wire 138, sealing them from moisture ingress. Among other advantages, embodiments according to FIG. 31 can remove curable epoxy dispensing and curing steps, conductive epoxy dispensing and curing steps and, potentially, extra strain-relief steps related to sensor 138, thereby reducing manufacturing complexity.

Figure 32:
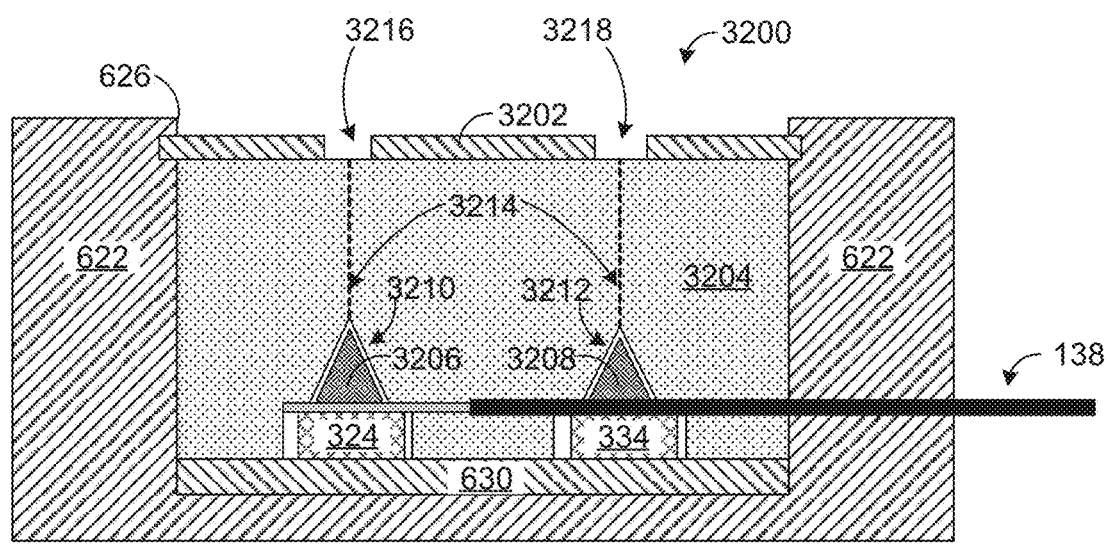
FIG. 32 illustrates a side cutaway view of a wearable assembly and another overmolded cap, according to some embodiments.

Yet another solution will now be described in connection with FIG. 32 below. FIG. 32 illustrates a side cutaway view of a portion of lower housing 622 of wearable assembly 600 and an overmolded cap 3200, according to some embodiments. As shown, electronic assembly substrate 630 is configured to rest within the geometry of lower housing 622. Contacts 324, 334 are disposed on electronic assembly substrate 630. Sensor 138 is disposed over contacts 324, 334 such that respective portions of the sensor make physical and electrical contact with contacts 324, 334 (e.g., respective contacts 211b and 212b, as previously described in connection with at least FIG. 3D). While electronics assembly substrate 630 is shown as disposed within a same cavity as at least a proximal portion of sensor 138, the present disclosure is not so limited and at least a portion of housing 622 can physically separate electronics assembly substrate 630 from the cavity within which the proximal portion of sensor 138 is disposed (see, e.g., FIGS. 6A-6C). In such embodiments, contacts 324, 334 can extend through the portion of housing 622 that physically separates electronics assembly substrate 630 to make electrical contact with sensor 138.

FIG. 32 further shows an overmolded cap 3200 comprising a base material 3202, for example polycarbonate, plastic, metal, or any other material with suitable strength to maintain a seal. Base material 3202 is shown as having a plurality of apertures or holes 3216, 3218 at locations configured to be over and laterally aligned with contacts 324, 334 when overmolded cap 3200 is properly placed. Overmolded cap 3200 further comprises an insulating and sealing material 3204 having a plurality of cavities 3210, 3212 configured to be disposed directly over contacts 324, 334 when overmolded cap 3200 is properly placed. Cavities 3210, 3212 are configured to receive respective injections of conductive epoxy 3206, 3208 via injection needle through holes 3216, 3218 and through insulating and sealing material 3204 along the lines of needle pierce lines 3214 after overmolded cap 3200 is properly placed. Accordingly, holes 3216, 3218 are also aligned laterally with first and second cavities 3206, 3208. Moreover, as shown in the figure, at least a portion of sealing material 3204 physically isolates first hole 3216 from first cavity 3210 and second hole 3218 from second cavity 3212. In some embodiments, cavities 3210, 3212 and conductive epoxy injections 3206, 3208 may have substantially conical shapes. However, the present disclosure is not so-limited and any shape is also contemplated.

When overmolded cap 3200 is placed over electronic assembly substrate 630, cavities 3210, 3212 align directly over contacts 324, 334. Insulating and sealing material 3204 presses against portions of sensor 138 and contacts 324, 334, thereby holding the portions of sensor 138 to their respective contacts 324, 334, substantially sealing cavities 3210, 3212. Accordingly, when a needle is pressed through insulating and sealing material 3204 at apertures 3216, 3218 along needle pierce lines 3214 until the tip of the needle breaks through into cavities 3206, 3208, and conductive epoxy 3206 and 3208 is subsequently injected into cavities 3206, 3208, conductive epoxy 3206 and 3208 is contained within cavities 3206, 3208 eliminating the potential for undesirable shorting if conductive epoxy 3206 and 3208 were otherwise allowed to overflow laterally substantially beyond contacts 324, 334. In addition, in some embodiments a conductive epoxy that does not require heating to cure can be utilized to reduce heat exposure and related damage to sensor 138. Insulating and sealing material 3204 further seals contacts 324, 334 and the contacting portions of sensor 138 from moisture ingress.

Among other advantages, embodiments according to FIG. 32 can remove curable epoxy dispensing and curing steps and, potentially, extra strain-relief steps related to sensor 138, thereby reducing manufacturing complexity.

Methods of Manufacture Related to the Above-Described Embodiments

Several example methods of fabricating an analyte sensing apparatus and/or housing having an analyte sensor directly connected to a printed circuit board of a wearable transmitter assembly without the utilization of a sensor carrier are provided below in connection with FIGS. 33-37.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Figure 33:
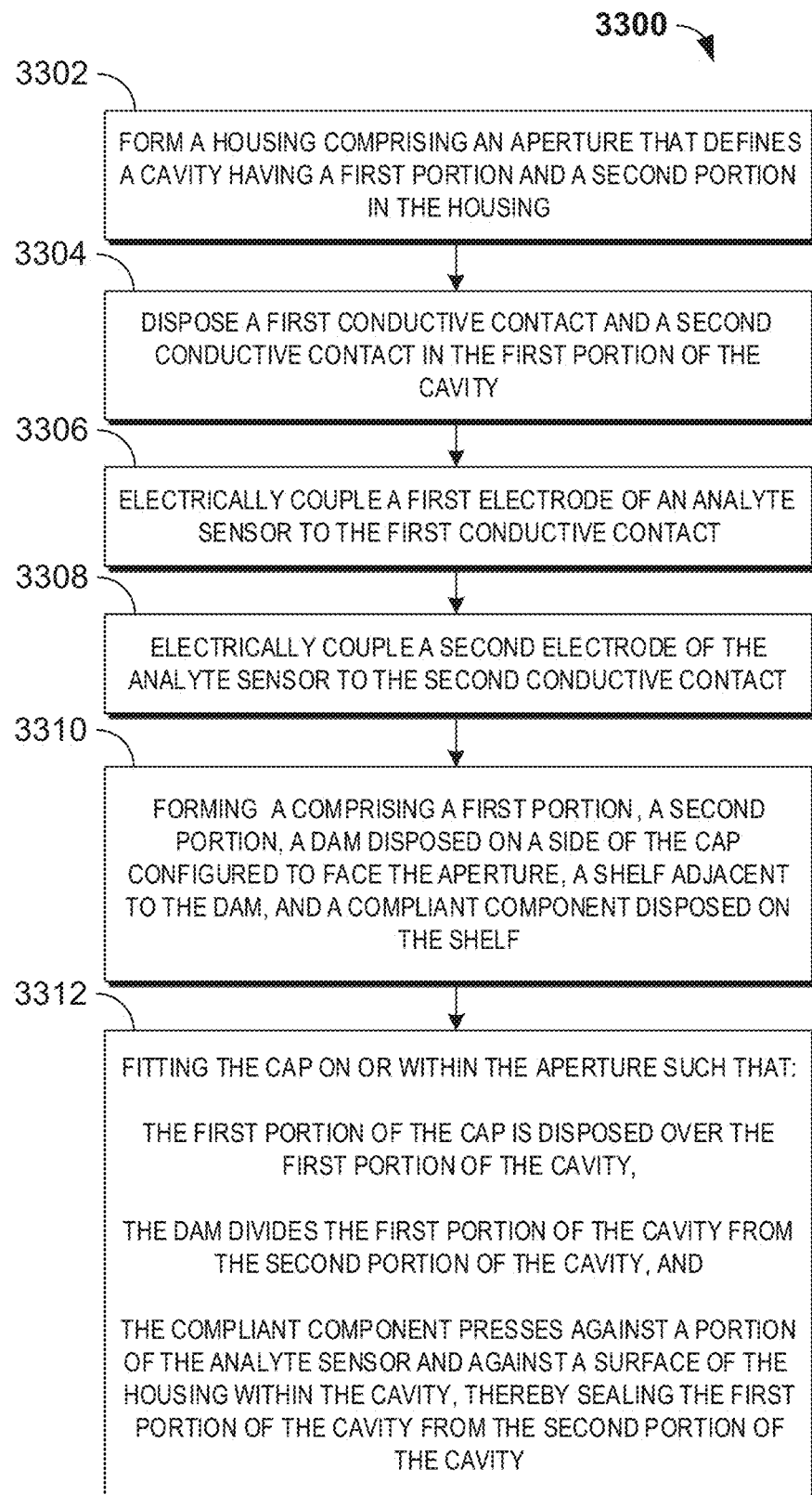
FIG. 33 illustrates a flow chart of illustrative operations that may be performed for manufacturing and using an analyte sensor directly connected to a circuit board of a transmitter, according to some embodiments.

An example method 3300 for fabricating an analyte sensing apparatus will now be described in connection with FIG. 33 below. Method 3300 may correspond at least to the previous description in connection with FIGS. 7A-10 and 28A-29.

Block 3302 includes forming a housing comprising an aperture that defines a cavity having a first portion and a second portion in the housing. For example, as previously described in connection with FIGS. 6A-10, lower housing 622 can be formed comprising aperture 626 that defines cavity 750 having first portion 752 and second portion 754 in lower housing 622.

Block 3304 includes disposing a first conductive contact and a second conductive contact in the first portion of the cavity. For example, first conductive contact 324 and second conductive contact 334 can be disposed in first portion 752 of cavity 752.

Block 3306 includes electrically coupling a first electrode of an analyte sensor to the first conductive contact. For example, first electrode 211b of analyte sensor 138 can be directly electrically coupled to first conductive contact 324.

Block 3308 includes electrically coupling a second electrode of the analyte sensor to the second conductive contact. For example, second electrode 212b of analyte sensor 138 can be directly electrically coupled to second conductive contact 334.

Block 3310 includes forming a cap comprising a first portion and a second portion, a dam disposed on a side of the cap configured to face the aperture, a shelf adjacent to the dam, and a compliant component disposed on the shelf. For example, as previously described in connection with FIGS. 7A-7C and 9, cap 700, 900 can be formed to include first portion 710, 910 and second portion 720, 920, dam 730, 930 disposed on a side of cap 700, 900 configured to face aperture 626, shelf 732 adjacent to dam 730, and compliant component 740, 940 disposed on shelf 732.

As previously described in connection with FIGS. 7A-7C, first portion 710 of cap 700 and second portion 720 of cap 700 can be coplanar and formed of a single piece. As previously described in connection with FIG. 9, first portion 910 of cap 900 can extend along a first plane, second portion 920 of cap 900 can extend along a second plane different from the first plane, dam 930 can comprise at least a portion of cap 900 that extends between the first plane and the second plane and connects first portion 910 of cap 900 with second portion 920 of cap 900, and at least some of second portion 920 of cap 900 can comprise the shelf on which compliant component 940 rests.

Block 3312 includes fitting the cap on or within the aperture such that the first portion of the cap is disposed over the first portion of the cavity, the dam physically divides the first portion of the cavity from the second portion of the cavity, and the compliant component presses against a portion of the analyte sensor and against a surface of the housing within the cavity, thereby sealing the first portion of the cavity from the second portion of the cavity. For example, cap 700, 900 can be fit on or within aperture 626 such that first portion 710, 910 of cap 700, 900 is disposed over first portion 752 of cavity 750, dam 730, 930 physically divides first portion 752 of cavity 750 from second portion 754 of cavity 750, and compliant component 740, 940 presses against a portion of analyte sensor 138 and against a surface of lower housing 622 within cavity 750, thereby sealing first portion 752 of cavity 750 from second portion 754 of cavity 750.

In some embodiments, method 3300 may further comprise disposing electronics assembly substrate 630 within housing 622, wherein first conductive contact 324 and second conductive contact 334 extend from electronics assembly substrate into first portion 752 of cavity 750.

In some embodiments, first portion 710, 910 of cap 700, 900 can comprise first hole 702, 902 and method 3300 can further comprise, for example, depositing encapsulating sealant 628, 928 into first portion 752 of cavity 750 through first hole 702, 902, thereby sealing at least a portion of analyte sensor 138 from moisture ingress.

In some embodiments, first portion 710, 910 of cap 700, 900 can comprise second hole 704, 904, and method 3300 can further comprise, for example, allowing excesses of encapsulating sealant 628, 928 to flow out of first portion 752 of cavity 750 through second hole 704, 904.

In some embodiments, dam 730, 930 can contact a portion of lower housing 622 within cavity 750. In some embodiments, compliant component 740, 940 can comprise a foam or a rubber material. In some embodiments, compliant component 740, 940 can prevent encapsulating sealant 628, 928 from flowing into second portion 754 of cavity 750.

In some embodiments, cap 700 can comprise second portion 720, 920 disposed over second portion 754 of cavity 750. In some other embodiments, cap 900 can comprise second portion 920 disposed adjacent to second portion 754 of cavity 750. In some embodiments, second portion 710 of cap 700 can comprise slot 722, and method 3300 can further comprise, for example, causing at least a portion of analyte sensor 138 to pass through slot 722.

In some embodiments, an outside-facing surface of cap 700, 900 can fit flush with an outside-facing surface of lower housing 622. In some other embodiments, the outside-facing surface of cap 700, 900 can fit in a recessed position compared to the outside-facing surface of lower housing 622. In yet other embodiments, cap 700, 900 can be disposed on the outside-facing surface of lower housing 622.

In some embodiments, method 3300 can further comprise, for example, securing cap 700, 900 to lower housing 622 utilizing at least one of a toe feature, a snap feature, a friction-fit feature, and a pressure-sensitive adhesive.

In some embodiments, cap 700, 900 comprises a material substantially transparent to ultra-violet radiation, and method 3300 can further comprise, for example, curing encapsulating sealant 628, 928 by exposing encapsulating sealant 628, 928 to the ultra-violet radiation through cap 700, 900.

In some embodiments, method 3300 can further involve the fabrication and/or application of an adhesive patch as previously described in connection with FIGS. 8A-8C. Method 3300 can further comprise, for example, securing cap 700, 900 to lower housing 622 utilizing first adhesive portion 902 of adhesive patch 126, adhesive patch 126 further comprising second adhesive portion 804 configured to adhere first adhesive portion 802 and wearable assembly 600 to a skin of a host. Method 3300 can further comprise, for example, securing first adhesive portion 802 of adhesive patch 126 to cap 700, 900 before cap 700, 900 is fit on or within aperture 626 of lower housing 622. First adhesive portion 802 can comprise at least a hole 880a configured to substantially coincide with at least one hole within cap 700, 900 when cap 700, 900 is secured to first adhesive portion 802 of adhesive patch 126. Second adhesive portion 804 can comprise at least a hole 880b configured to substantially coincide with at least one hole within cap 700, 900 when cap 700, 900 is secured to second adhesive portion 804 of adhesive patch 126.

In some embodiments, as described in connection with FIGS. 28A-29, method 3300 can further comprise, for example, depositing at least one passivation layer 2802, 2906, 2908 over at least a portion of analyte sensor 138, thereby preventing moisture ingress to the portion of sensor 138. Method 3300 can further comprise depositing one or more conductive traces 2904, 2912 on the passivation layer (s) 2906, 2908, and electrically coupling conductive traces 2904, 2912 to one or more of first conductive contact 324 and second conductive contact 334, e.g., one or both potentially illustrated as contact 2902a in FIG. 29.

Figure 34:
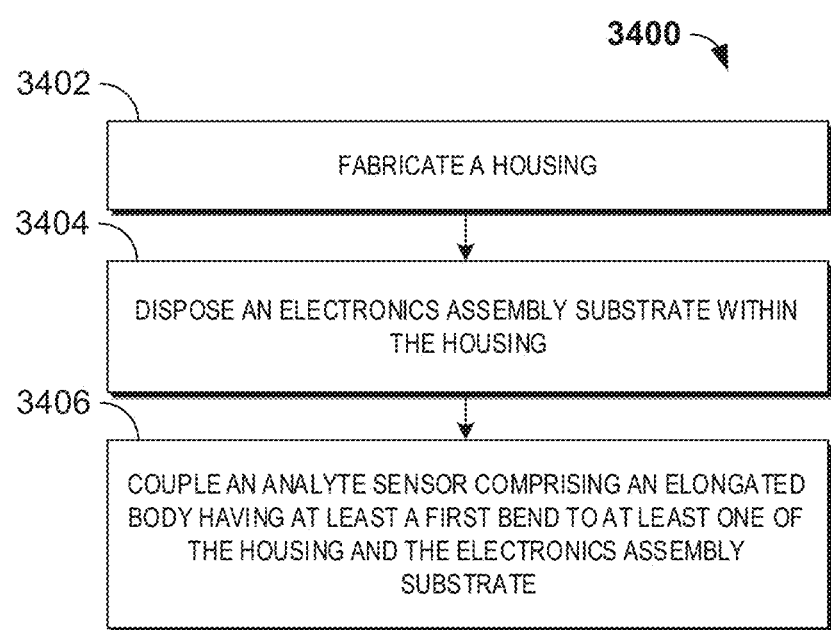
FIG. 34 illustrates another flow chart of illustrative operations that may be performed for manufacturing and using an analyte sensor directly connected to a circuit board of a transmitter, according to some embodiments.

An example method 3400 for fabricating an analyte sensing apparatus will now be described in connection with FIG. 34 below. Method 3400 may correspond at least to the previous description in connection with FIGS. 11A-20.

Block 3402 includes fabricating a housing. For example, lower housing 622 can be formed as previously described in connection with FIGS. 11A-20.

Block 3404 includes disposing an electronics assembly substrate within the housing. For example, electronics assembly substrate 630 can be disposed within housing 622.

Block 3406 includes coupling an analyte sensor comprising an elongated body having at least a first bend to at least one of the housing and the electronics assembly substrate. For example, analyte sensor 138 can be coupled to at least one of housing 622 and electronics assembly substrate 630 and comprises an elongated body having at least a first bend 1102a-c, 1202, 1302, 1402, 1502, 1602, 1702, 1802, 1902 or 2002, as previously described in connection with FIGS. 11A-20.

In some embodiments, method 3400 can further involve providing one or more bends in sensor 138 to locate and/or hold sensor 138 in a desired orientation with respect to electronic assembly substrate 630, as previously described in connection with FIGS. 11A-20.

Method 3400 can further comprise, for example, forming a first bend 1202, 1302 in analyte sensor 138 such that a portion of the elongated body distal of first bend 1202, 1302 extends substantially parallel to a plane of electronics assembly substrate 630 and a portion of the elongated body proximal to first bend 1202, 1302 extends substantially perpendicular to the plane of electronics assembly substrate 630 and at least partially into electronics assembly substrate 630. In some embodiments, lower housing 622 can comprise recess 1216, and method 3400 can further comprise extending at least some of the portion of the elongated body proximal to first bend 1202 through electronics assembly substrate 630 and into recess 1206. In some embodiments, the portion of the elongated body proximal to first bend 1302 exerts a biasing force $Fb_{ias}$ against a portion of electronics assembly substrate 630, thereby securing analyte sensor 138 in a desired orientation with respect to electronics assembly substrate 630.

In some embodiments, method 3400 can further comprise, for example, forming first bend 1402, 1502, 1602 in analyte sensor 138 such that a portion of the elongated body distal of first bend 1402, 1502, 1602 extends substantially parallel to a plane of electronics assembly substrate 630 and a portion of the elongated body proximal to first bend 1402, 1502, 1602 extends substantially perpendicular to the plane of electronics assembly substrate 630 and away from electronics assembly substrate 630. Lower housing 622 can further comprise recess 1416 in a sidewall of lower housing 622, and method 3400 can further comprise extending at least some of the portion of the elongated body proximal to first bend 1402, 1502, 1602 within recess 1416, thereby restraining analyte sensor 138 in a desired orientation with respect to electronics assembly substrate 630. In some embodiments, the portion of the elongated body proximal to first bend 1502 exerts a biasing force against a portion of lower housing 622, thereby securing analyte sensor 138 in a desired orientation with respect to electronics assembly substrate 630.

In some embodiments, method 3400 can further comprise forming at least one additional bend 1606, 1608, 1610 in analyte sensor 138 proximal to first bend 1602 such that additional bend(s) 1606, 1608, 1610 causes at least a first part of the elongated body proximal to first bend 1602 and distal to additional bend(s) 1606, 1608, 1610 to extend in a first direction within recess 1416 and exert a first biasing force $Fb_{ias}$ at a first location along recess 1416, and at least a second part of the elongated body proximal to first bend 1602 and proximal to additional bend(s) 1606, 1608, 1610 to extend in a second direction within recess 1416 and exert a second biasing force $Fb_{ias}$ at a second location along recess 1416, thereby securing analyte sensor 138 in a desired orientation with respect to electronics assembly substrate 630.

In some embodiments, method 3400 can further comprise forming first bend 1702, 1802, 1902, 2002 in analyte sensor 138 such that a portion of the elongated body distal of first bend 1702, 1802, 1902, 2002 extends in a first direction substantially parallel to a plane of electronics assembly substrate 630 and a portion of the elongated body proximal to first bend 1702, 1802, 1902, 2002 extends in a second direction that is different from the first direction but also substantially parallel to the plane of electronics assembly substrate 630.

In some embodiments, method 3400 can further comprise forming at least one additional bend 1804, 1806 in analyte sensor 138 proximal to first bend 1802 such that additional bend(s) 1804, 1806 cause at least a first part of the elongated body proximal to first bend 1802 and distal to additional bend(s) 1804, 1806 to extend in the second direction and exert a first biasing force $F_{bias}$ at a first location along one of lower housing 622 and electronics assembly substrate 630, and at least a second part of the elongated body proximal to first bend 1802 and proximal to additional bend(s) 1804, 1806 to extend in a third direction substantially parallel to the plane of electronics assembly substrate 630 and exert a second biasing force $F_{bias}$ at a second location along one of lower housing 622 and electronics assembly substrate 630, thereby securing analyte sensor 138 in a desired orientation with respect to electronics assembly substrate 630.

In some embodiments, electronic assembly substrate 630 can comprise post 1912 and method 3400 can further comprise forming first bend 1902 in the analyte sensor such that a portion of the elongated body distal of first bend 1902 extends in a first direction substantially parallel to a plane of electronics assembly substrate 630 and a portion of the elongated body proximal to first bend 1902 extends substantially along a perimeter of post 1912, thereby securing analyte sensor 138 in a desired orientation with respect to electronics assembly substrate 630.

In some embodiments, the portion of the elongated body distal of first bend 2002 exerts a first biasing force F1 at a first location along one of lower housing 622 and electronics assembly substrate 630, thereby securing analyte sensor 138 in a desired orientation with respect to electronics assembly substrate 630. First bend 2002 can exert a second biasing force F2 at a second location along one of lower housing 622 and electronics assembly substrate 630, thereby further securing analyte sensor 138 in the desired orientation. The portion of the elongated body proximal of first bend 2002 can exert a third biasing force F3 at a third location along one of lower housing 622 and electronics assembly substrate 630, thereby further securing analyte sensor 138 in the desired orientation. In some embodiments, second biasing force F2 is exerted in a substantially opposite direction from third biasing force F3, first biasing force F1 is exerted in a substantially perpendicular direction to each of second biasing force F2 and third biasing force F3, first bend 2002 provides a first torque about first bend 2002 that pushes the portion of the elongated body distal of first bend 2002 against the first location, and/or first bend 2002 provides a second torque about first bend 2002 that pushes the portion of the elongated body proximal of first bend 2002 against the third location.

Figure 35:
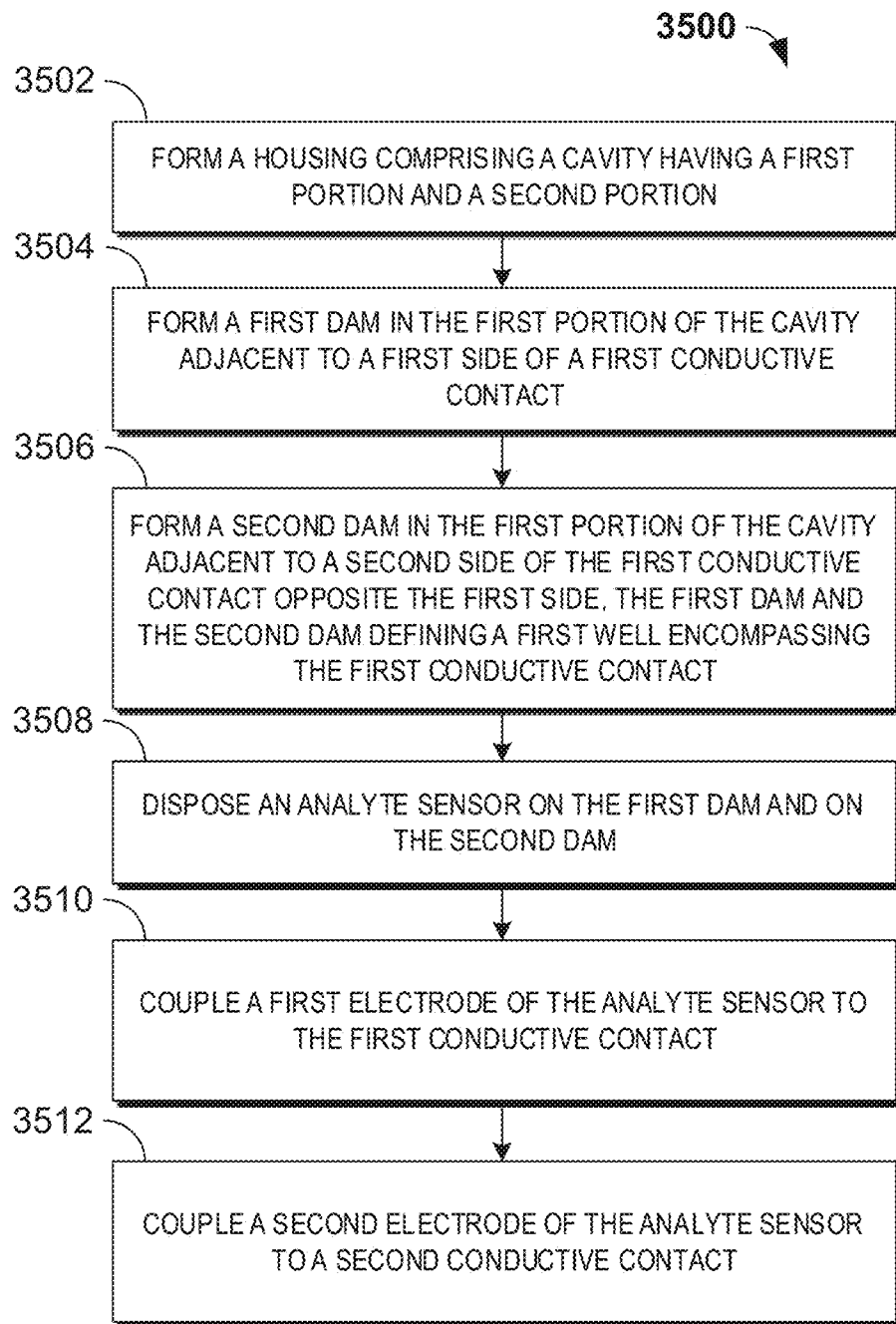
FIG. 35 illustrates another flow chart of illustrative operations that may be performed for manufacturing and using an analyte sensor directly connected to a circuit board of a transmitter, according to some embodiments.

An example method 3500 for fabricating an analyte sensing apparatus will now be described in connection with FIG. 35 below.

Block 3502 includes forming a housing comprising a cavity having a first portion and a second portion. For example, as previously described in connection with FIGS. 6A-10, lower housing 622 can be formed comprising cavity 750 having first portion 752 and second portion 754.

Block 3504 includes forming a first dam in the first portion of the cavity adjacent to a first side of the first conductive contact. For example, first dam 2112 can be formed in a first portion of a cavity adjacent to a first side of first conductive contact 334.

Block 3506 includes forming a second dam in the first portion of the cavity adjacent to a second side of the first conductive contact opposite the first side, the first dam and the second dam defining a first well encompassing the first conductive contact. For example, second dam 2114 can be formed in a first portion of a cavity adjacent to a second side of first conductive contact 334 opposite the first side. First dam 2112 and second dam 2114 define first well 2102 encompassing first conductive contact 334.

Block 3508 includes disposing an analyte sensor on the first dam and on the second dam. For example, analyte sensor 138 can be disposed on first dam 2112 and on second dam 2114.

Block 3510 includes coupling a first electrode of the analyte sensor to the first conductive contact. For example, first electrode 212*b* of analyte sensor 138 can be coupled to first conductive contact 334.

Block 3512 includes coupling a second electrode of the analyte sensor to the second conductive contact. For example, second electrode 211*b* of analyte sensor 138 can be coupled to second conductive contact 324.

In some embodiments, method 3500 can further comprise disposing an electronics assembly substrate within the housing, wherein the first and second conductive contacts extend from the electronics assembly substrate into the first portion of the cavity. For example, electronics assembly substrate 630 can be disposed within housing 622, wherein first and second conductive contacts 324, 334 extend from electronics assembly substrate 630 into the first portion of the cavity (see, e.g., FIGS. 6A-6C and 21A-21D).

In some embodiments, first dam 2112 and second dam 2114 each comprise a sloped cross-section and analyte sensor 138 can rest on a lowest point of the sloped cross-section of first dam 2112 and on a lowest point of the sloped cross-section of second dam 2114. The sloped cross-sections can be one of triangularly-recessed, parabolically-recessed, semi-circularly-recessed or hyperbolically-recessed cross-sections.

In some embodiments, method 3500 can further comprise disposing conductive epoxy 2122 over at least a portion of first conductive contact 334 within first well 2102. Conductive epoxy 2122 is disposed at least to a height of the lowest point of the sloped cross-section of first dam 2112 or of the lowest point of the sloped cross-section of second dam 2114 such that first electrode 212b of analyte sensor 138 is in direct physical and electrical contact with conductive epoxy 2122 when disposed on first dam 2112 and on second dam 2114.

Figure 36:
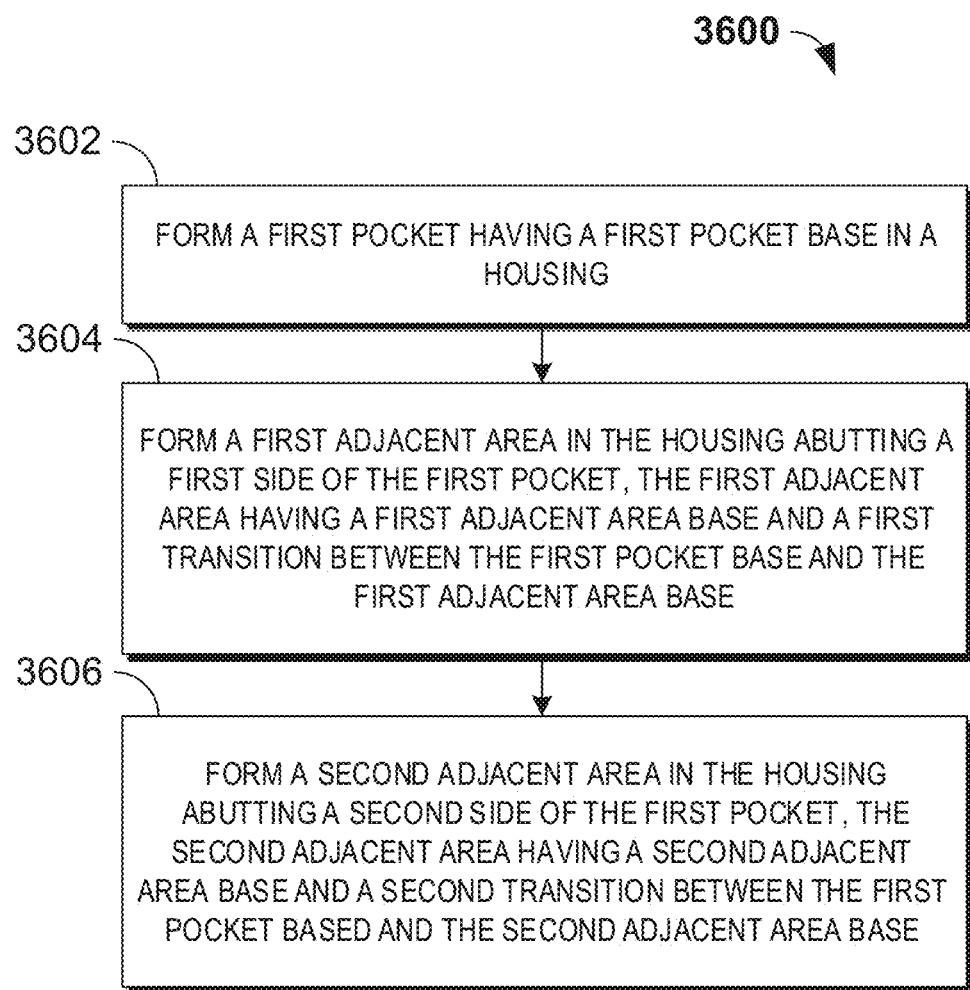
FIG. 36 illustrates another flow chart of illustrative operations that may be performed for manufacturing and using an analyte sensor directly connected to a circuit board of a transmitter, according to some embodiments.

An example method 3600 for fabricating an analyte sensing apparatus housing will now be described in connection with FIG. 36 below. Method 3600 may correspond at least to the previous description in connection with FIGS. 22-27.

Block 3602 includes forming a first pocket in a housing having a first pocket base. For example, lower housing 622 can be formed as previously described in connection with at least FIGS. 6A-10 and, as previously described in connection with FIGS. 22-27, first pocket 2400a-c, 2700a having first pocket base 2405a-c can be formed in housing 622.

Block 3604 includes forming a first adjacent area in the housing abutting a first side of the first pocket, the first adjacent area having a first adjacent area base and a first transition between the first pocket base and the first adjacent area base. For example, first adjacent area 2410a-c, 2710a abutting a first side of first pocket 2400a-c, 2700a can be formed in housing 622. First adjacent area 2410a-c, 2710a can have first adjacent area base 2415a-c and a first transition 2404a-c between first pocket base 2405a-c and first adjacent area base 2415a-c.

Block 3608 includes forming a second adjacent area in the housing abutting a second side of the first pocket, the second adjacent area having a second adjacent area base and a second transition between the first pocket base and the second adjacent area base. For example, second adjacent area 2420a-c, 2720 abutting a second side of first pocket 2400a-c, 2700a-b can be formed in housing 622. Second adjacent area 2420a-c, 2720 can have second adjacent area base 2425a-c and second transition 2406a-c between first pocket base 2405a-c and second adjacent area base 2420a-c.

In some embodiments, method 3600 can further comprise disposing electronics assembly substrate 630 within housing 622.

In some embodiments, first pocket 2400a-c, 2700a can have any of a substantially rectangular-shaped (e.g., 2300a), diamond-shaped (e.g., 2300c), or polygonal-shaped (e.g., 2300c) geometry such that sidewalls of first pocket 2400a-c, 2700a are substantially planar and meet one another to form angled corners. Alternatively, first pocket 2400a-c, 2700a can have any of a substantially rounded rectangular-shaped (e.g., 2300b), rounded diamond-shaped, or rounded polygonal-shaped geometry such that portions of sidewalls of first pocket 2400a-c, 2700a are substantially planar while other portions of the sidewalls that connect the substantially planar portions are curved.

In some embodiments, as described in connection with at least callout "F" of FIG. 22 and the "step up" views of FIGS. 24 and 25, at least one of first adjacent area base and the second adjacent area base are disposed at an elevated height "h" compared to the first pocket base such that at least one of first transition 2204f, 2404c and second transition 2206f, 2406c step up from the first pocket base. In some embodiments, the elevated height "h" is approximately 0.5 millimeters. In some embodiments, first predetermined amount of epoxy 2430c forms an upward-inflecting meniscus 2432c at first and second transitions 2404c, 2406c and the elevated height "h" exceeds a height of upward-inflecting meniscus 2432c. In some embodiments, elevated height "h" is a function of the first predetermined amount and at least one of a viscosity, a surface energy and a surface tension characteristic of epoxy 2430c.

In some embodiments, as described in connection with at least callout "P" of FIG. 22 and the "flush" views of FIGS. 24 and 25, at least one of the first adjacent area base and the second adjacent area base are disposed at a same height as the first pocket base such that at least one of first transition 2204p, 2404b and second transition 2206p, 2406b are flush with the first pocket base.

In some embodiments, as described in connection with at least callout "E" of FIG. 22, the "step-down" views of FIGS. 24 and 25, and FIG. 27, at least one of the first adjacent area base and the second adjacent area base are disposed at a lower height "h" compared to the first pocket base such that at least one of first transition 2204e, 2404a and second transition 2206e, 2406a step down from the first pocket base. In some embodiments, lower height "h" is approximately 0.5 millimeters. In some embodiments, first predetermined amount of epoxy 2430a forms a downward-inflecting meniscus 2432a at first and second transitions 2404a, 2406a, thereby causing epoxy 2430a to adhere to the at least one of first and second transitions 2404a, 2406a and preventing epoxy 2430c from creeping into first 2210e, 2410a, 2710a and second 2220e, 2420a, 2720 adjacent areas.

In some embodiments, first adjacent area 2410a-c, 2710a and second adjacent area 2420a-c, 2720 can have any of the geometries described above for the pockets. In some embodiments, one or more sidewalls 2402a-c of first pocket 2400a-c are disposed substantially perpendicular to the first pocket base, or alternatively, at an angle from substantially perpendicular to the first pocket base. In some embodiments, one or more sidewalls 2412a-c, 2422a-c of first and second adjacent areas 2410a-c, 2420a-c are disposed substantially perpendicular to the respective first and second adjacent area bases, or alternatively, at an angle from substantially perpendicular to the first and second adjacent area bases. In some embodiments, one or more sidewalls 2408c of first and second transitions 2404a-c, 2406a-c are disposed substantially perpendicular to the first pocket base, or alternatively, at an angle from substantially perpendicular to the first pocket base. In some embodiments, sidewalls 2408c of at least one of first and second transitions 2404a-c, 2406a-c are rounded such that angled corners are not formed at first and second transitions 2404a-c, 2406a-c.

In some embodiments, a first width of first transition 2404a-c and a second width of second transition 2406a-c are substantially within the range of 0.5 mm and 2.0 mm. In some embodiments, the first width of first transition 2404a-c is greater than the second width of second transition 2406a-c. In some other embodiments, the first width of first transition 2404a-c is less than the second width of second transition 2406a-c.

In some embodiments, method 3600 can further include, for example, disposing conductive contact 324, 334 in first adjacent area 2710a or in second adjacent area 2720 of electronics assembly substrate 630. In some embodiments, analyte sensor 138 comprises first electrode 211b and second electrode 212b, and method 3600 can further comprise, for example, disposing analyte sensor 138 on housing 622 and electrically connecting at least one of first electrode 211b and second electrode 212b with conductive contacts 324, 334.

In some embodiments, as previously described in connection with at least FIG. 27, method 3600 can further include, for example, disposing post 2712 in first adjacent area 2710b or in second adjacent area 2720, disposing a second predetermined amount of epoxy on post 2712, and disposing a portion of analyte sensor 138 in the second predetermined amount of epoxy on post 2712. The second predetermined amount of epoxy exerts a centering force on the portion of analyte sensor 138 disposed therein such that analyte sensor 138 is aligned substantially along a centerline of post 2712. Post 2712 can have a substantially symmetrical geometry about a centerline of post 2712.

In some embodiments, method 3600 can further include providing the pocket base with a first surface energy and providing the first adjacent area base with a second surface energy different from the first surface energy. For example, as previously described in connection with FIGS. 40A-40B, pocket base 4005*a-b* can have a first surface energy and first adjacent area base 4015*a-b* can have a second surface energy different from the first surface energy.

In some embodiments, method 3600 can further include providing the second adjacent area base with one of the second surface energy and a third surface energy different from the first and second surface energies. For example, as previously described in connection with FIGS. 40A-40B, second adjacent area base 4025*a-b* can have one of the second surface energy and a third surface energy different from the first and second surface energies.

Figure 37:
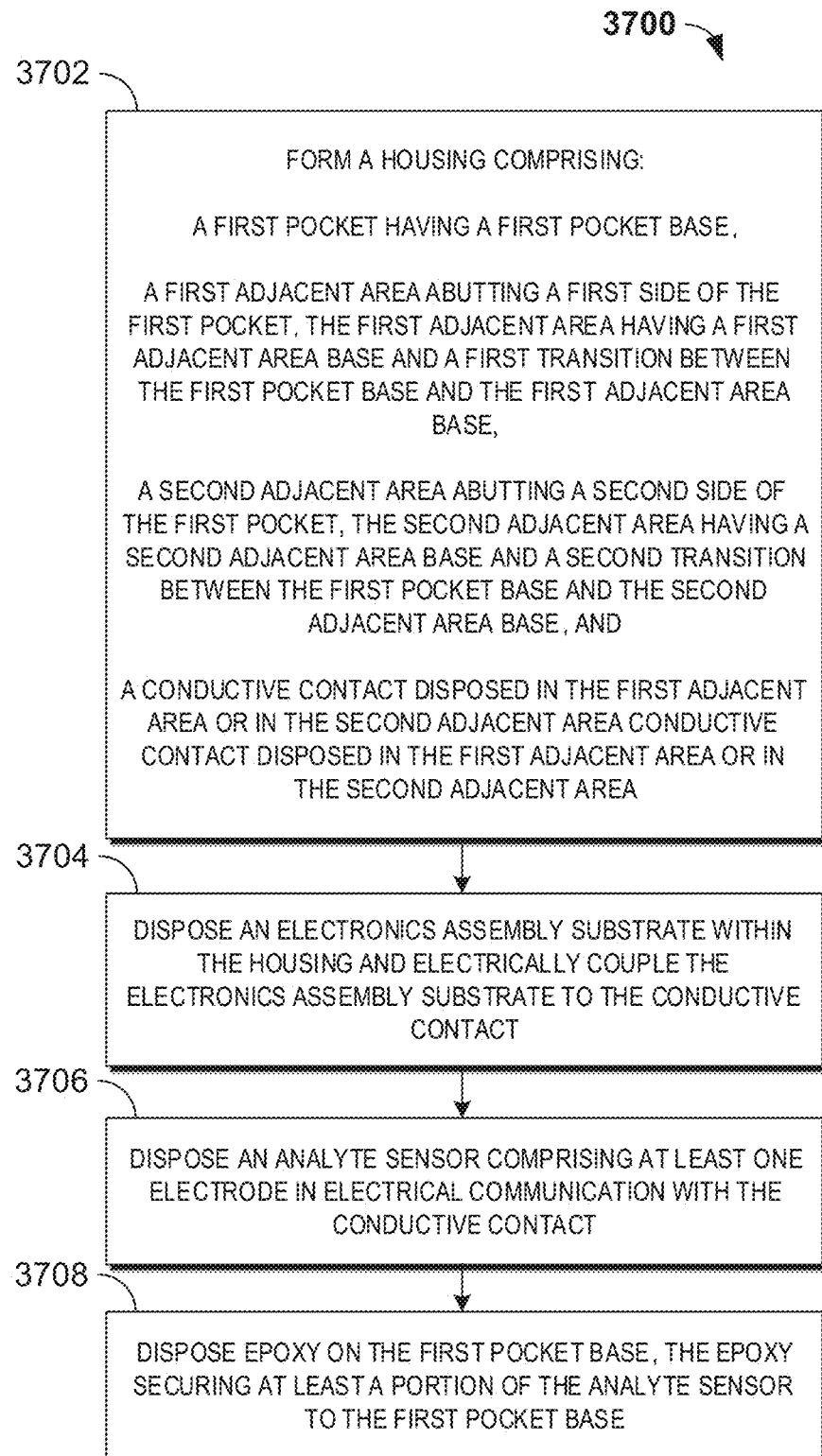
FIG. 37 illustrates another flow chart of illustrative operations that may be performed for manufacturing and using an analyte sensor directly connected to a circuit board of a transmitter, according to some embodiments.

An example method 3700 for fabricating an analyte sensing apparatus will now be described in connection with FIG. 37 below. Method 3700 may also correspond at least to the previous description in connection with FIGS. 22-27.

Block 3702 includes forming a housing comprising a first pocket having a first pocket base, a first adjacent area abutting a first side of the first pocket, the first adjacent area having a first adjacent area base and a first transition between the first pocket base and the first adjacent area base, a second adjacent area abutting a second side of the first pocket, the second adjacent area having a second adjacent area base and a second transition between the first pocket base and the second adjacent area base, and a conductive contact disposed in the first adjacent area or in the second adjacent area. For example, lower housing 622 can be formed as previously described in connection with at least FIGS. 6A-10 and, as previously described in connection with FIGS. 22-27, first pocket 2400*a-c*, 2700*a* having first pocket base 2405*a-c* can be formed in housing 622. First adjacent area 2410*a-c*, 2710*a* abutting a first side of first pocket 2400*a-c*, 2700*a* can be formed in housing 622. First adjacent area 2410*a-c*, 2710*a* can have first adjacent area base 2415*a-c* and a first transition 2404*a-c* between first pocket base 2405*a-c* and first adjacent area base 2415*a-c*. Second adjacent area 2420*a-c*, 2720 abutting a second side of first pocket 2400*a-c*, 2700*a-b* can be formed in housing 622. Second adjacent area 2420*a-c*, 2720 can have second adjacent area base 2425*a-c* and second transition 2406*a-c* between first pocket base 2405*a-c* and second adjacent area base 2420*a-c*. Conductive contact(s) 324, 334 can be disposed in first adjacent area 2410*a-c* or in second adjacent area 2420*a-c*.

Block 3704 includes disposing an electronics assembly substrate within the housing and electrically coupling the electronics assembly substrate to the conductive contact. For example, electronics assembly substrate 630 can be disposed within housing 622 electronics assembly substrate 630 can be electrically coupled to conductive contact(s) 324, 334.

Block 3706 includes disposing an analyte sensor comprising at least one electrode in electrical communication with the conductive contact. For example, analyte sensor 138 comprises at least one electrode 211*b*, 212*b*, which can be disposed in electrical communication with conductive contact(s) 324, 344.

Block 3708 includes disposing epoxy on the first pocket base, the epoxy securing at least a portion of the analyte sensor to the first pocket base. For example, epoxy can be disposed on first pocket base 2405*a-c* such that the epoxy secures at least a portion of analyte sensor 138 to first pocket base 2405*a-c*.

In some embodiments, as described in connection with at least callout "F" of FIG. 22 and the "step up" views of FIGS. 24 and 25, at least one of first adjacent area base and the second adjacent area base are disposed at an elevated height "h" compared to the first pocket base such that at least one of first transition 2204*f*, 2404*c* and second transition 2206*f*, 2406*c* step up from the first pocket base. In some embodiments, first predetermined amount of epoxy 2430*c* forms an upward-inflecting meniscus 2432*c* at first and second transitions 2404*c*, 2406*c* and the elevated height "h" exceeds a height of upward-inflecting meniscus 2432*c*.

In some embodiments, as described in connection with at least callout "P" of FIG. 22 and the "flush" views of FIGS. 24 and 25, at least one of the first adjacent area base and the second adjacent area base are disposed at a same height as the first pocket base such that at least one of first transition 2204*p*, 2404*b* and second transition 2206*p*, 2406*b* are flush with the first pocket base.

In some embodiments, as described in connection with at least callout "E" of FIG. 22, the "step-down" views of FIGS. 24 and 25, and FIG. 27, at least one of the first adjacent area base and the second adjacent area base are disposed at a lower height "h" compared to the first pocket base such that at least one of first transition 2204*e*, 2404*a* and second transition 2206*e*, 2406*a* step down from the first pocket base. In some embodiments, first predetermined amount of epoxy 2430*a* forms a downward-inflecting meniscus 2432*a* at first and second transitions 2404*a*, 2406*a*, thereby causing epoxy 2430*a* to adhere to the at least one of first and second transitions 2404*a*, 2406*a* and preventing epoxy 2430*c* from creeping into first 2210*e*, 2410*a*, 2710*a* and second 2220*e*, 2420*a*, 2720 adjacent areas.

Figure 38:
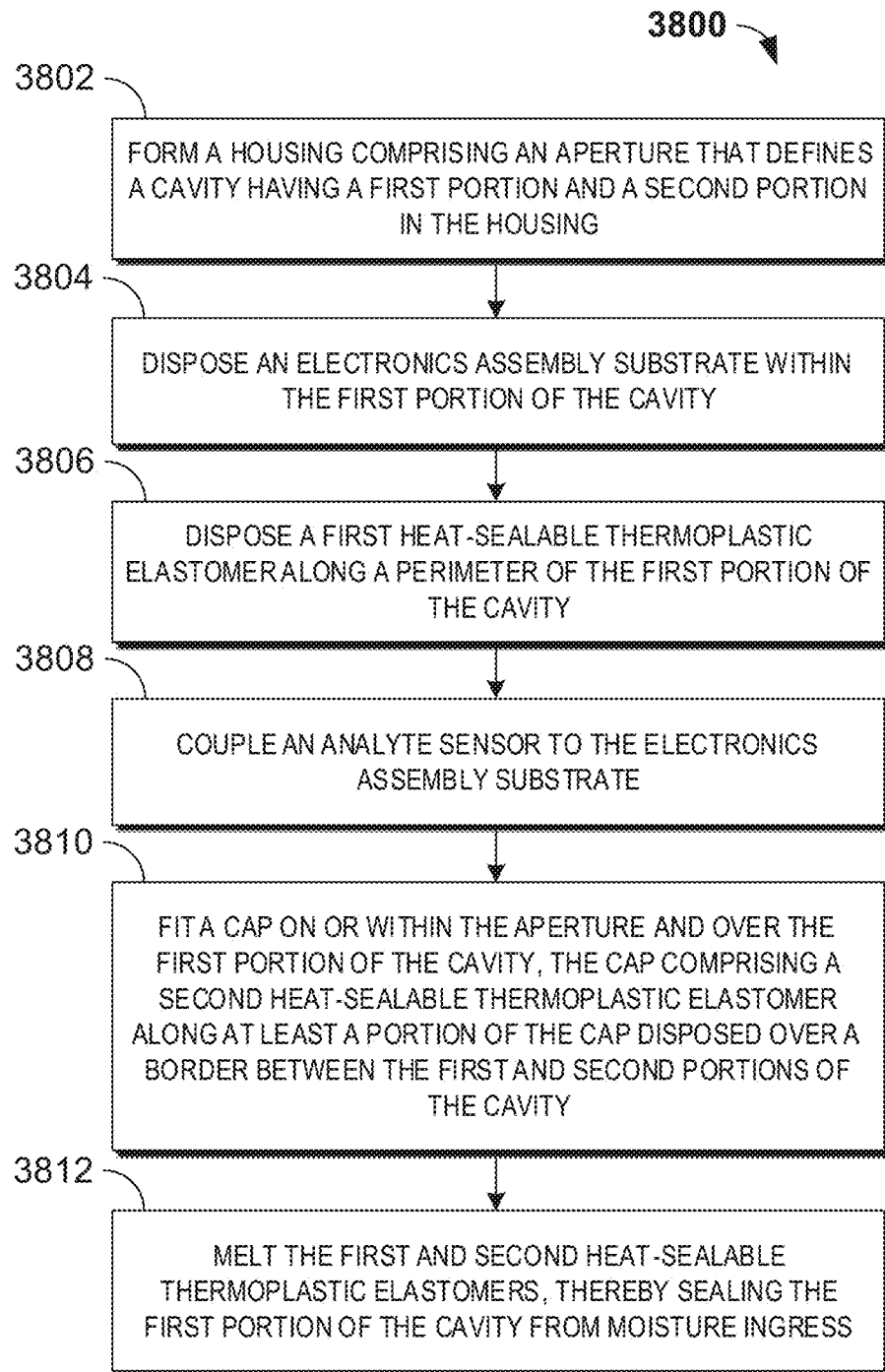
FIG. 38 illustrates another flow chart of illustrative operations that may be performed for manufacturing and using an analyte sensor directly connected to a circuit board of a transmitter, according to some embodiments.

An example method 3800 for fabricating an analyte sensing apparatus will now be described in connection with FIG. 38 below. Method 3800 may correspond to embodiments at least as previously discussed in connection with FIGS. 30A-30B.

Block 3802 includes forming a housing comprising an aperture that defines a cavity having a first portion and a second portion in the housing. For example, as previously described in connection with FIGS. 6A-10, lower housing 622 can be formed comprising aperture 626 that defines cavity 750 having first portion 752 and second portion 754 in lower housing 622.

Block 3804 includes disposing a first heat-sealable thermoplastic elastomer along a perimeter of the first portion of the cavity. For example, first heat-sealable thermoplastic elastomer 3002 can be disposed along a perimeter of first portion 752 of cavity 750.

Block 3806 includes disposing at least a portion of an analyte sensor within the first portion of the cavity. For example, at least a proximal portion of analyte sensor 138 can be disposed within first portion 752 of cavity 750.

Block 3810 includes fitting a cap on or within the aperture and over the first portion of the cavity, the cap comprising a second heat-sealable thermoplastic elastomer along at least a portion of the cap disposed over a border between the first and second portions of the cavity. For example, cap 3004 can comprise second heat-sealable thermoplastic elastomer 3006 along at least a portion of cap 3004 disposed over a border between first 752 and second 754 portions of cavity 750.

Cap 3004 can be fitted on or within aperture 626 and over first portion 752 of cavity 750.

Block 3812 includes melting the first and second heat-sealable thermoplastic elastomers, thereby sealing the first portion of the cavity from moisture ingress. For example, first 3002 and second 3006 heat-sealable thermoplastic elastomers can be melted, for example by exposure to a laser or a similar heat source, thereby sealing first portion 752 of cavity 750 from moisture ingress. In some embodiments, the border between first 752 and second 754 portions of cavity 750 comprises a portion of first heat-sealable thermoplastic elastomer 3002.

Figure 39:
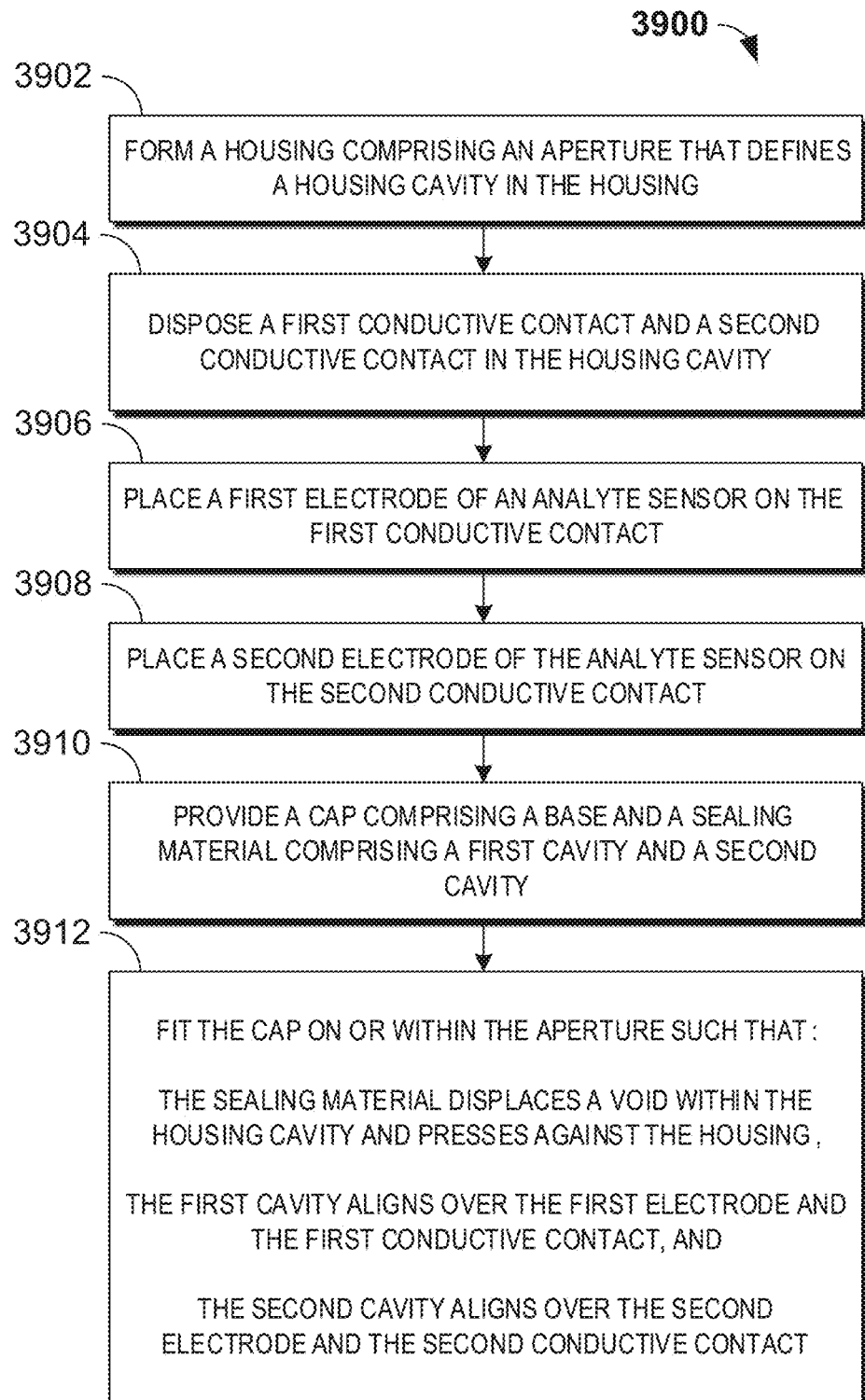
FIG. 39 illustrates another flow chart of illustrative operations that may be performed for manufacturing and using an analyte sensor directly connected to a circuit board of a transmitter, according to some embodiments.

An example method for fabricating an analyte sensing apparatus will now be described in connection with FIG. 39 below. Method 3900 may correspond to embodiments at least as previously discussed in connection with FIGS. 31 and 32.

Block 3902 includes forming a housing comprising an aperture that defines a housing cavity in the housing. For example, lower housing 622 can be formed comprising aperture 626 that defines cavity 750 in lower housing 622.

Block 3904 includes disposing a first conductive contact and a second conductive contact in the housing cavity. For example, first conductive contact 324 and second conductive contact 334 can be disposed within cavity 750.

Block 3906 includes placing a first electrode of an analyte sensor on the first conductive contact. For example, first electrode 211*b* of analyte sensor 138 can be placed on first conductive contact 324.

Block 3908 includes placing a second electrode of the analyte sensor on the second conductive contact. For example, second electrode 212*b* of analyte sensor 138 can be placed on second conductive contact 334.

Block 3910 includes providing a cap comprising a base and a sealing material comprising a first cavity and a second cavity. For example, cap 3100, 3200 can include base 3102, 3202 and sealing material 2104, 3204 comprising a first cavity and a second cavity.

Block 3912 includes fitting the cap on or within the aperture such that the sealing material at least partially fills the housing cavity and presses against the housing, the first cavity aligns over the first electrode and the first conductive contact, and the second cavity aligns over the second electrode and the second conductive contact. For example, cap 3100, 3200 can be fit on or within aperture 626 such that sealing material 3104, 3204 fills or partially fills cavity 750 above electronics assembly substrate 630 and presses against electronics assembly substrate 630, the first cavity aligns over first electrode 211*b* and first conductive contact 324, and the second cavity aligns over second electrode 212*b* and second conductive contact 334.

In some embodiments, method 3900 may further comprise, before fitting cap 3100 on or within aperture 626, disposing first conductive elastomeric puck 3106 in the first cavity, and disposing second conductive elastomeric puck 3108 in the second cavity. First conductive elastomeric puck 3106 is configured to press against first electrode 211*b* and first conductive contact 324 when cap 3100 is fitted on or within aperture 626, thereby securing first electrode 211*b* to first conductive contact 324. Second conductive elastomeric puck 3108 is configured to press against second electrode 212*b* and second conductive contact 334 when cap 3100 is fitted on or within aperture 626, thereby securing second electrode 212*b* to second conductive contact 334. In some embodiments, first and second conductive elastomeric pucks 3106, 3108 have a substantially cylindrical shape.

In some embodiments, base 3202 of cap 3200 further comprises at least first hole 3216 that aligns laterally with first cavity 3210 and second hole 3218 that aligns laterally with second cavity 3212. At least a portion of sealing material 3204 physically isolates first hole 3216 from first cavity 3210 and second hole 3218 from second cavity 3212. In some embodiments, method 3900 may further comprise injecting conductive epoxy 3206 into first cavity 3210 through first hole 3216 and through the portion of sealing material 3204, thereby electrically connecting first electrode 211*b* to first conductive contact 324 and injecting conductive epoxy 3208 into second cavity 3212 through second hole 3218 and through the portion of sealing material 3204, thereby electrically connecting second electrode 212*b* to second conductive contact 334. In some embodiments, first and second cavities 3210, 3212 have a substantially conical shape.

The connections between the elements shown in some figures illustrate exemplary communication paths. Additional communication paths, either direct or via an intermediary, may be included to further facilitate the exchange of information between the elements. The communication paths may be bi-directional communication paths allowing the elements to exchange information.

Various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 2) may be implemented or performed with a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, various functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, WiFi, Bluetooth®, RFID, NFC, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,"desired," or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

Various system and methods described may be fully implemented and/or controlled in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where factory calibration schemes are contemplated, the plural inputs may allow plural users to input relevant data at the same time.

What is claimed is:

1. An analyte sensing apparatus, comprising:
   a housing;
   an electronics assembly substrate disposed within the housing;
   an analyte sensor comprising an elongated body having at least a first bend and a first portion of the elongated body proximal of the first bend extending substantially parallel to a plane of the electronics assembly substrate and a second portion of the elongated body distal of the first bend, the second portion configured to be positioned in vivo, the first bend angling the second portion away from the first portion at an angle greater than 90 degrees and less than 180 degrees; and
   a second bend oriented such that the first portion of the elongated body is distal of the second bend and a portion of the elongated body proximal to the second bend extends substantially perpendicular to the plane of the electronics assembly substrate.

2. The apparatus of claim 1, wherein the second bend extends at least partially into the electronics assembly substrate.

3. The apparatus of claim 2, wherein the housing comprises a recess and at least some of the portion of the elongated body proximal to the second bend extends through the electronics assembly substrate and into the recess.

4. The apparatus of claim 1, wherein the portion of the elongated body proximal to the second bend contacts a portion of the electronics assembly substrate to exert a biasing force against the portion of the electronics assembly substrate, thereby securing the analyte sensor in a desired orientation with respect to the electronics assembly substrate.

5. The apparatus of claim 1, wherein the second bend extends away from the electronics assembly substrate.

6. The apparatus of claim 5, wherein the housing further comprises a recess in a sidewall of the housing, at least some of the portion of the elongated body proximal to the second bend extends within the recess and thereby restrains the analyte sensor in a desired orientation with respect to the electronics assembly substrate.

7. The apparatus of claim 5, wherein the portion of the elongated body proximal to the second bend contacts a portion of the housing to exert a biasing force against the portion of the housing, thereby securing the analyte sensor in a desired orientation with respect to the electronics assembly substrate.

8. The apparatus of claim 7, wherein the housing further comprises a recess in the housing, and wherein the elongated body of the analyte sensor comprises at least one additional bend proximal to the second bend, the at least one additional bend causing:
at least a first part of the elongated body proximal to the second bend and distal to the at least one additional bend to extend in a first direction within the recess and to contact a first location along the recess to exert a first biasing force at the first location along the recess, and
at least a second part of the elongated body proximal to the second bend and proximal to the at least one additional bend to extend in a second direction within the recess and to contact a second location along the recess to exert a second biasing force at the second location along the recess,
thereby securing the analyte sensor in a desired orientation with respect to the electronics assembly substrate.

9. An analyte sensing apparatus, comprising:
a housing having a top and a bottom;
an electronics assembly substrate disposed within the housing;
an analyte sensor comprising an elongated body having at least a first bend and a first portion of the elongated body proximal of the first bend extending substantially parallel to a plane of the electronics assembly substrate and a second portion of the elongated body distal of the first bend, the second portion configured to be positioned in vivo, the first bend angling the second portion away from the first portion at an angle greater than 90 degrees and less than 180 degrees; and
a second bend, and wherein the second bend is oriented such that a portion of the elongated body distal of the second bend extends in a first direction substantially parallel to a plane of the electronics assembly substrate and a portion of the elongated body proximal to the second bend extends in a second direction that is different from the first direction but also substantially parallel to the plane of the electronics assembly substrate and substantially parallel to a plane of a portion of the bottom of the housing.

10. The apparatus of claim 9, wherein the elongated body of the analyte sensor comprises at least one additional bend proximal to the second bend, the at least one additional bend causing:
at least a first part of the elongated body proximal to the second bend and distal to the at least one additional bend to extend in the second direction and to contact a first location along one of the housing and the electronics assembly substrate to exert a first biasing force at the first location along one of the housing and the electronics assembly substrate, and
at least a second part of the elongated body proximal to the second bend and proximal to the at least one additional bend to extend in a third direction substantially parallel to the plane of the electronics assembly substrate and to contact a second location along one of the housing and the electronics assembly substrate to exert a second biasing force at the second location along one of the housing and the electronics assembly substrate,
thereby securing the analyte sensor in a desired orientation with respect to the electronics assembly substrate.

11. An analyte sensing apparatus, comprising:
a housing;
an electronics assembly substrate disposed within the housing;
an analyte sensor comprising an elongated body having at least a first bend and a first portion of the elongated body proximal of the first bend extending substantially parallel to a plane of the electronics assembly substrate and a second portion of the elongated body distal of the first bend, the second portion configured to be positioned in vivo, the first bend angling the second portion away from the first portion at an angle greater than 90 degrees and less than 180 degrees; and
a second bend, and wherein the electronics assembly substrate comprises a post and the second bend is oriented such that a portion of the elongated body distal of the second bend extends in a first direction substantially parallel to the plane of the electronics assembly substrate and a portion of the elongated body proximal to the second bend extends substantially along a perimeter of the post, thereby securing the analyte sensor in a desired orientation with respect to the electronics assembly substrate.

12. The apparatus of claim 11, wherein the portion of the elongated body distal of the second bend contacts a first location along one of the housing and the electronics assembly substrate to exert a first biasing force at the first location along one of the housing and the electronics assembly substrate, thereby securing the analyte sensor in a desired orientation with respect to the electronics assembly substrate.

13. The apparatus of claim 12, wherein the second bend contacts a second location along one of the housing and the electronics assembly substrate to exert a second biasing force at the second location along one of the housing and the electronics assembly substrate, thereby further securing the analyte sensor in the desired orientation.

14. The apparatus of claim 13, wherein the portion of the elongated body proximal of the second bend contacts a third location along one of the housing and the electronics assembly substrate to exert a third biasing force at the third location along one of the housing and the electronics assembly substrate, thereby further securing the analyte sensor in the desired orientation.

15. The apparatus of claim 14, wherein the second biasing force is exerted in a substantially opposite direction from the third biasing force.

16. The apparatus of claim 14, wherein the first biasing force is exerted in a substantially perpendicular direction to each of the second biasing force and the third biasing force.

17. A method of fabricating an analyte sensing apparatus, the method comprising:
  fabricating a housing;
  disposing an electronics assembly substrate within the housing;
  coupling an analyte sensor comprising an elongated body having at least a first bend to at least one of the housing and the electronics assembly substrate, the elongated body having a first portion proximal of the first bend extending substantially parallel to a plane of the electronics assembly substrate and a second portion distal of the first bend, the second portion configured to be positioned in vivo, the first bend angling the second portion away from the first portion at an angle greater than 90 degrees and less than 180 degrees; and
  forming a second bend oriented such that the first portion of the elongated body is distal of the second bend and a portion of the elongated body proximal to the second bend extends substantially perpendicular to the plane of the electronics assembly substrate.

18. The method of claim 17, wherein the second bend extends at least partially into the electronics assembly substrate.

19. The method of claim 18, wherein the portion of the elongated body proximal to the second bend contacts a portion of the electronics assembly substrate to exert a biasing force against the portion of the electronics assembly substrate, thereby securing the analyte sensor in a desired orientation with respect to the electronics assembly substrate.

20. The method of claim 18, wherein the portion of the elongated body proximal to the second bend contacts a portion of the housing to exert a biasing force against the portion of the housing, thereby securing the analyte sensor in a desired orientation with respect to the electronics assembly substrate.

21. The method of claim 18, wherein the housing further comprises a recess in the housing, and the method further comprises forming at least one additional bend in the analyte sensor proximal to the second bend such that the at least one additional bend causes:
  at least a first part of the elongated body proximal to the second bend and distal to the at least one additional bend to extend in a first direction within the recess and contact a first location along the recess to exert a first biasing force at the first location along the recess, and
  at least a second part of the elongated body proximal to the second bend and proximal to the at least one additional bend to extend in a second direction within the recess and contact a second location along the recess to exert a second biasing force at the second location along the recess,
  thereby securing the analyte sensor in a desired orientation with respect to the electronics assembly substrate.

22. A method of fabricating an analyte sensing apparatus, the method comprising:
  fabricating a housing having a top and a bottom;
  disposing an electronics assembly substrate within the housing;
  coupling an analyte sensor comprising an elongated body having at least a first bend to at least one of the housing and the electronics assembly substrate, the elongated body having a first portion proximal of the first bend extending substantially parallel to a plane of the electronics assembly substrate and a second portion distal of the first bend, the second portion configured to be positioned in vivo, the first bend angling the second portion away from the first portion at an angle greater than 90 degrees and less than 180 degrees; and
  forming a second bend in the analyte sensor such that a portion of the elongated body distal of the second bend extends in a first direction substantially parallel to a plane of the electronics assembly substrate and a portion of the elongated body proximal to the second bend extends in a second direction that is different from the first direction but also substantially parallel to the plane of the electronics assembly substrate and substantially parallel to a plane of a portion of the bottom of the housing.

23. The method of claim 22, further comprising forming at least one additional bend in the analyte sensor proximal to the second bend such that the at least one additional bend causes:
  at least a first part of the elongated body proximal to the second bend and distal to the at least one additional bend to extend in the second direction and contact a first location along one of the housing and the electronics assembly substrate to exert a first biasing force at the first location along one of the housing and the electronics assembly substrate, and
  at least a second part of the elongated body proximal to the second bend and proximal to the at least one additional bend to extend in a third direction substantially parallel to the plane of the electronics assembly substrate and contact a second location along one of the housing and the electronics assembly substrate to exert a second biasing force at the second location along one of the housing and the electronics assembly substrate,
  thereby securing the analyte sensor in a desired orientation with respect to the electronics assembly substrate.

24. The method of claim 22, wherein the portion of the elongated body distal of the second bend contacts a first location along one of the housing and the electronics assembly substrate to exert a first biasing force at the first location along one of the housing and the electronics assembly substrate, thereby securing the analyte sensor in a desired orientation with respect to the electronics assembly substrate.

25. The method of claim 24, wherein the second bend contacts a second location along one of the housing and the electronics assembly substrate to exert a second biasing force at the second location along one of the housing and the electronics assembly substrate, thereby further securing the analyte sensor in the desired orientation.

26. The method of claim 24, wherein the second bend provides a first torque about the second bend that pushes the portion of the elongated body distal of the second bend against the first location.

27. The method of claim 26, wherein the second bend provides a second torque about the second bend that pushes the portion of the elongated body proximal of the second bend against a second location along one of the housing and the electronics assembly substrate.

* * * * *